(12) United States Patent
Chou et al.

(10) Patent No.: US 11,796,428 B2
(45) Date of Patent: *Oct. 24, 2023

(54) COMPRESSED OPEN FLOW ASSAY AND USE

(71) Applicant: Essenlix Corporation, Monmouth Junction, NJ (US)

(72) Inventors: Stephen Y. Chou, Princeton, NJ (US); Wei Ding, East Windsor, NJ (US); Ji Qi, Lawrence Township, NJ (US); Yufan Zhang, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/592,410

(22) Filed: Feb. 3, 2022

(65) Prior Publication Data
US 2022/0236149 A1    Jul. 28, 2022

Related U.S. Application Data

(63) Continuation of application No. 16/078,316, filed as application No. PCT/US2018/017307 on Feb. 7, 2018, now Pat. No. 11,274,996.
(Continued)

(51) Int. Cl.
*G01N 1/28* (2006.01)
*G01N 33/483* (2006.01)

(52) U.S. Cl.
CPC ....... *G01N 1/2813* (2013.01); *G01N 33/4833* (2013.01); *G01N 1/286* (2013.01); *G01N 2001/282* (2013.01)

(58) Field of Classification Search
CPC .. G01N 1/2813; G01N 33/4833; G01N 1/286; G01N 2001/282; B01L 2300/0627;
(Continued)

(56) References Cited

U.S. PATENT DOCUMENTS

| | | | |
|---|---|---|---|
| 3,368,872 A | 2/1968 | Natelson | |
| 3,447,863 A | 6/1969 | Patterson | |

(Continued)

FOREIGN PATENT DOCUMENTS

| | | | |
|---|---|---|---|
| CN | 1299466 | 6/2001 | |
| CN | 1302229 | 7/2001 | |

(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015.
(Continued)

*Primary Examiner* — Dennis White

(57) ABSTRACT

The present invention relates to the methods, devices, and systems that make bio/chemical sensing (including, not limited to, immunoassay, nucleic assay, electrolyte analysis, etc.) faster, more sensitive, less steps, easy to perform, smaller amount of samples required, less or reduced (or no) needs for professional assistance, and/or lower cost, than many current sensing methods and devices. The present invention also allows a test performed by a smartphone.

20 Claims, 11 Drawing Sheets

Related U.S. Application Data

(60) Provisional application No. 62/459,972, filed on Feb. 16, 2017, provisional application No. 62/460,062, filed on Feb. 16, 2017, provisional application No. 62/456,504, filed on Feb. 8, 2017, provisional application No. 62/456,065, filed on Feb. 7, 2017.

(58) Field of Classification Search
CPC ..... B01L 2300/0654; B01L 2300/0819; B01L 2300/0887; B01L 3/502707; B01L 3/502715; G02B 21/34; C12Q 1/24
See application file for complete search history.

(56) References Cited

U.S. PATENT DOCUMENTS

| | | | |
|---|---|---|---|
| 3,895,661 | A | 7/1975 | Praglin et al. |
| 3,925,166 | A | 12/1975 | Blume |
| 3,992,158 | A | 11/1976 | Przybylowicz et al. |
| 4,022,521 | A | 5/1977 | Hall et al. |
| 4,066,412 | A | 1/1978 | Johnson et al. |
| 4,088,448 | A | 5/1978 | Lilja et al. |
| 4,171,866 | A | 10/1979 | Tolles |
| 4,233,029 | A | 11/1980 | Columbus |
| 4,255,384 | A | 3/1981 | Kitajima et al. |
| 4,258,001 | A | 3/1981 | Pierce et al. |
| 4,329,054 | A | 5/1982 | Bachalo |
| 4,402,614 | A | 9/1983 | Porath |
| 4,427,294 | A | 1/1984 | Pietro |
| 4,430,436 | A | 2/1984 | Koyama et al. |
| 4,596,695 | A | 6/1986 | Cottingham |
| 4,745,075 | A | 5/1988 | Hadfield et al. |
| 4,806,311 | A | 2/1989 | Greenquist |
| 4,883,642 | A | 11/1989 | Bisconte |
| 4,906,439 | A | 3/1990 | Grenner |
| 4,911,782 | A | 3/1990 | Brown |
| 4,950,455 | A | 8/1990 | Smith |
| 5,002,736 | A | 3/1991 | Babbitt et al. |
| 5,039,487 | A | 8/1991 | Smith |
| 5,096,836 | A | 3/1992 | Macho et al. |
| 5,122,284 | A | 6/1992 | Braynin et al. |
| 5,132,097 | A | 7/1992 | Van Deusen et al. |
| 5,169,601 | A | 12/1992 | Ohta et al. |
| 5,188,968 | A | 2/1993 | Kano et al. |
| 5,223,219 | A | 6/1993 | Subramanian et al. |
| 5,281,540 | A | 1/1994 | Merkh et al. |
| 5,306,467 | A | 4/1994 | Douglas-Hamilton et al. |
| 5,321,975 | A | 6/1994 | Wardlaw |
| 5,362,648 | A | 11/1994 | Koreyasu et al. |
| 5,413,732 | A | 5/1995 | Buhl et al. |
| 5,427,959 | A | 6/1995 | Nishimura et al. |
| 5,431,880 | A | 7/1995 | Kramer |
| 5,591,403 | A | 1/1997 | Gavin et al. |
| 5,623,415 | A | 4/1997 | O'Bryan et al. |
| 5,753,456 | A | 5/1998 | Naqui et al. |
| 5,768,407 | A | 6/1998 | Shen et al. |
| 5,858,648 | A | 1/1999 | Steel et al. |
| 5,879,628 | A | 3/1999 | Ridgeway et al. |
| 5,888,834 | A | 3/1999 | Ishikawa et al. |
| 5,939,326 | A | 8/1999 | Chupp et al. |
| 5,948,686 | A | 9/1999 | Wardlaw |
| 6,004,821 | A | 12/1999 | Levine et al. |
| 6,016,367 | A | 1/2000 | Benedetti et al. |
| 6,017,767 | A | 1/2000 | Chandler |
| 6,022,734 | A | 2/2000 | Wardlaw |
| 6,083,761 | A | 7/2000 | Kedar et al. |
| 6,106,778 | A | 8/2000 | Oku et al. |
| 6,180,314 | B1 | 1/2001 | Berndt |
| 6,235,536 | B1 | 5/2001 | Wardlaw |
| 6,350,613 | B1 | 2/2002 | Wardlaw et al. |
| 6,358,475 | B1 | 3/2002 | Berndt |
| 6,429,027 | B1 | 8/2002 | Chee et al. |
| 6,503,760 | B2 | 1/2003 | Malmqvist et al. |
| 6,551,554 | B1 | 4/2003 | Vermeiden et al. |
| 6,623,701 | B1 | 9/2003 | Eichele |
| 6,632,652 | B1 | 10/2003 | Austin et al. |
| 6,714,287 | B2 | 3/2004 | Berndt |
| 6,723,290 | B1 | 4/2004 | Wardlaw |
| 6,844,201 | B2 | 1/2005 | Malmqvist et al. |
| 6,866,823 | B2 | 3/2005 | Wardlaw |
| 6,869,570 | B2 | 3/2005 | Wardlaw |
| 6,893,850 | B2 | 5/2005 | Ostuni et al. |
| 6,921,514 | B1 | 7/2005 | Vetter et al. |
| 6,929,953 | B1 | 8/2005 | Wardlaw |
| 6,939,032 | B2 | 9/2005 | Cosby et al. |
| 7,101,341 | B2 | 9/2006 | Tsukashima et al. |
| 7,179,423 | B2 | 2/2007 | Bohm et al. |
| 7,282,367 | B2 | 10/2007 | Kawamura |
| 7,393,658 | B2 | 7/2008 | Carbonell et al. |
| 7,410,617 | B2 | 8/2008 | Sakamoto |
| 7,410,807 | B2 | 8/2008 | D'Aurora |
| 7,468,160 | B2 | 12/2008 | Thompson |
| 7,510,841 | B2 | 3/2009 | Stuelpnagel et al. |
| 7,510,848 | B2 | 3/2009 | Hammond et al. |
| 7,547,424 | B2 | 6/2009 | Haab et al. |
| 7,731,901 | B2 | 6/2010 | Wardlaw |
| 7,738,094 | B2 | 6/2010 | Goldberg |
| 7,799,558 | B1 | 9/2010 | Dultz |
| 7,850,916 | B2 | 12/2010 | Wardlaw |
| 7,862,773 | B2 | 1/2011 | Ibrahim |
| 7,863,411 | B2 | 1/2011 | Hammond et al. |
| 7,897,376 | B2 | 3/2011 | Porter et al. |
| 7,901,897 | B2 | 3/2011 | Stuelpnagel et al. |
| 7,903,241 | B2 | 3/2011 | Wardlaw et al. |
| 7,929,121 | B2 | 4/2011 | Wardlaw et al. |
| 7,929,122 | B2 | 4/2011 | Wardlaw et al. |
| 7,943,093 | B2 | 5/2011 | Adrien et al. |
| 7,951,599 | B2 | 5/2011 | Levine et al. |
| 7,995,194 | B2 | 8/2011 | Wardlaw et al. |
| 8,045,165 | B2 | 10/2011 | Wardlaw et al. |
| 8,058,073 | B2 | 11/2011 | Chiapperi et al. |
| 8,077,296 | B2 | 12/2011 | Wardlaw et al. |
| 8,081,303 | B2 | 12/2011 | Levine et al. |
| 8,133,738 | B2 | 3/2012 | Levine et al. |
| 8,144,504 | B2 | 3/2012 | Kim et al. |
| 8,158,434 | B2 | 4/2012 | Wardlaw |
| 8,221,985 | B2 | 7/2012 | Wardlaw et al. |
| 8,241,572 | B2 | 8/2012 | Wardlaw |
| 8,269,954 | B2 | 9/2012 | Levine et al. |
| 8,284,384 | B2 | 10/2012 | Levine et al. |
| 8,287,820 | B2 | 10/2012 | Williams et al. |
| 8,310,658 | B2 | 11/2012 | Wardlaw et al. |
| 8,310,659 | B2 | 11/2012 | Wardlaw et al. |
| 8,319,954 | B2 | 11/2012 | Wardlaw et al. |
| 8,326,008 | B2 | 12/2012 | Lalpuria et al. |
| 8,338,579 | B2 | 12/2012 | Adams et al. |
| 8,361,799 | B2 | 1/2013 | Levine et al. |
| 8,367,012 | B2 | 2/2013 | Wardlaw |
| 8,462,332 | B2 | 6/2013 | Pugia et al. |
| 8,467,063 | B2 | 6/2013 | Wardlaw et al. |
| 8,472,693 | B2 | 6/2013 | Davis et al. |
| 8,481,282 | B2 | 7/2013 | Levine et al. |
| 8,502,963 | B2 | 8/2013 | Levine et al. |
| 8,513,032 | B2 | 8/2013 | Jablonski et al. |
| 8,569,076 | B2 | 10/2013 | Wardlaw et al. |
| 8,594,768 | B2 | 11/2013 | Phillips et al. |
| 8,604,161 | B2 | 12/2013 | Hammond et al. |
| 8,628,952 | B2 | 1/2014 | Stuelpnagel et al. |
| 8,633,013 | B2 | 1/2014 | Kaiser et al. |
| 8,638,427 | B2 | 1/2014 | Wardlaw et al. |
| 8,717,673 | B2 | 5/2014 | Selvin et al. |
| 8,741,630 | B2 | 6/2014 | Dickinson et al. |
| 8,750,966 | B2 | 6/2014 | Phillips et al. |
| 8,778,687 | B2 | 7/2014 | Levine et al. |
| 8,781,203 | B2 | 7/2014 | Davis et al. |
| 8,796,186 | B2 | 8/2014 | Shirazi |
| 8,797,527 | B2 | 8/2014 | Hukari et al. |
| 8,835,186 | B2 | 9/2014 | Jablonski et al. |
| 8,837,803 | B2 | 9/2014 | Wang et al. |
| 8,842,264 | B2 | 9/2014 | Wardlaw et al. |
| 8,885,154 | B2 | 11/2014 | Wardlaw et al. |
| 8,906,700 | B2 | 12/2014 | Lim et al. |
| 8,911,815 | B2 | 12/2014 | Kram |
| 8,974,732 | B2 | 3/2015 | Lalpuria et al. |
| 8,994,930 | B2 | 3/2015 | Levine et al. |

(56) References Cited

U.S. PATENT DOCUMENTS

| | | |
|---|---|---|
| 9,005,901 B2 | 4/2015 | Gayda et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2003/0068614 A1 | 4/2003 | Cima et al. |
| 2004/0131345 A1 | 7/2004 | Kylberg et al. |
| 2004/0156755 A1 | 8/2004 | Levine |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0254995 A1 | 11/2005 | Sostek et al. |
| 2006/0051253 A1 | 3/2006 | Gousepohl |
| 2006/0062440 A1 | 3/2006 | Hollars et al. |
| 2006/0090658 A1 | 5/2006 | Phillips |
| 2006/0160134 A1 | 7/2006 | Melker et al. |
| 2007/0243117 A1* | 10/2007 | Wardlaw ............ G01N 1/2813 422/255 |
| 2008/0028962 A1 | 2/2008 | Phillips et al. |
| 2008/0180685 A1 | 7/2008 | de Laga et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0255605 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2013/0065788 A1 | 3/2013 | Glezer et al. |
| 2013/0102018 A1 | 4/2013 | Schentag et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0323330 A1 | 10/2014 | Bergo |
| 2014/0368631 A1 | 12/2014 | Wardlaw et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2016/0350914 A1 | 12/2016 | Champlin et al. |
| 2017/0021356 A1 | 1/2017 | Dority et al. |
| 2017/0038401 A1 | 2/2017 | Holmes et al. |

FOREIGN PATENT DOCUMENTS

| | | |
|---|---|---|
| CN | 1166950 | 9/2004 |
| CN | 1188217 | 2/2005 |
| CN | 1957254 A | 5/2007 |
| CN | 102027369 | 4/2011 |
| EP | 0961110 | 12/1999 |
| EP | 2290100 | 3/2011 |
| EP | 2439515 | 4/2012 |
| EP | 2554987 | 2/2013 |
| EP | 2848196 | 3/2015 |
| EP | 3026433 | 6/2016 |
| WO | 1991020009 | 12/1991 |
| WO | 1999044743 | 9/1999 |
| WO | 1999045385 | 9/1999 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014089468 | 6/2014 |
| WO | 2014183049 | 11/2014 |
| WO | 2014205576 | 12/2014 |
| WO | 2017027643 | 2/2017 |
| WO | 2017048871 | 3/2017 |
| WO | 2017048881 | 3/2017 |

OTHER PUBLICATIONS

Written Opinion for PCT/US2018/017307 established by ISA/US, dated May 1, 2018.

Sun, Wei et al., Rapid antimicrobial susceptibility test for identification of new therapeutics and drug combinations against multidrug-resistant bacteria, Emerg. Microbes Infect., Nov. 9, 2016.

Jahanmehr, S A H et al., Simple technique for fluorescence staining of blood cells with acridine orange, Technical Methods, Feb. 12, 1987.

* cited by examiner

Exemplary device and methods of
collecting exhaled breath condensate (EBC) using a SiEBC
(Single-drop EBC Collector/Analyzer)

1. Exhaling breath onto collection plate

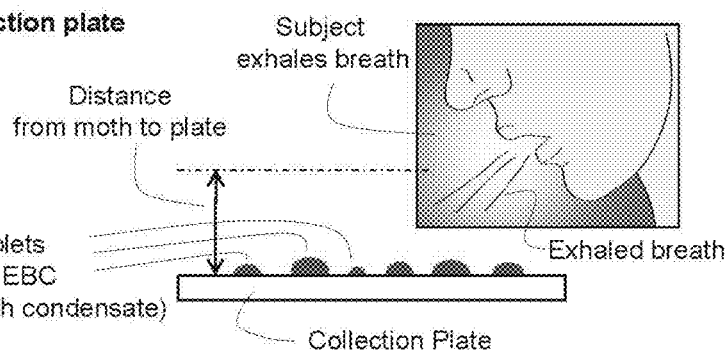

2. Placing cover plate over collection plate and pressing them together

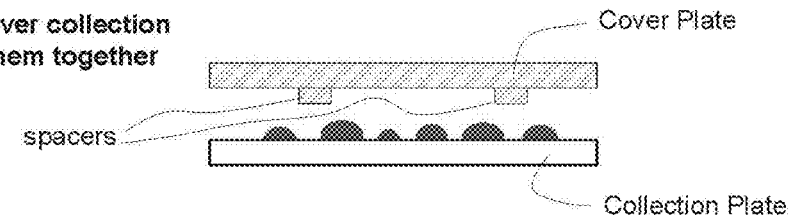

3. Pressing plates into a "Closed-Configuration", where the initial droplets are pressed into a thin layer EBC of a thickness that is regulated by the plates and spacers (not shown).

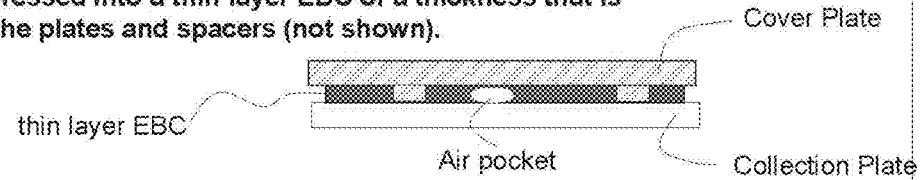

FIG. 9

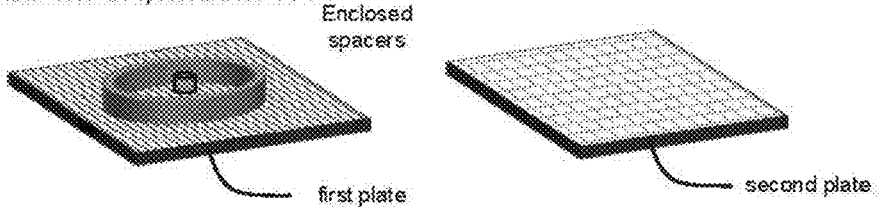
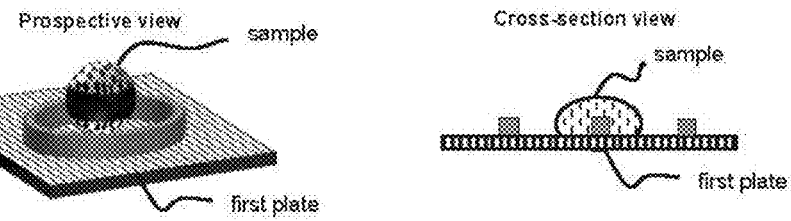
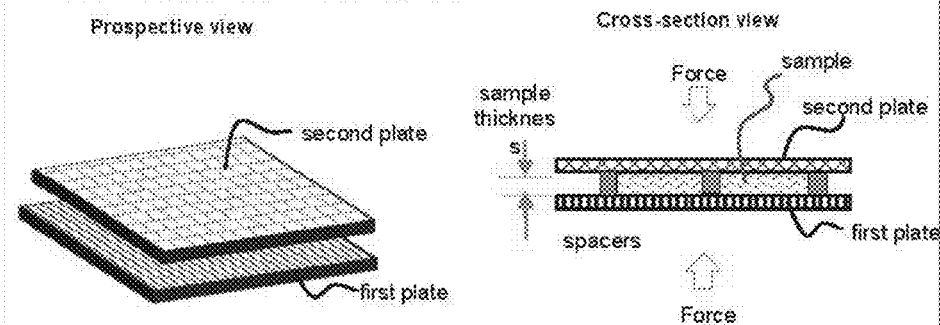
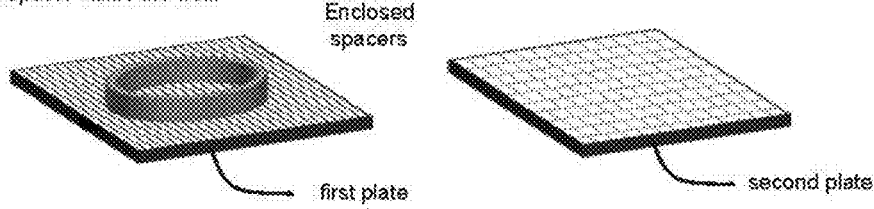
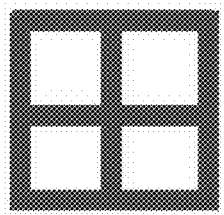
FIG. 10

COMPRESSED OPEN FLOW ASSAY AND USE

CROSS-REFERENCING

This application is a Continuation of U.S. non-Provisional patent application Ser. No. 16/078,316, filed on Aug. 21, 2018, which is a § 371 national stage application of PCT/US2018/017307, filed on Feb. 7, 2018, which claims the benefit of U.S. Provisional Patent Application 62/456,065, filed on Feb. 7, 2017, U.S. Provisional Patent Application 62/456,504, filed on Feb. 8, 2017, U.S. Provisional Patent Application 62/459,972, filed on Feb. 16, 2017, and U.S. Provisional Patent Application 62/460,062, filed on Feb. 16, 2017, each of which applications are incorporated herein in their entireties for all purposes.

FIELD

The present invention is related to the field of bio/chemical sampling, sensing, assays and applications.

BACKGROUND

In biological and chemical assays (e.g. diagnostic testing), often it needs to measure the volume, change the shape, and/or detect analytes of a sample or a part of the sample, quickly and simply, in particularly high sample uniformity, which often leads to high assay accuracy. The current invention provides devices and methods for achieving these goals.

SUMMARY OF INVENTION

The following brief summary is not intended to include all features and aspects of the present invention. The present invention relates to the methods, devices, and systems that make bio/chemical sensing (including, not limited to, immunoassay, nucleic assay, electrolyte analysis, etc.) faster, more sensitive, less steps, easy to perform, smaller amount of samples required, less or reduced (or no) needs for professional assistance, and/or lower cost, than many current sensing methods and devices.

BRIEF DESCRIPTION OF THE DRAWINGS

The skilled artisan will understand that the drawings, described below, are for illustration purposes only. The drawings are not intended to limit the scope of the present teachings in any way. The drawings may not be in scale. In the figures that present experimental data points, the lines that connect the data points are for guiding a viewing of the data only and have no other means.

FIG. 9. An illustration of certain aspects of an exemplary device and methods of collecting exhaled breath condensate (EBC) using a SiEBCA (Single-drop EBC Collector/Analyzer).

FIG. 10 schematically illustrates a SiEBCA with both "open spacer" and "enclosed spacer", where the open spacer is a post (pillar) while the enclosed spacer is a ring spacer or a four-chamber grid spacer. Panel (a) illustrates an embodiment where a first plate has an enclosed spacer and at least one open spacer inside the enclosed spacer. Panel (b) illustrates depositing a sample at the enclosed spacer and the open spacer in an open configuration. Panel (c) illustrates using a second plate to spread the sample and reduce sample thickness. Panel (d) illustrates an embodiment where a first plate does not have an open spacer inside an enclosed spacer. Panel (e) illustrates a top view of an embodiment of an enclosed spacer that has four separate chambers.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Compressed Regulated Open Flow" (CROF)

In assaying, a manipulation of a sample or a reagent can lead to improvements in the assaying. The manipulation includes, but not limited to, manipulating the geometric shape and location of a sample and/or a reagent, a mixing or a binding of a sample and a reagent, and a contact area of a sample of reagent to a plate.

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

Figure 1:
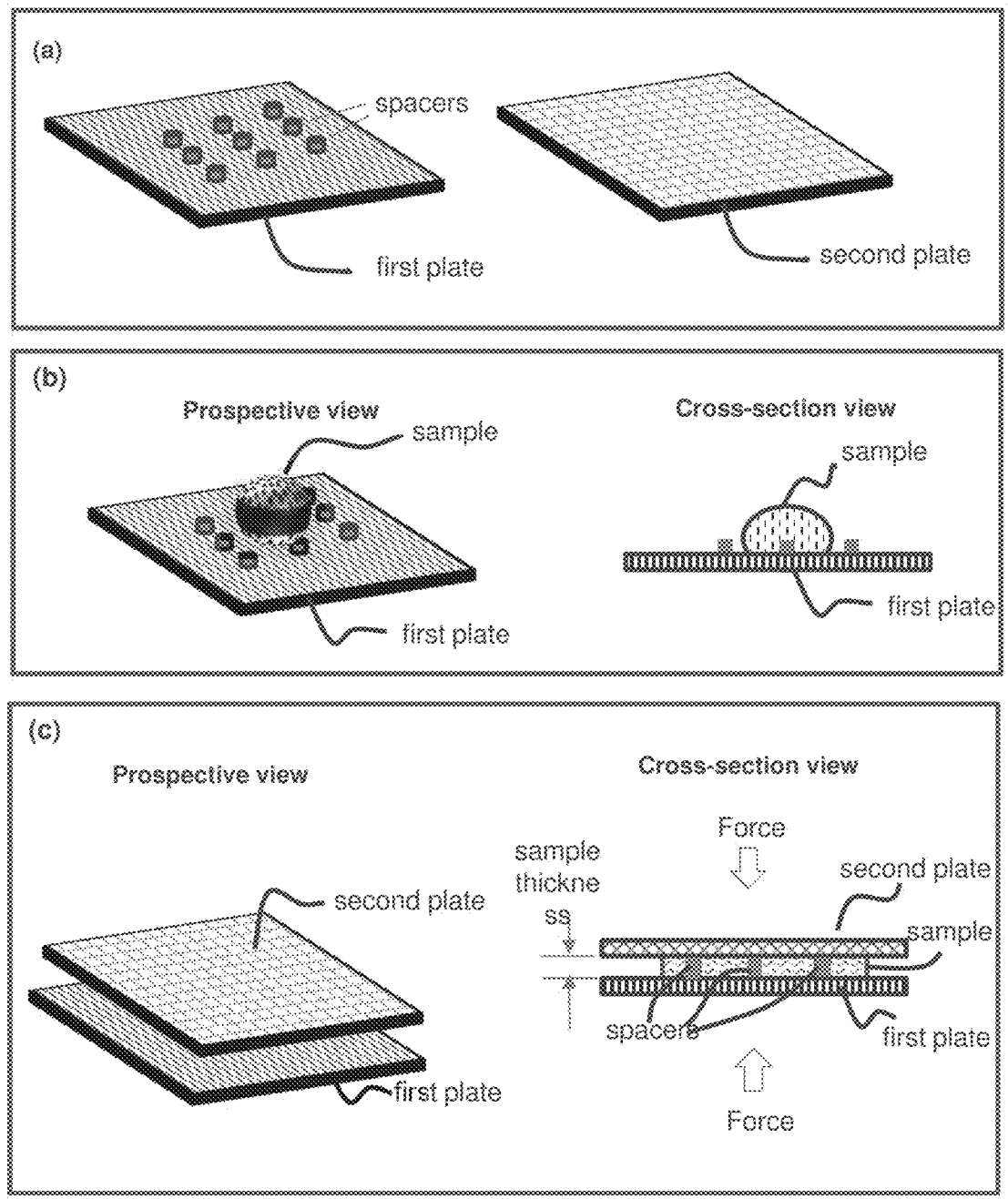
FIG. 1 is an illustration of a CROF(Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).
Figure 2:
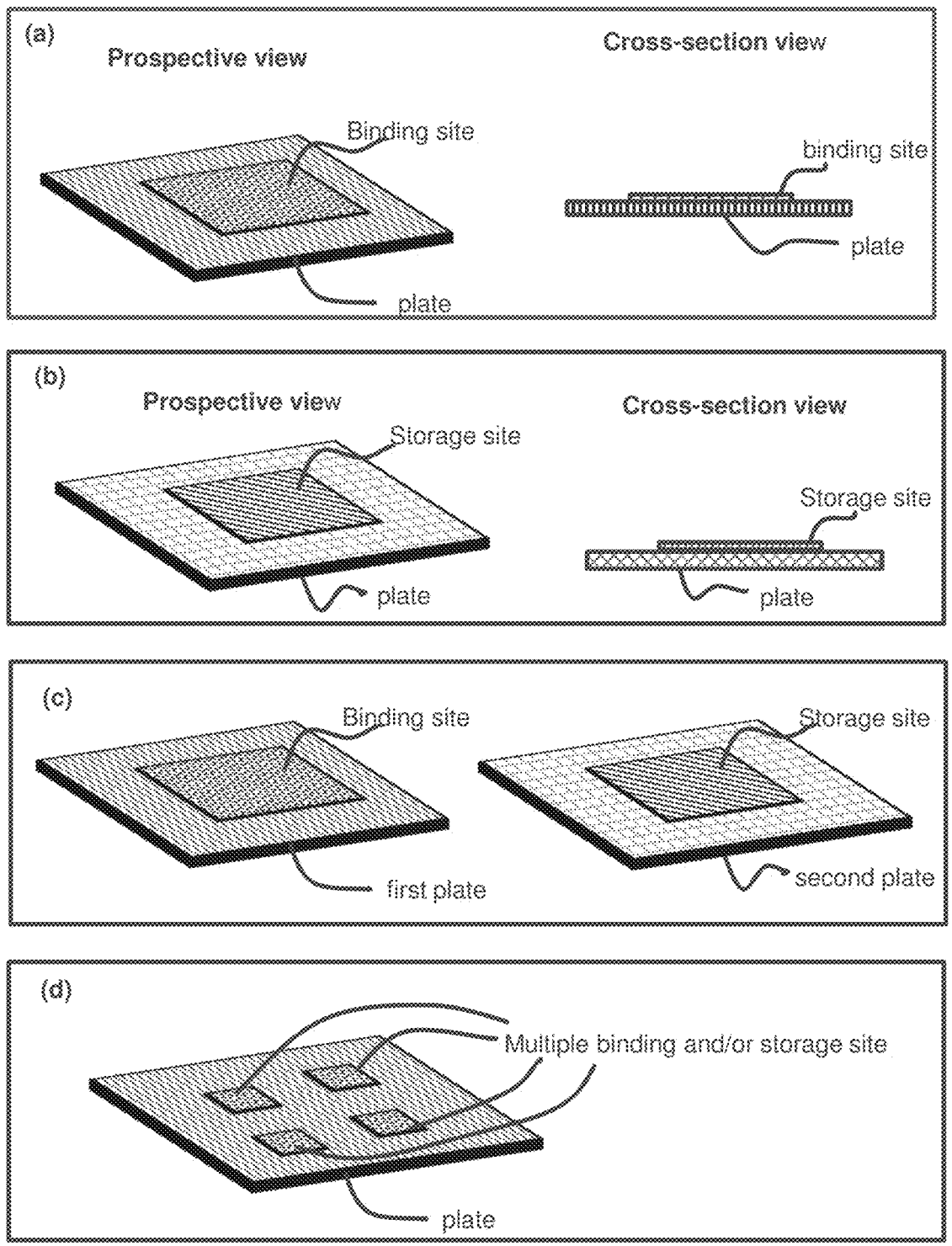
FIG. 2 illustrates plates with a binding site or a storage site. Panel (a) illustrates a plate having a binding site. Panel (b) illustrates a plate having a reagent storage site. Panel (c) illustrates a first plate having a binding site and a second plate having a reagent storage site. Panel (d) illustrates a plate having multiple sites (binding sites and/or storage site).
Figure 3:
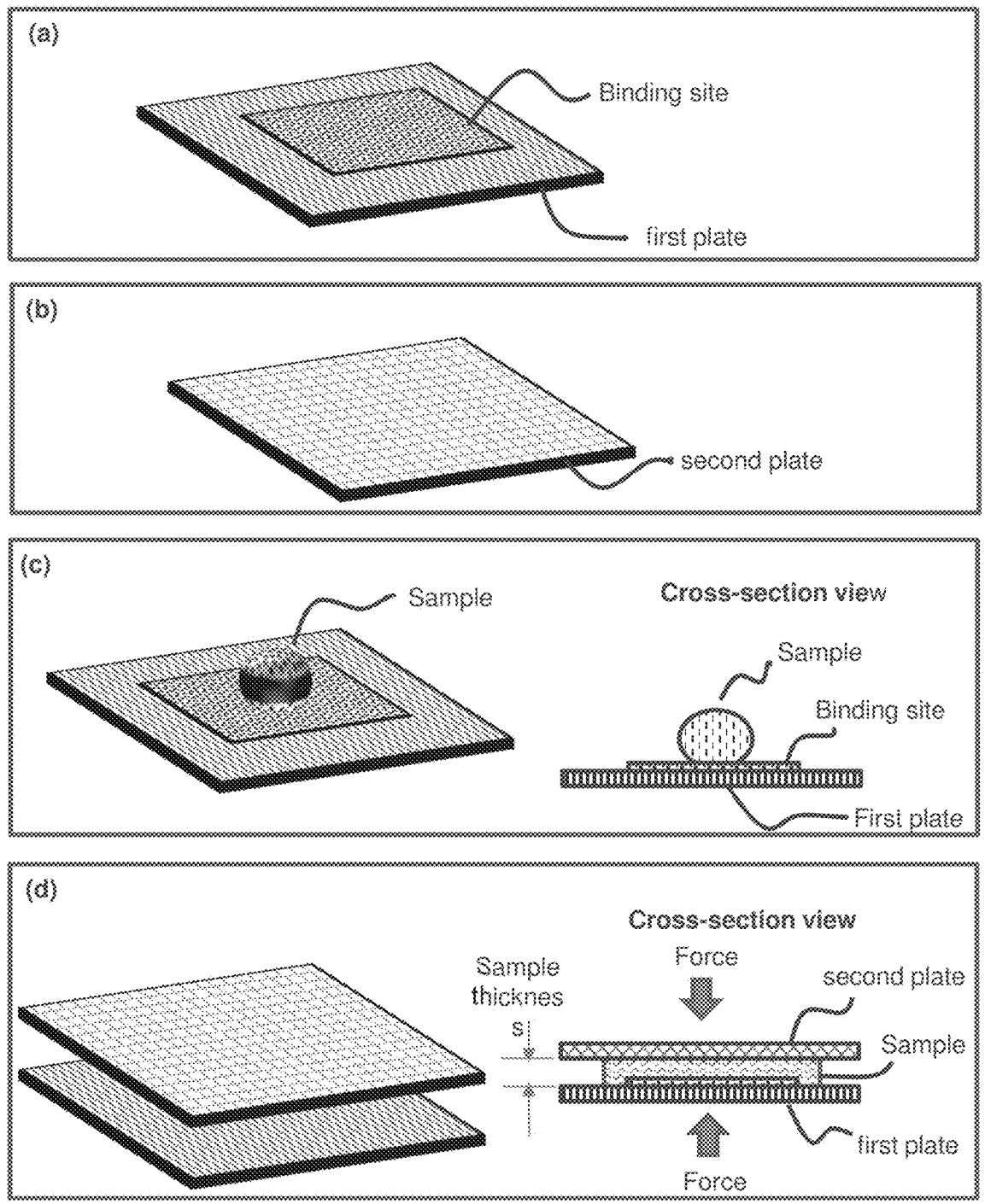
FIG. 3 is a flow-chart and schematic of a method for reducing assay incubation time by reducing sample thickness. Panel (a) illustrates a first plate that has at least one binding site on a substrate surface. Panel (b) illustrates a second plate (which may have a different size from the first plate). Panel (c) illustrates depositing a sample (containing target binding entity) on the substrate surface (shown) or the cover plate (not shown), or both (not shown). Panel (d) illustrates moving the first and second plates so that they are facing each other, and reducing the sample thickness by reducing the spacing of the inner space between the plates. The reduced thickness sample is incubated. The reduced sample thickness speeds up the incubation time. Some embodiment of the method uses spacers to regulate the spacing, which (spacers) are not shown in the illustration.
Figure 4:
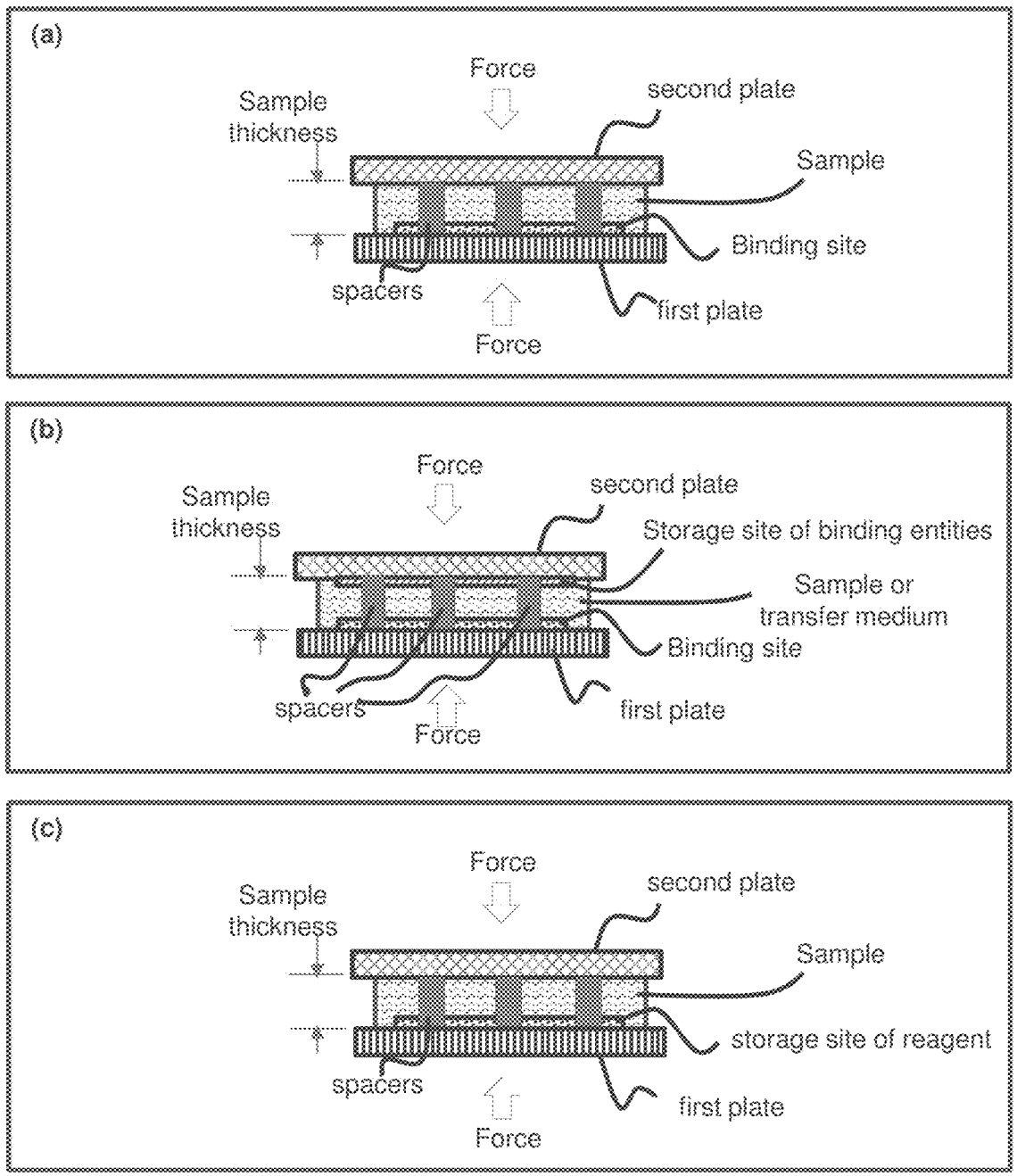
FIG. 4 shows reducing binding or mixing time by reducing the sample thickness using two pates, spacers, and compression (shown in cross-section). Panel (a) illustrates reducing the time for binding entities in a sample to a binding site on a solid surface (X-(Volume to Surface)). Panel (b) illustrates reducing the time for binding entities (e.g. reagent) stored on a surface of plate to a binding site on a surface of another surface (X-(Surface to Surface)). Panel (c) illustrates reducing the time for adding reagents stored on a surface of a plate into a sample that is sandwiched between the plate and other plate (X-(Surface to Volume)).
Figure 5:
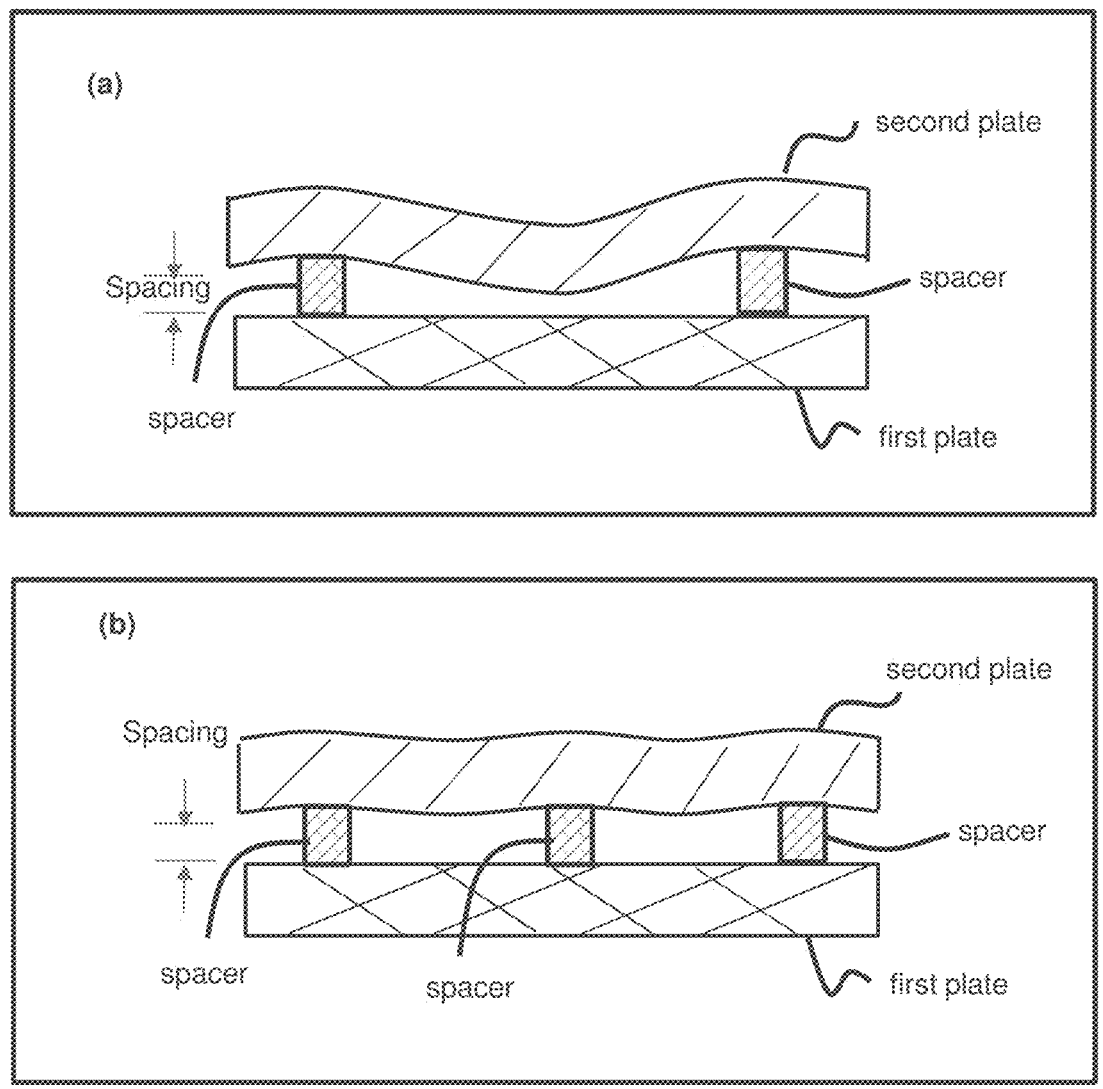
FIG. 5 shows how to avoid or reduce local bending in a flexible plate. Panel (a) illustrates if the inter-spacer distance is too large for a flexible plate (the second plate, e.g. a plastic film) under a given set of sample and compress conditions, the plate has, at the closed configuration, a local sag (i.e. bending inward) between the two neighboring pacers, assuming the first plate is rigid. The sample between the plates is not drawn. Panel (b) illustrates local bending (sag) in a flexible plate in panel (a) is reduced or virtually avoided by using a proper inter-spacer distance and a proper compression force. The sample between the plates is not drawn.
Figure 6:
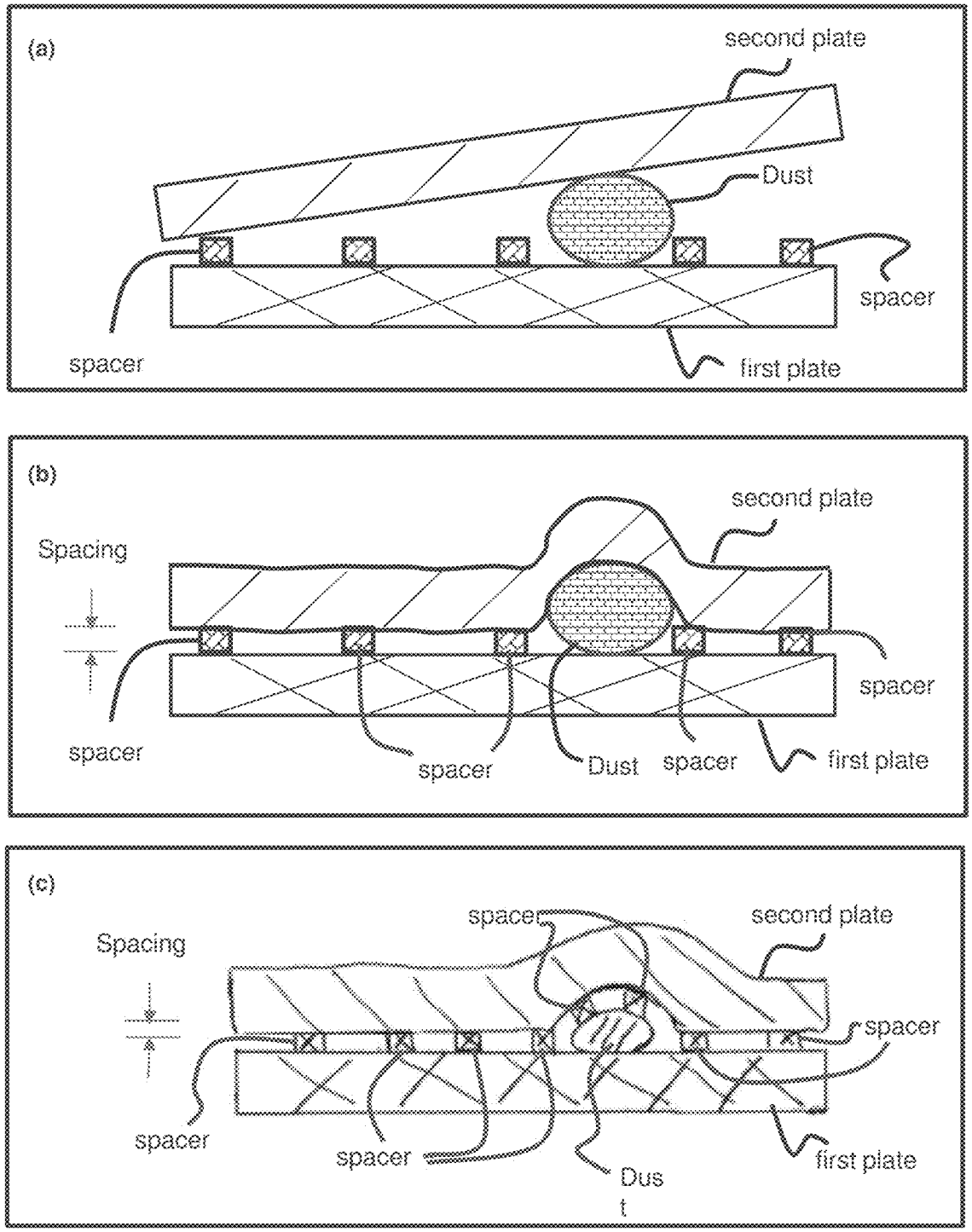
FIG. 6 illustrates reducing effect of large dust on the plate spacing (sample thickness) regulation. Panel (a) illustrates When using two rigid plates, a dust with a thickness larger than a spacer height can destroy an intended plate spacing regulation by the spacers (hence destroy the intended sample thickness regulation). The sample between the plates is not drawn. Panel (b) illustrates using a proper flexible plate and a proper inter-spacer distance, the effect of a dust is isolated to a small area around dust, while in other areas, the plate spacing (hence the sample thickness) is regulated by the spacers not the dust. This illustration has the first plate is rigid, the second plate is flexible, and the spacers are initially fixed on the first plate. Panel (c) illustrates an illustration of using a proper flexible plate and a proper inter-spacer distance, the effect of a dust is isolated to a small area around dust, while in other areas, the plate spacing (hence the sample thickness) is regulated by the spacers not the dust. This illustration has the first plate is rigid, the second plate is flexible, and the spacers are initially fixed on the second plate.
Figure 7:
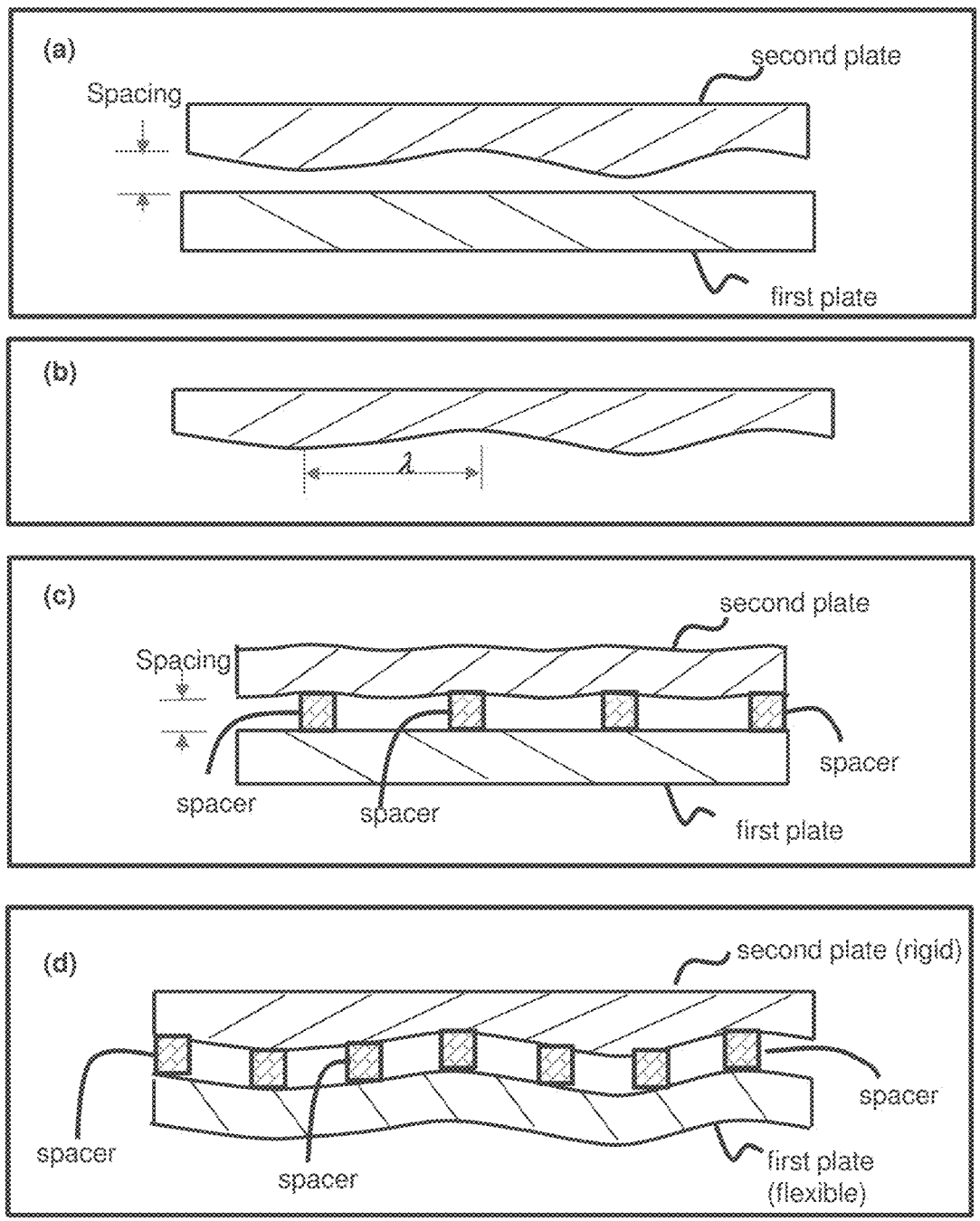
FIG. 7 illustrates reducing effects of surface flatness variation of plate by using proper spacer arrangement and flexible plate(s). Panel (a) shows that surface flatness variation can be significantly large compared with a desired sample thickness, causing errors in determining a sample thickness. In this illustration, only one plate has a large flatness variation (in reality, both plates may have large flatness variation). The sample between the plates is not drawn. Panel (b) illustrates a surface flatness variation distance of a plate, □□, is the distance from a local maximum to a neighboring local minimum of a surface height. Panel (c) illustrates how a small surface flatness variation can be achieved by making one or both plate flexible and using a proper inter-spacer distance and proper compressing force to correct, at the closed configuration, the original surface flatness variation of the plate when they are at open configuration. The sample between the plates is not drawn. Panel (d) illustrates making the sample thickness variation less than the initial surface flatness variation of the plate by using a flexible second plate and a proper inter spacer distance. The flexible plate follows the contour of the rigid plate. The sample between the plates is not drawn.
Figure 8:
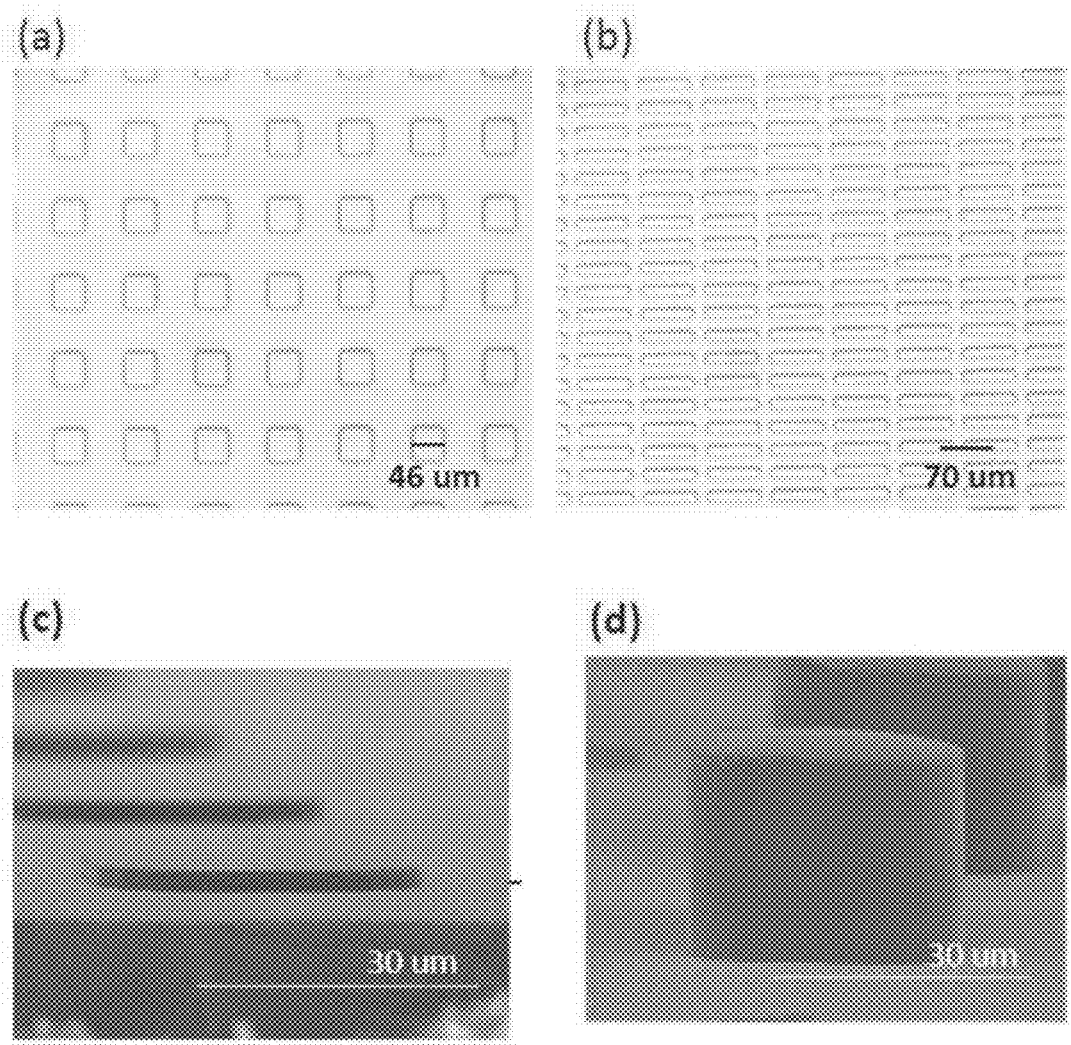
FIG. 8 Spacers on a plate. Top view of photograph of (a) 46 um×46 um pillar spacer size and 54 um inter pillar distance, and (b) 10 um×70 um pillar spacer size and 10 um pillar distance; and prospect view SEM of (c) 30 um×40 um pillar spacer size of 2 um spacer height, and (d) 30 um×40 um pillar spacer size of 30 um spacer height.

One embodiment of the method of CROF, as illustrated in FIG. 1, comprises:
  (a) obtaining a sample, that is flowable;
  (b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;
  (c) depositing, when the plates are configured in an open configuration, the sample on one or both of the plates; wherein the open configuration is a configuration in which the two plates are either partially or completely separated apart and the spacing between the plates is not regulated by the spacers; and
  (d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process.

The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 um. The surface flatness variation is different from the surface smoothness. A planar surface can have a good surface smoothness, but poor surface flatness (i.e. large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 um, it means that the spacer height is equal to or less than 1 um.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "plate-spacing" refers to the distance between the inner surfaces of the two plates.

The term "deviation of the final sample thickness" in a CROF means the difference between the predetermined spacer height (determined from fabrication of the spacer) and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 um for a given flexible plate, sample, and compression force, the bending of the plate between two neighboring spacers 40 um apart will be 50 nm, and the bending will be less than 50 nm if the two neighboring spacers is less than 40 um.

The term "flowable" for a sample means that when the thickness of the sample is reduced, the lateral dimension increases. For an example, a stool sample is regarded flowable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017, which is incorporated herein in its entirety for all purposes.

Examples of Present Invention

I. Formation of Uniform Thin Fluidic Layer by an Imprecise Force Pressing

The term "imprecise pressing force" without adding the details and then adding a definition for imprecise pressing force.

As used herein, the term "imprecise" in the context of a force (e.g. "imprecise pressing force") refers to a force that (a) has a magnitude that is not precisely known or precisely predictable at the time the force is applied;

(b) has a magnitude in the range of 1N to 20N and/or a pressure in a range of 0.1 psi to 280 psi;

(c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

A. Imprecise Force, Specify IGS^4/hE

A1. A device for forming a thin fluidic sample layer with a uniform predetermined thickness by pressing with an imprecise pressing force, comprising:

a first plate, a second plate, and spacers, wherein:
i. the plates are movable relative to each other into different configurations;
ii. one or both plates are flexible;
iii. each of the plates comprises an inner surface that has a sample contact area for contacting a fluidic sample;
iv. each of the plates comprises, on its respective outer surface, a force area for applying an imprecise pressing force that forces the plates together;
v. one or both of the plates comprise the spacers that are permanently fixed on the inner surface of a respective plate;
vi. the spacers have a predetermined substantially uniform height that is equal to or less than 200 microns, and a predetermined fixed inter-spacer-distance;
vii. the fourth power of the inter-spacer-distance (IDS) divided by the thickness (h) and the Young's modulus (E) of the flexible plate ($ISD^4/(hE)$) is $5 \times 10^6$ $um^3/GPa$ or less; and
viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A2. A method of forming a thin fluidic sample layer with a uniform predetermined thickness by pressing with an imprecise pressing force, comprising the steps of:
  (a) obtaining a first plate, a second plate, and spacers, wherein:
    i. the plates are movable relative to each other into different configurations;
    ii. one or both plates are flexible;
    iii. each of the plates comprises an inner surface that has a sample contact area for contacting a fluidic sample;
    iv. each of the plates comprises, on its respective outer surface, a force area for applying an imprecise pressing force that forces the plates together;
    v. one or both of the plates comprise the spacers that are permanently fixed on the inner surface of a respective plate;
    vi. the spacers have a predetermined substantially uniform height that is equal to or less than 200 microns, and a predetermined fixed inter-spacer-distance;
    vii. the fourth power of the inter-spacer-distance (IDS) divided by the thickness (h) and the Young's modulus (E) of the flexible plate ($ISD^4/(hE)$) is $5 \times 10^6$ $um^3/GPa$ or less; and
    viii. at least one of the spacers is inside the sample contact area;
  (b) obtaining a fluidic sample;
  (c) depositing the sample on one or both of the plates; when the plates are configured in an open configuration, wherein the open configuration is a configuration in which the two plates are partially or completely separated apart and the spacing between the plates is not regulated by the spacers;
  (d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
    bringing the two plates together; and
    conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
    wherein the force that presses the two plates into the closed configuration is an imprecise pressing force provided by human hand.

B. Hand pressing, Specify Spacer Hardness-Contact Area Product

B1. A device for forming a thin fluidic sample layer with a uniform predetermined thickness by pressing with an imprecise force, comprising:
  a first plate, a second plate, and spacers, wherein:
    i. the plates are movable relative to each other into different configurations;
    ii. one or both plates are flexible;
    iii. each of the plates comprises, on its respective inner surface, a sample contact area for contacting and/or compressing a fluidic sample;
    iv. each of the plates comprises, on its respective outer surface, an area for applying a force that forces the plates together;
    v. one or both of the plates comprise the spacers that are permanently fixed on the inner surface of a respective plate;
    vi. the spacers have a predetermined substantially uniform height that is equal to or less than 200 microns, a predetermined width, and a predetermined inter-spacer-distance;
    vii. a ratio of the inter-spacer-distance to the spacer width is 1.5 or larger; and
    viii. at least one of the spacers is inside the sample contact area;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and
  wherein the force that presses the two plates into the closed configuration is an imprecise pressing force provided by human hand.

B2. A method of forming a thin fluidic sample layer with a uniform predetermined thickness by pressing with an imprecise pressing force, comprising the steps of:
  (a) obtaining a first plate, a second plate, and spacers, wherein:
    i. the plates are movable relative to each other into different configurations;
    ii. one or both plates are flexible;
    iii. each of the plates comprises, on its respective inner surface, a sample contact area for contacting and/or compressing a fluidic sample;
    iv. each of the plates comprises, on its respective outer surface, an area for applying a force that forces the plates together;
    v. one or both of the plates comprise the spacers that are permanently fixed on the inner surface of a respective plate;
    vi. the spacers have a predetermined substantially uniform height that is equal to or less than 200 microns, a predetermined width, and a predetermined inter-spacer-distance;
    vii. a ratio of the inter-spacer-distance to the spacer width is 1.5 or larger; and
    viii. at least one of the spacers is inside the sample contact area;
  (b) obtaining a fluidic sample;
  (c) depositing the sample on one or both of the plates; when the plates are configured in an open configuration, wherein the open configuration is a configuration in which the two plates are partially or completely separated apart and the spacing between the plates is not regulated by the spacers;

(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:

bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and wherein the force that presses the two plates into the closed configuration is an imprecise pressing force provided by human hand.

C. Hand pressing, Specify IDS/hE & Spacer Hardness-Contact Area Product

C1. A device for forming a thin fluidic sample layer with a uniform predetermined thickness by pressing with an imprecise force, comprising:

a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger; and
  viii. at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the force that presses the two plates into the closed configuration is imprecise, and is provided by human hand.

C2. A method of forming a thin fluidic sample layer with a uniform predetermined thickness by pressing with an imprecise pressing force, comprising the steps of:

(a) obtaining a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;
  iv. each of the plates comprises, on its respective outer surface, an area for applying a force that forces the plates together;
  v. one or both of the plates comprise the spacers that are permanently fixed on the inner surface of a respective plate;
  vi. the spacers have a predetermined substantially uniform height that is equal to or less than 200 microns, a predetermined width, and a predetermined inter-spacer-distance;
  vii. a ratio of the inter-spacer-distance to the spacer width is 1.5 or larger; and
  viii. at least one of the spacers is inside the sample contact area;

(b) obtaining a fluidic sample;

(c) depositing the sample on one or both of the plates; when the plates are configured in an open configuration, wherein the open configuration is a configuration in which the two plates are partially or completely separated apart and the spacing between the plates is not regulated by the spacers;

(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:

bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and wherein the force that presses the two plates into the closed configuration is an imprecise pressing force provided by human hand.

D. Hand pressing, Specify Pillar Spacer and Ratio of IDS/W

D1. A device for forming a thin fluidic sample layer with a uniform predetermined thickness by pressing with an imprecise force, comprising:

a first plate, a second plate, and spacers, wherein:
  i. the plates are movable relative to each other into different configurations;
  ii. one or both plates are flexible;
  iii. each of the plates comprises, on its respective inner surface, a sample contact area for contacting and/or compressing a fluidic sample;

iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined inter-spacer-distance;
vii. a ratio of the inter-spacer-distance to the spacer width is 1.5 or larger.
viii. at least one of the spacers is inside the sample contact area; and wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the force that presses the two plates into the closed configuration is imprecise, and is provided by human hand.

D2. A method of forming a thin fluidic sample layer with a uniform predetermined thickness by pressing with an imprecise pressing force, comprising the steps of:
(a) obtaining a first plate, a second plate, and spacers, wherein:
   i. the plates are movable relative to each other into different configurations;
   ii. one or both plates are flexible;
   iii. each of the plates comprises, on its respective inner surface, a sample contact area for contacting and/or compressing a fluidic sample;
   iv. each of the plates comprises, on its respective outer surface, an area for applying a force that forces the plates together;
   v. one or both of the plates comprise the spacers that are permanently fixed on the inner surface of a respective plate;
   vi. the spacers have a predetermined substantially uniform height that is equal to or less than 200 microns, a predetermined width, and a predetermined inter-spacer-distance;
   vii. a ratio of the inter-spacer-distance to the spacer width is 1.5 or larger.
   viii. at least one of the spacers is inside the sample contact area; and
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
   bringing the two plates together; and
   conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
   wherein the force that presses the two plates into the closed configuration is an imprecise pressing force provided by human hand.

E. Q (V-1) Volume Determination, Specify IGS^4/hE

E1. A device for determining a relevant sample volume by pressing with an imprecise force provided by human hand, comprising:
a first plate, a second plate, spacers, and an area-determination device, wherein:
   i. the plates are movable relative to each other into different configurations;
   ii. one or both plates are flexible;
   iii. each of the plates comprises, on its respective inner surface, a sample contact area for contacting and/or compressing a fluidic sample that has a relevant volume to be measured;
   iv. each of the plates comprises, on its respective outer surface, an area for applying a force that forces the plates together;
   v. one or both of the plates comprise the spacers that are permanently fixed on the inner surface of a respective plate;
   vi. the spacers have a predetermined substantially uniform height that is equal to or less than 200 microns, and a predetermined constant inter-spacer-distance;
   vii. a fourth power of the inter-spacer-distance (IDS) divided by the thickness (h) and the Young's modulus (E) of the flexible plate ($ISD^4/(hE)$) is $5 \times 10^6$ um$^3$/GPa or less.
   viii. at least one of the spacers is inside the sample contact area; and
   ix. the area-determination device is configured to determine the lateral area of the relevant volume;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;

wherein the relevant volume of the sample is a partial or entire volume of the uniform thickness layer and the value of the relevant volume is determined by the uniform thickness and the determined lateral area; and
wherein the force that presses the two plates into the closed configuration is imprecise, and is provided by human hand.

The device of any prior embodiment, wherein the area-determination device is a camera.

The area-determination device comprises an area in the sample contact area of a plate, wherein the area is less than 1/100, 1/20, 1/10, 1/6, 1/5, 1/4, 1/3, 1/2, 2/3 of the sample contact area, or in a range between any of the two values.

The area-determination device comprises a camera and an area in the sample contact area of a plate, wherein the area is in contact with the sample.

E2. A method of forming a thin fluidic sample layer with a uniform predetermined thickness by pressing with an imprecise pressing force, comprising the steps of:
  (a) obtaining a first plate, a second plate, and spacers, wherein:
    i. the plates are movable relative to each other into different configurations;
    ii. one or both plates are flexible;
    iii. each of the plates comprises, on its respective inner surface, a sample contact area for contacting and/or compressing a fluidic sample that has a relevant volume to be measured;
    iv. each of the plates comprises, on its respective outer surface, an area for applying a force that forces the plates together;
    v. one or both of the plates comprise the spacers that are permanently fixed on the inner surface of a respective plate;
    vi. the spacers have a predetermined substantially uniform height that is equal to or less than 200 microns, and a predetermined constant inter-spacer-distance;
    vii. a fourth power of the inter-spacer-distance (IDS) divided by the thickness (h) and the Young's modulus (E) of the flexible plate ($ISD^4/(hE)$) is $5 \times 10^6$ $um^3/GPa$ or less.
    viii. at least one of the spacers is inside the sample contact area; and
    ix. the area-determination device is configured to determine the lateral area of the relevant volume;
  (b) obtaining a fluidic sample;
  (c) depositing the sample on one or both of the plates; when the plates are configured in an open configuration, wherein the open configuration is a configuration in which the two plates are partially or completely separated apart and the spacing between the plates is not regulated by the spacers;
  (d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
    bringing the two plates together; and
    conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
wherein the force that presses the two plates into the closed configuration is an imprecise pressing force provided by human hand.

F. Q (V-1) Volume Determination, Specify $IGS^4/hE$

F1. A device for determining a relevant sample volume by pressing with an imprecise force provided by human hand, comprising:
  a first plate, a second plate, spacers, and area-determination device, wherein:
    i. the plates are movable relative to each other into different configurations;
    ii. one or both plates are flexible;
    iii. each of the plates comprises, on its respective inner surface, a sample contact area for contacting and/or compressing a fluidic sample that has a relevant volume to be measured;
    iv. each of the plates comprises, on its respective outer surface, an area for applying a force that forces the plates together;
    v. one or both of the plates comprise the spacers that are permanently fixed on the inner surface of a respective plate;
    vi. the spacers have a predetermined substantially uniform height that is equal to or less than 200 microns, and a predetermined constant inter-spacer-distance;
    vii. a fourth power of the inter-spacer-distance (IDS) divided by the thickness (h) and the Young's modulus (E) of the flexible plate ($ISD^4/(hE)$) is $5 \times 10^6$ $um^3/GPa$ or less.
    viii. at least one of the spacers is inside the sample contact area; and
    ix. the area-determination device is configured to determine the lateral area of the relevant volume;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers;
  wherein the relevant volume of the sample is a partial or entire volume of the uniform thickness layer and the value of the relevant volume is determined by the uniform thickness and the determined lateral area; and
  wherein the force that presses the two plates into the closed configuration is imprecise, and is provided by human hand.

F2. A method of forming a thin fluidic sample layer with a uniform predetermined thickness by pressing with an imprecise pressing force, comprising the steps of:
  (a) obtaining a first plate, a second plate, and spacers, wherein:
    i. the plates are movable relative to each other into different configurations;
    ii. one or both plates are flexible;

iii. each of the plates comprises, on its respective inner surface, a sample contact area for contacting and/or compressing a fluidic sample that has a relevant volume to be measured;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, and a predetermined constant inter-spacer-distance;
vii. a fourth power of the inter-spacer-distance (IDS) divided by the thickness (h) and the Young's modulus (E) of the flexible plate (ISD$^4$/(hE)) is 5×10$^6$ um$^3$/GPa or less.
viii. at least one of the spacers is inside the sample contact area; and
ix. the area-determination device is configured to determine the lateral area of the relevant volume;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), using the two plates to compress at least part of the sample into a layer of substantially uniform thickness that is confined by the sample contact surfaces of the plates, wherein the uniform thickness of the layer is regulated by the spacers and the plates, wherein the compressing comprises:
bringing the two plates together; and
conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample, and
wherein the force that presses the two plates into the closed configuration is an imprecise pressing force provided by human hand.

1. The device or method of any prior embodiment, wherein spacers have a flat top.
2. The device or method of any prior embodiment, wherein the device is further configured to have, after the pressing force is removed, a sample thickness that is substantially the same in thickness and uniformity as that when the force is applied.
3. The device or method of any prior embodiment, wherein the imprecise force is provided by human hand.
4. The device or method of any prior embodiment, wherein the inter spacer distance is substantially constant.
5. The device or method of any prior embodiment, wherein the inter spacer distance is substantially periodic in the area of the uniform sample thickness area.
6. The device or method of any prior embodiment, wherein the multiplication product of the filling factor and the Young's modulus of the spacer is 2 MPa or larger.
7. The device or method of any prior embodiment, wherein the force is applied by hand directly or indirectly.
8. The device or method of any prior embodiment, wherein the force applied is in the range of 5 N to 20 N.
9. The device or method of any prior embodiment wherein the highly uniform layer has a thickness that varies by less than 15%, 10%, or 5% of an average thickness.
10. The device or method of any prior embodiment, wherein the imprecise force is applied by pinching the device between a thumb and forefinger.
11. The device or method of any prior embodiment, wherein the predetermined sample thickness is larger than the spacer height.
12. The device or method of any prior embodiment, wherein the device holds itself in the closed configuration after the pressing force has been removed.
13. The device or method of any prior embodiment, wherein the uniform thickness sample layer area is larger than that area upon which the pressing force is applied.
14. The device or method of any prior embodiment, wherein the spacers do not significantly deform during application of the pressing force.
15. The device or method of any prior embodiment, wherein the pressing force is not predetermined beforehand and is not measured.
16. The device of any prior device embodiment, wherein the analyte comprises a molecule (e.g., a protein, peptides, DNA, RNA, nucleic acid, or other molecule), cells, tissues, viruses, and nanoparticles with different shapes.
17. The device of any prior device embodiment, wherein the analyte comprises white blood cells, red blood cells and platelets.
18. The device of any prior device embodiment, wherein the analyte is stained.
19. The method or device of any prior embodiment, wherein the inter spacer distance (SD) is equal or less than about 120 um (micrometer).
20. The method or device of any prior embodiment, wherein the inter spacer distance (SD) is equal or less than about 100 um (micrometer).
21. The method or device of any prior embodiment, wherein the fourth power of the inter-spacer-distance (ISD) divided by the thickness (h) and the Young's modulus (E) of the flexible plate (ISD$^4$/(hE)) is 5×10$^6$ um$^3$/GPa or less.
22. The method or device of any prior embodiment, wherein the fourth power of the inter-spacer-distance (ISD) divided by the thickness (h) and the Young's modulus (E) of the flexible plate (ISD$^4$/(hE)) is 5×10$^5$ um$^3$/GPa or less.
23. The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).
24. The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

25. The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.
26. The method or device of any prior embodiment, wherein the analytes is the analyte in 5 detection of proteins, peptides, nucleic acids, synthetic compounds, and inorganic compounds.
27. The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
28. The method or device of any prior embodiment, wherein the spacers have a shape of pillars and a ratio of the width to the height of the pillar is equal or larger than one.
29. The method of any prior embodiment, wherein the sample that is deposited on one or both of the plates has an unknown volume.
30. The method or device of any prior embodiment, wherein the samples is for the detection, purification and quantification of chemical compounds or biomolecules that correlates with the stage of certain diseases.
31. The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.
32. The method or device of any prior embodiment, wherein the samples is related to the detection, purification and quantification of microorganism.
33. The method or device of any prior embodiment, wherein the samples is related to virus, fungus and bacteria from environment, e.g., water, soil, or biological samples.
34. The method or device of any prior embodiment, wherein the samples is related to the detection, quantification of chemical compounds or biological samples that pose hazard to food safety or national security, e.g. toxic waste, anthrax.
35. The method or device of any prior embodiment, wherein the samples is related to quantification of vital parameters in medical or physiological monitor.
36. The method or device of any prior embodiment, wherein the samples is related to glucose, blood, oxygen level, total blood count.
37. The method or device of any prior embodiment, wherein the samples is related to the detection and quantification of specific DNA or RNA from biosamples.
38. The method or device of any prior embodiment, wherein the samples is related to the sequencing and comparing of genetic sequences in DNA in the chromosomes and mitochondria for genome analysis.
39. The method or device of any prior embodiment, wherein the samples is related to detect reaction products, e.g., during synthesis or purification of pharmaceuticals.
40. The method or device of any prior embodiment, wherein the samples is cells, tissues, bodily fluids, and stool.
41. The method or device of any prior embodiment, wherein the sample is the sample in the detection of proteins, peptides, nucleic acids, synthetic compounds, inorganic compounds.
42. The method or device of any prior embodiment, wherein the sample is the sample in the fields of human, veterinary, agriculture, foods, environments, and drug testing.
43. The method or device of any prior embodiment, wherein the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, throat swab, stool samples, hair, finger nail, ear wax, breath, connective tissue, muscle tissue, nervous tissue, epithelial tissue, cartilage, cancerous sample, or bone.
44. The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%,5%,7%,10%, 15%, 20%, 30%,40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm$^2$ (centimeter square) to 100 kg/cm$^2$, (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

IDS^4/hE

A1. A device for forming a thin fluidic sample layer with a uniform predetermined thickness by pressing, comprising:
  a first plate, a second plate, and spacers, wherein:
    ix. the plates are movable relative to each other into different configurations;
    x. one or both plates are flexible;
    xi. each of the plates comprises an inner surface that has a sample contact area for contacting a fluidic sample;
    xii. each of the plates comprises, on its respective outer surface, a force area for applying an pressing force that forces the plates together;
    xiii. one or both of the plates comprise the spacers that are permanently fixed on the inner surface of a respective plate;
    xiv. the spacers have a predetermined substantially uniform height that is equal to or less than 200 microns, and a predetermined fixed inter-spacer-distance;
    xv. the fourth power of the inter-spacer-distance (ISD) divided by the thickness (h) and the Young's modulus (E) of the flexible plate (ISD$^4$/(hE)) is 5×10$^6$ um$^3$/GPa or less; and
    xvi. at least one of the spacers is inside the sample contact area;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample is deposited in the open configuration and the plates are forced to the closed configuration by applying the pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A2. A method of forming a thin fluidic sample layer with a uniform predetermined thickness by pressing, comprising the steps of:
  (e) obtaining a device of embodiment A1;
  (f) depositing a fluidic sample on one or both of the plates; when the plates are configured in an open configuration, wherein the open configuration is a configuration in which the two plates are partially or completely separated apart and the spacing between the plates is not regulated by the spacers;
  (g) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A3. A device for analyzing a fluidic sample, comprising:
  a first plate, a second plate, and spacers, wherein:
    i. the plates are movable relative to each other into different configurations;
    ii. one or both plates are flexible;
    iii. each of the plates has, on its respective inner surface, a sample contact area for contacting a fluidic sample,
    iv. one or both of the plates comprise the spacers and the spacers are fixed on the inner surface of a respective plate;
    v. the spacers have a predetermined substantially uniform height that is equal to or less than 200 microns, and the inter-spacer-distance is predetermined;
    vi. the Young's modulus of the spacers multiplied by the filling factor of the spacers is at least 2 MPa; and
    vii. at least one of the spacers is inside the sample contact area; and
  wherein one of the configurations is an open configuration, in which: the two plates are partially or completely separated apart, the spacing between the plates is not regulated by the spacers, and the sample is deposited on one or both of the plates; and
  wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

A4. A method of forming a thin fluidic sample layer with a uniform predetermined thickness by pressing, comprising the steps of:

(a) obtaining a device of embodiment A3;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A5. A device for analyzing a fluidic sample, comprising:
a first plate and a second plate, wherein:
  i. the plates are movable relative to each other into different configurations;
  ii. one or both plates are flexible;
  iii. each of the plates has, on its respective surface, a sample contact area for contacting a sample that contains an analyte,
  iv. one or both of the plates comprise spacers that are permanently fixed to a plate within a sample contact area, wherein the spacers have a predetermined substantially uniform height and a predetermined fixed inter-spacer distance that is at least about 2 times larger than the size of the analyte, up to 200 um, and wherein at least one of the spacers is inside the sample contact area;
  wherein one of the configurations is an open configuration, in which: the two plates are separated apart, the spacing between the plates is not regulated by the spacers, and the sample is deposited on one or both of the plates; and
  wherein another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

A6. A method of forming a thin fluidic sample layer with a uniform predetermined thickness by pressing, comprising the steps of:
(a) obtaining a device of embodiment A5;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A7. A device for forming a thin fluidic sample layer with a uniform predetermined thickness by pressing, comprising:
a first plate, a second plate, and spacers, wherein:
  ix. the plates are movable relative to each other into different configurations;
  x. one or both plates are flexible;
  xi. each of the plates comprises, on its respective inner surface, a sample contact area for contacting and/or compressing a fluidic sample;
  xii. each of the plates comprises, on its respective outer surface, an area for applying a force that forces the plates together;
  xiii. one or both of the plates comprise the spacers that are permanently fixed on the inner surface of a respective plate;
  xiv. the spacers have a predetermined substantially uniform height that is equal to or less than 200 microns, a predetermined width, and a predetermined fixed inter-spacer-distance;
  xv. a ratio of the inter-spacer-distance to the spacer width is 1.5 or larger; and
  xvi. at least one of the spacers is inside the sample contact area;
  wherein one of the configurations is an open configuration, in which: the two plates are partially or completely separated apart, the spacing between the plates is not regulated by the spacers, and the sample is deposited on one or both of the plates;
  wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A8. A method of forming a thin fluidic sample layer with a uniform predetermined thickness by pressing with an imprecise pressing force, comprising the steps of:
(a) obtaining a device of embodiment A7;
(b) obtaining a fluidic sample;
(e) depositing the sample on one or both of the plates; when the plates are configured in an open configuration, wherein the open configuration is a configuration in which the two plates are partially or completely separated apart and the spacing between the plates is not regulated by the spacers;
(d) after (c), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

The devices or methods of any prior embodiment, wherein the spacers have a shape of pillar with a foot fixed on one of the plate and a flat top surface for contacting the other plate.

The devices or methods of any prior embodiment, wherein the spacers have a shape of pillar with a foot fixed on one of the plate, a flat top surface for contacting the other plate, substantially uniform cross-section.

The devices or methods of any prior embodiment, wherein the spacers have a shape of pillar with a foot fixed on one of the plate and a flat top surface for contacting the other plate, wherein the flat top surface of the pillars has a variation in less than 10 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 50 nm.

The devices or methods of any prior embodiment, wherein the spacers have a shape of pillar with a foot fixed on one of the plate and a flat top surface for contacting the other plate, wherein the flat top surface of the pillars has a variation in less than 10 nm, 20 nm, 30 nm, 100 nm, 200 nm, or in a range of any two of the values.

The devices or methods of any prior embodiment, wherein the Young's modulus of the spacers multiplied by the filling factor of the spacers is at least 2 MPa.

The devices or methods of any prior embodiment, wherein the sample comprises an analyte and the predetermined constant inter-spacer distance is at least about 2 times larger than the size of the analyte, up to 200 um.

The devices or methods of any prior embodiment, wherein the sample comprise an analyte, the predetermined constant inter-spacer distance is at least about 2 times larger than the size of the analyte, up to 200 um, and the Young's modulus of the spacers multiplied by the filling factor of the spacers is at least 2 MPa.

The devices or methods of any prior embodiment, wherein a fourth power of the inter-spacer-distance (IDS) divided by the thickness (h) and the Young's modulus (E) of the flexible plate (ISD$^4$/(hE)) is 5×10$^6$ um$^3$/GPa or less.

The devices or methods of any prior embodiment, wherein a fourth power of the inter-spacer-distance (IDS) divided by the thickness (h) and the Young's modulus (E) of the flexible plate (ISD$^4$/(hE)) is 1×10$^6$ um$^3$/GPa or less.

The devices or methods of any prior embodiment, wherein a fourth power of the inter-spacer-distance (IDS) divided by the thickness (h) and the Young's modulus (E) of the flexible plate (ISD$^4$/(hE)) is 5×10$^5$ um$^3$/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD$^4$/(hE)) is 1×10$^5$ um$^3$/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD$^4$/(hE)) is 1×10$^4$ um$^3$/GPa or less.

The devices or methods of any prior embodiment, wherein the Young's modulus of the spacers multiplied by the filling factor of the spacers is at least 20 MPa.

The devices or methods of any prior embodiment, wherein the ratio of the inter-spacing distance of the spacers to the average width of the spacer is 2 or larger.

The devices or methods of any prior embodiment, wherein the ratio of the inter-spacing distance of the spacers to the average width of the spacer is 2 or larger, and the Young's modulus of the spacers multiplied by the filling factor of the spacers is at least 2 MPa.

The devices or methods of any prior embodiment, wherein inter-spacer distance that is at least about 2 times larger than the size of the analyte, up to 200 um.

The devices or methods of any prior embodiment, wherein a ratio of the inter-spacer-distance to the spacer width is 1.5 or larger.

The devices or methods of any prior embodiment, wherein a ratio of the width to the height of the spacer is 1 or larger.

The devices or methods of any prior embodiment, wherein a ratio of the width to the height of the spacer is 1.5 or larger.

The devices or methods of any prior embodiment, wherein a ratio of the width to the height of the spacer is 2 or larger.

The devices or methods of any prior embodiment, wherein a ratio of the width to the height of the spacer is larger than 2, 3, 5, 10, 20, 30, 50, or in a range of any two the value.

The methods of any prior embodiment, wherein the force that presses the two plates into the closed configuration is an imprecise pressing force.

The methods of any prior embodiment, wherein the force that presses the two plates into the closed configuration is an imprecise pressing force provided by human hand.

The methods of any prior embodiment, wherein the forcing of the two plates to compress at least part of the sample into a layer of substantially uniform thickness comprises a use of a conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 20% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied; and wherein the layer of highly uniform thickness has a variation in thickness uniform of 20% or less.

The methods of any prior embodiment, wherein the pressing force is an imprecise force that has a magnitude which cannot, at the time that the force is applied, be determined within an accuracy equal or better than 30%, 40%, 50%, 70%, 100%, 200%, 300%, 500%, 1000%, 2000%, or in a range between any of the two values.

The devices or methods of any prior embodiment, wherein the flexible plate has a thickness of in the range of 10 um to 200 um.

The devices or methods of any prior embodiment, wherein the flexible plate has a thickness of in the range of 20 um to 100 um.

The devices or methods of any prior embodiment, wherein the flexible plate has a thickness of in the range of 25 um to 180 um.

The devices or methods of any prior embodiment, wherein the flexible plate has a thickness of in the range of 200 um to 260 um.

The devices or methods of any prior embodiment, wherein the flexible plate has a thickness of equal to or less than 250 um, 225 um, 200 um, 175 um, 150 um, 125 um, 100 um, 75 um, 50 um, 25 um, 10 um, 5 um, 1 um, or in a range between the two of the values.

The devices or methods of any prior method, wherein the sample has a viscosity in the range of 0.1 to 4 (mPa s).

The devices or methods of any prior embodiment, wherein the flexible plate has a thickness of in the range of 200 um to 260 um.

The devices or methods of any prior embodiment, wherein the flexible plate has a thickness in the range of 20 um to 200 um and Young's modulus in the range 0.1 to 5 GPa.

45. The method of any prior claim, wherein the sample deposition of step (b) is a deposition directly from a subject to the plate without using any transferring devices.

46. The method any prior claim, wherein during the deposition of step (b), the amount of the sample deposited on the plate is unknown.

47. The method of any prior claim, wherein the method further comprises an analyzing step (e) that analyze the sample.

48. The method of any prior claim, wherein the analyzing step (e) comprises calculating the volume of a relevant sample volume by measuring the lateral area of the relevant sample volume and calculating the volume from the lateral area and the predetermined spacer height.

49. The method of any prior claim, wherein the analyzing step (e) comprises measuring:
  i. imaging, illuminescence selected from photoluminescence, electroluminescence, and electrochemiluminescence,
  iii. surface Raman scattering,
  iv. electrical impedance selected from resistance, capacitance, and inductance, or
  v. any combination of i-iv.

50. The method of any prior claim, wherein the analyzing step (e) comprises reading, image analysis, or counting of the analyte, or a combination of thereof.

51. The method of any prior claim, wherein the sample contains one or plurality of analytes, and one or both plate sample contact surfaces comprise one or a plurality of binding sites that each binds and immobilize a respective analyte.

52. The method of any prior claim, wherein one or both plate sample contact surfaces comprise one or a plurality of storage sites that each stores a reagent or reagents, wherein the reagent(s) dissolve and diffuse in the sample during or after step (c).

53. The method of any prior claim, wherein one or both plate sample contact surfaces comprises one or a plurality of amplification sites that are each capable of amplifying a signal from the analyte or a label of the analyte when the analyte or label is within 500 nm from an amplification site.

54. The method of any prior claim, wherein:
  i. one or both plate sample contact surfaces comprise one or a plurality of binding sites that each binds and immobilize a respective analyte; or
  ii. one or both plate sample contact surfaces comprise, one or a plurality of storage sites that each stores a reagent or reagents; wherein the reagent(s) dissolve and diffuse in the sample during or after step (c), and wherein the sample contains one or plurality of analytes; or
  iii. one or a plurality of amplification sites that are each capable of amplifying a signal from the analyte or a label of the analyte when the analyte or label is 500 nm from the amplification site; or
  iv. any combination of i to iii.

55. The devices or methods of any prior embodiment, wherein the liquid sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

56. The devices or methods of any prior embodiment, wherein the layer of uniform thickness in the closed configuration is less than 150 um.

57. The method of any prior claim, wherein the pressing is provided by a pressured liquid, a pressed gas, or a conformal material.

58. The method of any prior claim, wherein the analyzing comprises counting cells in the layer of uniform thickness.

59. The method of any prior claim, wherein the analyzing comprises performing an assay in the layer of uniform thickness.

60. The devices or methods of any prior embodiment, wherein the assay is a binding assay or biochemical assay.

61. The method of any prior claim, wherein the sample deposited has a total volume less 0.5 uL 62. The method of any prior claim, wherein multiple drops of sample are deposited onto one or both of the plates.

63. The devices or methods of any prior embodiment, wherein the inter-spacer distance is in the range of 1 □m to 120 □m.

64. The devices or methods of any prior embodiment, wherein the inter-spacer distance is in the range of 120 □m to 50 □m.

65. The devices or methods of any prior embodiment, wherein the inter-spacer distance is in the range of 120 □m to 200 □m.

66. The device of any prior device claim, wherein the flexible plates have a thickness in the range of 20 um to 250 um and Young's modulus in the range 0.1 to 5 GPa.

67. The device of any prior device claim, wherein for a flexible plate, the thickness of the flexible plate times the Young's modulus of the flexible plate is in the range 60 to 750 GPa-um.

68. The device of any prior device claim, wherein the layer of uniform thickness sample is uniform over a lateral area that is at least 1 mm$^2$.

69. The device of any prior device claim, wherein the layer of uniform thickness sample is uniform over a lateral area that is at least 3 mm$^2$.

70. The device of any prior device claim, wherein the layer of uniform thickness sample is uniform over a lateral area that is at least 5 mm$^2$.

71. The device of any prior device claim, wherein the layer of uniform thickness sample is uniform over a lateral area that is at least 10 mm$^2$.

72. The device of any prior device claim, wherein the layer of uniform thickness sample is uniform over a lateral area that is at least 20 mm$^2$.
73. The device of any prior device claim, wherein the layer of uniform thickness sample is uniform over a lateral area that is in a range of 20 mm$^2$ to 100 mm$^2$.
74. The device of any prior device claim, wherein the layer of uniform thickness sample has a thickness uniformity of up to +/−5% or better.
75. The device of any prior device claim, wherein the layer of uniform thickness sample has a thickness uniformity of up to +/−10% or better.
76. The device of any prior device claim, wherein the layer of uniform thickness sample has a thickness uniformity of up to +/−20% or better.
77. The device of any prior device claim, wherein the layer of uniform thickness sample has a thickness uniformity of up to +/−30% or better.
78. The device of any prior device claim, wherein the layer of uniform thickness sample has a thickness uniformity of up to +/−40% or better.
79. The device of any prior device claim, wherein the layer of uniform thickness sample has a thickness uniformity of up to +/−50% or better.
80. The device of any prior device claim, wherein the spacers are pillars with a cross-sectional shape selected from round, polygonal, circular, square, rectangular, oval, elliptical, or any combination of the same.
81. The device of any prior device claim, wherein the spacers have pillar shape, have a substantially flat top surface, and have substantially uniform cross-section, wherein, for each spacer, the ratio of the lateral dimension of the spacer to its height is at least 1.
82. The device of any prior device claim, wherein the inter spacer distance is periodic.
83. The device of any prior device claim, wherein the spacers have a filling factor of 1% or higher, wherein the filling factor is the ratio of the spacer contact area to the total plate area.
84. The device of any prior device claim, wherein the Young's modulus of the spacers times the filling factor of the spacers is equal or larger than 20 MPa, wherein the filling factor is the ratio of the spacer contact area to the total plate area.
85. The device of any prior device claim, wherein the spacing between the two plates at the closed configuration is in less 200 um.
86. The device of any prior device claim, wherein the spacing between the two plates at the closed configuration is a value selected from between 1.8 um and 3.5 um.
87. The device of any prior device claim, wherein the spacing are fixed on a plate by directly embossing the plate or injection molding of the plate.
88. The device of any prior device claim, wherein the materials of the plate and the spacers are selected from polystyrene, PMMA, PC, COC, COP, or another plastic.
89. The device of any prior device claim, wherein the spacers have a pillar shape, and the sidewall corners of the spacers have a round shape with a radius of curvature at least 1 ☐m.
90. The device of any prior device claim, wherein the spacers have a density of at least 1000/mm$^2$.
91. The device of any prior device claim, wherein at least one of the plates is transparent.
92. The device of any prior device claim, wherein the mold used to make the spacers is fabricated by a mold containing features that are fabricated by either (a) directly reactive ion etching or ion beam etched or (b) by a duplication or multiple duplication of the features that are reactive ion etched or ion beam etched.
93. The devices or methods of any prior embodiment, wherein the spacers are configured, such that the filling factor is in the range of 1% to 5%.

The devices or methods of any prior embodiment, wherein the surface variation is relative to the spacer height and the ratio of the pillar flat top surface variation to the spacer height is less than 0.5%, 1%, 3%,5%,7%,10%,15%, 20%, 30%,40%, or in a range between any two of the values. A preferred flat pillar top smoothness has a ratio of the pillar flat top surface variation to the spacer height is less than 2%, 5%, or 10%.
94. The devices or methods of any prior embodiment, wherein the spacers are configured, such that the filling factor is in the range of 1% to 5%.
95. The devices or methods of any prior embodiment, wherein the spacers are configured, such that the filling factor is in the range of 5% to 10%.
96. The devices or methods of any prior embodiment, wherein the spacers are configured, such that the filling factor is in the range of 10% to 20%.
97. The devices or methods of any prior embodiment, wherein the spacers are configured, such that the filling factor is in the range of 20% to 30%.
98. The devices or methods of any prior embodiment, wherein the spacers are configured, such that the filling factor is 5%, 10%, 20%, 30%, 40%,50%, or in a range of any two of the values.
99. The devices or methods of any prior embodiment, wherein the spacers are configured, such that the filling factor is 50%, 60%, 70%, 80%, or in a range of any two of the values.
100. The devices or methods of any prior embodiment, wherein the spacers are configured, such that the filling factor multiplies the Young's modulus of the spacer is in the range of 2 MPa and 10 MPa.
101. The devices or methods of any prior embodiment, wherein the spacers are configured, such that the filling factor multiplies the Young's modulus of the spacer is in the range of 10 MPa and 20 MPa.
102. The devices or methods of any prior embodiment, wherein the spacers are configured, such that the filling factor multiplies the Young's modulus of the spacer is in the range of 20 MPa and 40 MPa.
103. The devices or methods of any prior embodiment, wherein the spacers are configured, such that the filling factor multiplies the Young's modulus of the spacer is in the range of 40 MPa and 80 MPa.
104. The devices or methods of any prior embodiment, wherein the spacers are configured, such that the filling factor multiplies the Young's modulus of the spacer is in the range of 80 MPa and 120 MPa.
105. The devices or methods of any prior embodiment, wherein the spacers are configured, such that the filling factor multiplies the Young's modulus of the spacer is in the range of 120 MPa to 150 MPa.
106. The devices or methods of any prior embodiment, wherein the device further comprises a dry reagent coated on one or both plates.
107. The devices or methods of any prior embodiment, wherein the device further comprises, on one or both plates, a dry binding site that has a predetermined area, wherein the dry binding site binds to and immobilizes an analyte in the sample.

108. The devices or methods of any prior embodiment, wherein the device further comprises, on one or both plates, a releasable dry reagent and a release time control material that delays the time that the releasable dry regent is released into the sample.
109. The device of any prior embodiment, wherein the release time control material delays the time that the dry regent starts is released into the sample by at least 3 seconds.
110. The device of any prior embodiment, wherein the regent comprises anticoagulant and/or staining reagent(s)
111. The device of any prior embodiment, wherein the reagent comprises cell lysing reagent(s)
112. The devices or methods of any prior embodiment, wherein the device further comprises, on one or both plates, one or a plurality of dry binding sites and/or one or a plurality of reagent sites.
113. The device of any prior device embodiment, wherein the analyte comprises a molecule (e.g., a protein, peptides, DNA, RNA, nucleic acid, or other molecule), cells, tissues, viruses, and nanoparticles with different shapes.
114. The device of any prior device embodiment, wherein the analyte comprises white blood cells, red blood cells and platelets.
115. The device of any prior device embodiment, wherein the analyte is stained.
116. The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.
117. The devices or methods of any prior embodiment, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.
118. The devices or methods of any prior embodiment, wherein for a flexible plate, the thickness of the flexible plate times the Young's modulus of the flexible plate is in the range 60 to 750 GPa-um.
119. The devices or methods of any prior embodiment, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3/GPa$,
120. The devices or methods of any prior embodiment, wherein one or both plates comprises a location marker, either on a surface of or inside the plate, that provide information of a location of the plate.
121. The devices or methods of any prior embodiment, wherein one or both plates comprises a scale marker, either on a surface of or inside the plate, that provide information of a lateral dimension of a structure of the sample and/or the plate.
122. The devices or methods of any prior embodiment, wherein one or both plates comprises an imaging marker, either on surface of or inside the plate, that assists an imaging of the sample.
123. The devices or methods of any prior embodiment, wherein the spacers functions as a location marker, a scale marker, an imaging marker, or any combination of thereof.
124. The devices or methods of any prior embodiment, wherein the average thickness of the layer of uniform thickness is about equal to a minimum dimension of an analyte in the sample.
125. The devices or methods of any prior embodiment, wherein the inter-spacer distance is in the range of 7 □m to 50 □m.
126. The devices or methods of any prior embodiment, wherein the inter-spacer distance is in the range of 50 □m to 120 □m.
127. The devices or methods of any prior embodiment, wherein the inter-spacer distance is in the range of 120 □m to 200 □m (micron).
128. The devices or methods of any prior embodiment, wherein the inter-spacer distance is substantially periodic.
129. The devices or methods of any prior embodiment, wherein the spacers are pillars with a cross-sectional shape selected from round, polygonal, circular, square, rectangular, oval, elliptical, or any combination of the same.
130. The devices or methods of any prior embodiment, wherein the spacers have are pillar shape and have a substantially flat top surface, wherein, for each spacer, the ratio of the lateral dimension of the spacer to its height is at least 1.
131. The devices or methods of any prior embodiment, wherein each spacer has the ratio of the lateral dimension of the spacer to its height is at least 1.
132. The devices or methods of any prior embodiment, wherein the minimum lateral dimension of spacer is less than or substantially equal to the minimum dimension of an analyte in the sample.
133. The devices or methods of any prior embodiment, wherein the minimum lateral dimension of spacer is in the range of 0.5 um to 100 um.
134. The devices or methods of any prior embodiment, wherein the minimum lateral dimension of spacer is in the range of 0.5 um to 10 um.
135. The devices or methods of any prior embodiment, wherein the sample is blood.
136. The devices or methods of any prior embodiment, wherein the sample is whole blood without dilution by liquid.
137. The devices or methods of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
138. The devices or methods of any prior embodiment, wherein the sample is a biological sample, an environmental sample, a chemical sample, or clinical sample.
139. The devices or methods of any prior embodiment, wherein the spacers have a pillar shape, and the sidewall corners of the spacers have a round shape with a radius of curvature at least 1 □m.
140. The devices or methods of any prior embodiment, wherein the spacers have a density of at least $100/mm^2$.
141. The devices or methods of any prior embodiment, wherein the spacers have a density of at least $1000/mm^2$.
142. The devices or methods of any prior embodiment, wherein at least one of the plates is transparent.

143. The devices or methods of any prior embodiment, wherein at least one of the plates is made from a flexible polymer.
144. The devices or methods of any prior embodiment, wherein, for a pressure that compresses the plates, the spacers are not compressible and/or, independently, only one of the plates is flexible.
145. The device of any of any prior embodiment, wherein the flexible plate has a thickness in the range of 10 um to 200 um.
146. The devices or methods of any prior embodiment, wherein the variation is less than 30%.
147. The devices or methods of any prior embodiment, wherein the variation is less than 10%.
148. The devices or methods of any prior embodiment, wherein the variation is less than 5%.
149. The devices or methods of any prior embodiment, wherein the first and second plates are connected and are configured to be changed from the open configuration to the closed configuration by folding the plates.
150. The devices or methods of any prior embodiment, wherein the first and second plates are connected by a hinge and are configured to be changed from the open configuration to the closed configuration by folding the plates along the hinge.
151. The devices or methods of any prior embodiment, wherein the first and second plates are connected by a hinge that is a separate material to the plates, and are configured to be changed from the open configuration to the closed configuration by folding the plates along the hinge
152. The devices or methods of any prior embodiment, wherein the first and second plates are made in a single piece of material and are configured to be changed from the open configuration to the closed configuration by folding the plates.
153. The devices or methods of any prior embodiment, wherein the layer of uniform thickness sample is uniform over a lateral area that is at least 1 mm$^2$.
154. The devices or methods of any prior embodiment, wherein the device is configured to analyze the sample in 60 seconds or less.
155. The devices or methods of any prior embodiment, wherein at the closed configuration, the final sample thickness device is configured to analyze the sample in 60 seconds or less.
156. The devices or methods of any prior embodiment, wherein at the closed configuration, the final sample thickness device is configured to analyze the sample in 10 seconds or less.
157. The devices or methods of any prior embodiment, wherein the dry binding site comprises a capture agent.
158. The devices or methods of any prior embodiment, wherein the dry binding site comprises an antibody or nucleic acid.
159. The devices or methods of any prior embodiment, wherein the releasable dry reagent is a labeled reagent.
160. The devices or methods of any prior embodiment, wherein the releasable dry reagent is a fluorescently-labeled reagent.
161. The devices or methods of any prior embodiment, wherein the releasable dry reagent is a fluorescently-labeled antibody.
162. The devices or methods of any prior embodiment, wherein the releasable dry reagent is a cell stain.
163. The devices or methods of any prior embodiment, wherein the releasable dry reagent is a cell lysing.
164. The devices or methods of any prior embodiment, wherein the detector is an optical detector that detects an optical signal.
165. The devices or methods of any prior embodiment, wherein the detector is an electric detector that detect electrical signal.
166. The device of any prior device embodiment, wherein the spacing are fixed on a plate by directly embossing the plate or injection molding of the plate.
167. The device of any prior device embodiment, wherein the materials of the plate and the spacers are selected from polystyrene, PMMA, PC, COC, COP, or another plastic.
168. A system for rapidly analyzing a sample using a mobile phone comprising:
    (a) a device of any prior embodiment;
    (b) a mobile communication device comprising:
        i. one or a plurality of cameras for the detecting and/or imaging the sample;
        ii. electronics, signal processors, hardware and software for receiving and/or processing the detected signal and/or the image of the sample and for remote communication; and
    (c) a light source from either the mobile communication device or an external source;
    wherein the detector in the devices or methods of any prior embodiment is provided by the mobile communication device, and detects an analyte in the sample at the closed configuration.
169. The system of any prior system embodiment, wherein one of the plates has a binding site that binds an analyte, wherein at least part of the uniform sample thickness layer is over the binding site, and is substantially less than the average lateral linear dimension of the binding site.
170. The system of any prior system embodiment, further comprising:
    (d) a housing configured to hold the sample and to be mounted to the mobile communication device.
171. The system of any prior system embodiment, wherein the housing comprises optics for facilitating the imaging and/or signal processing of the sample by the mobile communication device, and a mount configured to hold the optics on the mobile communication device.
172. The system of any prior system embodiment, wherein an element of the optics in the housing is movable relative to the housing.
173. The system of any prior system embodiment, wherein the mobile communication device is configured to communicate test results to a medical professional, a medical facility or an insurance company.
174. The system of any prior system embodiment, wherein the mobile communication device is further configured to communicate information on the test and the subject with the medical professional, medical facility or insurance company.
175. The system of any prior system embodiment, wherein the mobile communication device is further configured to communicate information of the test to a cloud network, and the cloud network process the information to refine the test results.
176. The system of any prior system embodiment, wherein the mobile communication device is further configured to communicate information of the test and the subject to a cloud network, the cloud network process the information to refine the test results, and the refined test results will send back the subject.

177. The system of any prior system embodiment, wherein the mobile communication device is configured to receive a prescription, diagnosis or a recommendation from a medical professional.
178. The system of any prior system embodiment, wherein the mobile communication device is configured with hardware and software to:
    (a) capture an image of the sample;
    (b) analyze a test location and a control location in in image; and
    (c) compare a value obtained from analysis of the test location to a threshold value that characterizes the rapid diagnostic test.
179. The system of any prior system embodiment, wherein at least one of the plates comprises a storage site in which assay reagents are stored.
180. The system of any prior system embodiment, at least one of the cameras reads a signal from the device.
181. The system of any prior system embodiment, wherein the mobile communication device communicates with the remote location via a wifi or cellular network.
182. The system of any prior system embodiment, wherein the mobile communication device is a mobile phone.
183. A method for rapidly analyzing an analyte in a sample using a mobile phone, comprising:
    (a) depositing a sample on the device of any prior system embodiment;
    (b) assaying an analyte in the sample deposited on the device to generate a result; and
    (c) communicating the result from the mobile communication device to a location remote from the mobile communication device.
184. The method of any prior embodiments embodiment, wherein the analyte comprises a molecule (e.g., a protein, peptides, DNA, RNA, nucleic acid, or other molecule), cells, tissues, viruses, and nanoparticles with different shapes.
185. The method of any prior embodiment, wherein the analyte comprises white blood cell, red blood cell and platelets.
186. The method of any prior embodiment, wherein the assaying comprises performing a white blood cells differential assay.
187. The method of any prior embodiments embodiment, wherein the method comprises:
    analyzing the results at the remote location to provide an analyzed result; and
    communicating the analyzed result from the remote location to the mobile communication device.
188. The method of any prior embodiment, wherein the analysis is done by a medical professional at a remote location.
189. The method of any prior embodiment, wherein the mobile communication device receives a prescription, diagnosis or a recommendation from a medical professional at a remote location.
190. The method of any prior embodiment, wherein the sample is a bodily fluid.
191. The method of any prior embodiment, wherein the bodily fluid is blood, saliva or urine.
192. The method of any prior embodiment, wherein the sample is whole blood without dilution by a liquid.
193. The method of any prior embodiment, wherein the assaying step comprises detecting an analyte in the sample.
194. The method of any prior embodiment, wherein the analyte is a biomarker.
195. The method of any prior embodiment, wherein the analyte is a protein, nucleic acid, cell, or metabolite.
196. The method of any prior embodiment, wherein the method comprises counting the number of red blood cells.
197. The method of any of any prior embodiment, wherein the method comprises counting the number of white blood cells.
198. The method of any prior embodiment, wherein method comprises staining the cells in the sample and counting the number of neutrophils, lymphocytes, monocytes, eosinophils and basophils.
199. The method of any prior embodiments embodiment, wherein the assay done in step (b) is a binding assay or a biochemical assay.
200. A method for analyzing a sample comprising:
    obtaining a device of any prior device embodiment;
    depositing the sample onto one or both pates of the device;
    placing the plates in a closed configuration and applying an external force over at least part of the plates; and
    analyzing the in the layer of uniform thickness while the plates are the closed configuration.
201. The devices or methods of any prior embodiment, wherein the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.
202. The devices or methods of any prior embodiment, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.
203. The devices or methods of any prior embodiment, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.
204. The devices or methods of any prior embodiment, wherein the analyte assay area is between a pair of electrodes.
205. The devices or methods of any prior embodiment, wherein the assay area is defined by a patch of dried reagent.
206. The devices or methods of any prior embodiment, wherein the assay area binds to and immobilizes the analyte
207. The devices or methods of any prior embodiment, wherein the assay area is defined by a patch of binding reagent that, upon contacting the sample, dissolves into the sample, diffuses in the sample, and binds to the analyte.
208. The devices or methods of any prior embodiment, wherein the inter-spacer distance is in the range of 14 ☐m to 200 ☐m.

209. The devices or methods of any prior embodiment, wherein the inter-spacer distance is in the range of 7 µm to 20 µm.

210. The devices or methods of any prior embodiment, wherein the spacers are pillars with a cross-sectional shape selected from round, polygonal, circular, square, rectangular, oval, elliptical, or any combination of the same.

211. The devices or methods of any prior embodiment, wherein the spacers have a pillar shape and have a substantially flat top surface, wherein, for each spacer, the ratio of the lateral dimension of the spacer to its height is at least 1.

212. The devices or methods of any prior embodiment, wherein the spacers have a pillar shape, and the sidewall corners of the spacers have a round shape with a radius of curvature at least 1 µm.

213. The devices or methods of any prior embodiment, wherein the spacers have a density of at least 1000/mm$^2$.

214. The devices or methods of any prior embodiment, wherein at least one of the plates is transparent.

215. The devices or methods of any prior embodiment, wherein at least one of the plates is made from a flexible polymer.

216. The devices or methods of any prior embodiment, wherein only one of the plates is flexible.

The device of any prior embodiment, wherein the area-determination device is a camera.

The area-determination device comprises an area in the sample contact area of a plate, wherein the area is less than 1/100, 1/20, 1/10, 1/6, 1/5, 1/4, 1/3, 1/2, 2/3 of the sample contact area, or in a range between any of the two values.

The area-determination device comprises a camera and an area in the sample contact area of a plate, wherein the area is in contact with the sample.

The devices or methods of any prior embodiment, wherein the deformable sample comprises a liquid sample.

The devices or methods of any prior embodiment, wherein the imprecision force has a variation at least 30% of the total force that actually is applied.

The devices or methods of any prior embodiment, wherein the imprecision force has a variation at least 20%, 30%, 40%, 50%, 60, 70%, 80%, 90% 100%, 150%, 200%, 300%, 500%, or in a range of any two values, of the total force that actually is applied.

217. The device or method of any prior embodiment, wherein spacers have a flat top.

218. The device or method of any prior embodiment, wherein the device is further configured to have, after the pressing force is removed, a sample thickness that is substantially the same in thickness and uniformity as that when the force is applied.

219. The device or method of any prior embodiment, wherein the imprecise force is provided by human hand.

220. The device or method of any prior embodiment, wherein the inter spacer distance is substantially constant.

221. The device or method of any prior embodiment, wherein the inter spacer distance is substantially periodic in the area of the uniform sample thickness area.

222. The device or method of any prior embodiment, wherein the multiplication product of the filling factor and the Young's modulus of the spacer is 2 MPa or larger.

223. The device or method of any prior embodiment, wherein the force is applied by hand directly or indirectly.

224. The device or method of any prior embodiment, wherein the force applied is in the range of 5 N to 20 N.

225. The device or method of any prior embodiment wherein the highly uniform layer has a thickness that varies by less than 15%, 10%, or 5% of an average thickness.

226. The device or method of any prior embodiment, wherein the imprecise force is applied by pinching the device between a thumb and forefinger.

227. The device or method of any prior embodiment, wherein the predetermined sample thickness is larger than the spacer height.

228. The device or method of any prior embodiment, wherein the device holds itself in the closed configuration after the pressing force has been removed.

229. The device or method of any prior embodiment, wherein the uniform thickness sample layer area is larger than that area upon which the pressing force is applied.

230. The device or method of any prior embodiment, wherein the spacers do not significantly deform during application of the pressing force.

231. The device or method of any prior embodiment, wherein the pressing force is not predetermined beforehand and is not measured.

232. The device of any prior device embodiment, wherein the analyte comprises a molecule (e.g., a protein, peptides, DNA, RNA, nucleic acid, or other molecule), cells, tissues, viruses, and nanoparticles with different shapes.

233. The device of any prior device embodiment, wherein the analyte comprises white blood cells, red blood cells and platelets.

234. The device of any prior device embodiment, wherein the analyte is stained.

235. The method or device of any prior embodiment, wherein the inter spacer distance (SD) is equal or less than about 120 um (micrometer).

236. The method or device of any prior embodiment, wherein the inter spacer distance (SD) is equal or less than about 100 um (micrometer).

237. The method or device of any prior embodiment, wherein the fourth power of the inter-spacer-distance (ISD) divided by the thickness (h) and the Young's modulus (E) of the flexible plate (ISD$^4$/(hE)) is 5×10$^6$ um$^3$/GPa or less.

238. The method or device of any prior embodiment, wherein the fourth power of the inter-spacer-distance (ISD) divided by the thickness (h) and the Young's modulus (E) of the flexible plate (ISD$^4$/(hE)) is 5×10$^5$ um$^3$/GPa or less.

239. The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

240. The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is $5\times10^6$ um$^3$/GPa or less.

241. The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.

242. The method or device of any prior embodiment, wherein the analytes is the analyte in 5 detection of proteins, peptides, nucleic acids, synthetic compounds, and inorganic compounds.

243. The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

244. The method or device of any prior embodiment, wherein the spacers have a shape of pillars and a ratio of the width to the height of the pillar is equal or larger than one.

245. The method of any prior embodiment, wherein the sample that is deposited on one or both of the plates has an unknown volume.

246. The method or device of any prior embodiment, wherein the samples is for the detection, purification and quantification of chemical compounds or biomolecules that correlates with the stage of certain diseases.

247. The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.

248. The method or device of any prior embodiment, wherein the samples is related to the detection, purification and quantification of microorganism.

249. The method or device of any prior embodiment, wherein the samples is related to virus, fungus and bacteria from environment, e.g., water, soil, or biological samples.

250. The method or device of any prior embodiment, wherein the samples is related to the detection, quantification of chemical compounds or biological samples that pose hazard to food safety or national security, e.g. toxic waste, anthrax.

251. The method or device of any prior embodiment, wherein the samples is related to quantification of vital parameters in medical or physiological monitor.

252. The method or device of any prior embodiment, wherein the samples is related to glucose, blood, oxygen level, total blood count.

253. The method or device of any prior embodiment, wherein the samples is related to the detection and quantification of specific DNA or RNA from biosamples.

254. The method or device of any prior embodiment, wherein the samples is related to the sequencing and comparing of genetic sequences in DNA in the chromosomes and mitochondria for genome analysis.

255. The method or device of any prior embodiment, wherein the samples is related to detect reaction products, e.g., during synthesis or purification of pharmaceuticals.

256. The method or device of any prior embodiment, wherein the samples is cells, tissues, bodily fluids, and stool.

257. The method or device of any prior embodiment, wherein the sample is the sample in the detection of proteins, peptides, nucleic acids, synthetic compounds, inorganic compounds.

258. The method or device of any prior embodiment, wherein the sample is the sample in the fields of human, veterinary, agriculture, foods, environments, and drug testing.

259. The method or device of any prior embodiment, wherein the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, throat swab, stool samples, hair, finger nail, ear wax, breath, connective tissue, muscle tissue, nervous tissue, epithelial tissue, cartilage, cancerous sample, or bone.

260. The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.

Manufacturing of Q-Card

MA1. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) a sample overflow dam that surrounds the sample contact area is configured to present a sample flow outside of the dam;
  ii. the second plate is 10 um to 250 um thick and comprises, on its inner surface, (a) a sample contact area for contacting a sample, and (b) spacers on the sample contact area;
  iii. the hinge that connect the first and the second plates; and wherein the first and second plate are movable relative to each other around the axis of the hinge.

MA2. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, (b) a sample overflow dam that surrounds the sample contact area is configured to present a sample flow outside of the dam, and (c) spacers on the sample contact area;
  ii. the second plate, that is 10 um to 250 um thick, comprises, on its inner surface, a sample contact area for contacting a sample;
  iii. the hinge that connect the first and the second plates; and wherein the first and second plate are movable relative to each other around the axis of the hinge.

MA3. An embodiment of the Q-Card comprising: a first plate, a second plate, and a hinge, wherein
i. the first plate, that is about 200 nm to 1500 nm thick, comprises, on its inner surface, (a) a sample contact area for contacting a sample, and (b) spacers on the sample contact area;
ii. the second plate, that is 10 um to 250 um thick, comprises, on its inner surface, (a) a sample contact area for contacting a sample, and (b) a sample overflow dam that surrounds the sample contact area is configured to present a sample flow outside of the dam, and;
iii. the hinge that connect the first and the second plates; and wherein the first and second plate are movable relative to each other around the axis of the hinge.

MA4 An embodiment of the Q-Card comprising: a first plate, a second plate, and a hinge, wherein
i. the first plate, that is about 200 nm to 1500 nm thick, comprises, on its inner surface, a sample contact area for contacting a sample;
ii. the second plate, that is 10 um to 250 um thick, comprises, on its inner surface, (a) a sample contact area for contacting a sample, (b) a sample overflow dam that surrounds the sample contact area is configured to present a sample flow outside of the dam, and (c) spacers on the sample contact area; and
iii. the hinge that connect the first and the second plates; and wherein the first and second plate are movable relative to each other around the axis of the hinge.

M1 An embodiment of a method for fabricating the Q-Card of any embodiments of MA1 to MA4, comprising:
(a) injection molding of the first plate,
(b) nanoimprinting or extrusion printing of the second plate.

M2 An embodiment of a method for fabricating the Q-Card of any embodiments of MA1 to MA4, comprising:
(a) Laser cutting the first plate,
(b) nanoimprinting or extrusion printing of the second plate.

M3 An embodiment of a method for fabricating the Q-Card of any embodiments of MA1 to MA4, comprising:
(a) Injection molding and laser cutting the first plate,
(b) nanoimprinting or extrusion printing of the second plate.

M4 An embodiment of a method for fabricating the Q-Card of any embodiments of MA1 to MA4, comprising: nanoimprinting or extrusion printing to fabricated both the first and the second plate.

M5 An embodiment of a method for fabricating the Q-Card of any embodiments of MA1 to MA4, comprising: fabricating the first plate or the second plate, using injection molding, laser cutting the first plate, nanoimprinting, extrusion printing, or a combination of thereof.

The method of any embodiments of M1-M5, wherein the method further comprises a step of attach the hinge on the first and the second plates after the fabrication of the first and second plates.

Device and System for Collecting and Analyzing Vapor Condensate, Particularly Exhaled Breath Condensate, as Well Method of Using the Same A device is provided herein for collecting and analyzing vapor condensate (VC) sample, comprising:
a collection plate, a cover plate, and spacers, wherein:
i. the plates are movable relative to each other into different configurations;
ii. one or both plates are flexible;
iii. each of the plates has, on its respective inner surface, a sample contact area for contacting a vapor condensate (VC) sample that contains an analyte;
iv. the spacers are fixed to the respective inner surface of one or both of the plates, and have a predetermined substantially uniform height and a predetermined constant inter-spacer distance and wherein at least one of the spacers is inside the sample contact area;

wherein one of the configurations is an open configuration, in which: the two plates are either completely or partially separated apart, the spacing between the plates is not regulated by the spacers, and the VC sample is deposited on one or both of the plates; and wherein another of the configurations is a closed configuration which is configured after the VC sample deposition in the open configuration; and in the closed configuration: at least a part of the VC sample is between the two plates and in contact with the two plates, and has a highly uniform thickness that is regulated by the spacers and the two sample surfaces of the plates and is equal to or less than 30 $\Box$m with a small variation.

Another device is provided herein for collecting and analyzing vapor condensate (VC) sample, comprising:
a collection plate and a cover plate, wherein:
i. the plates are movable relative to each other into different configurations;
ii. one or both plates are flexible; and
iii. each of the plates has, on its respective surface, a sample contact area for contacting a vapor condensate (VC) sample that contains an analyte;

wherein one of the configurations is an open configuration, in which: the two plates are either completely or partially separated apart, and the VC sample is deposited on one or both of the plates; and wherein another of the configurations is a closed configuration which is configured after the VC sample deposition in the open configuration; and in the closed configuration: at least a part of the VC sample is between the two plates and in contact with the two plates, and has a thickness that is regulated by the plate spacing.

In some embodiments, the device further comprises, on one or both plates, one or a plurality of dry binding sites and/or one or a plurality of reagent sites. In some embodiments, the sample is exhale breath condensate.

In some embodiments, the sample is a vapor from a biological sample, an environmental sample, a chemical sample, or clinical sample. In some embodiments, wherein the analyte comprises a molecule (e.g., a protein, peptides, DNA, RNA, nucleic acid, or other molecules), cells, tissues, viruses, and nanoparticles with different shapes. In some embodiments, wherein the analyte comprises volatile organic compounds (VOCs). In some embodiments, wherein the analyte comprises nitrogen, oxygen, $CO_2$, $H_2O$, and inert gases. In some embodiments, wherein the analyte is stained.

In some embodiments, the device may comprise a dry reagent coated on one or both of the plates. In some embodiments, the dry reagent may bind to an analyte in the blood an immobilize the analyte on a surface on one or both of the plates. In these embodiments, the reagent may be an antibody or other specific binding agent, for example. This dry reagent may have a pre-determined area. In other embodiments, the device may comprise a releasable dry reagent on one or more of the plates, e.g., a labeled reagent such as a cell stain or a labeled detection agent such as an antibody or the like. In some cases, there may be a release time control material on the plate that contains the releasable dry reagent, wherein the release time control material delays the time that the releasable dry regent is released into the blood sample.

In some cases, the release time control material delays the time that the dry regent is released into the blood sample by at least 3 seconds, e.g., at least 5 seconds or at least 10 seconds. Some embodiments, the drive may contain multiple dry binding sites and/or multiple reagent sites, thereby allowing multiplex assays to be performed. In some cases, the areas occupied by the drying binding sites may oppose the areas occupied by the reagent sites when the plates are in the closed position.

In some embodiments, the regent comprises labeling or staining reagent(s).

In some embodiments, the spacers regulating the layer of uniform thickness (i.e., the spacers that are spacing the plates away from each other in the layer) have a "filling factor" of at least 1%, e.g., at least 2% or at least 5%, wherein the filling factor is the ratio of the spacer area that is in contact with the layer of uniform thickness to the total plate area that is in contact with the layer of uniform thickness. In some embodiments, for spacers regulating the layer of uniform thickness, the Young's modulus of the spacers times the filling factor of the spacers is equal or larger than 10 MPa, e.g., at least 15 MPa or at least 20 MPa, where the filling factor is the ratio of the spacer area that is in contact with the layer of uniform thickness to the total plate area that is in contact with the layer of uniform thickness. In some embodiments, the thickness of the flexible plate times the Young's modulus of the flexible plate is in the range 60 to 750 GPa-um, e.g., 100 to 300 GPa-um, 300 to 550 GPa-um, or 550 to 750 GPa-um. In some embodiments, for a flexible plate, the fourth power of the inter-spacer-distance (ISD) divided by the thickness of the flexible plate (h) and the Young's modulus (E) of the flexible plate, $ISD4/(hE)$, is equal to or less than 106 um3/GPa, e.g., less than 105 um3/GPa, less than 104 um3/GPa or less than 103 um3/GPa.

In some embodiments, one or both plates comprises a location marker either on a surface of or inside the plate, that provide information of a location of the plate, e.g., a location that is going to be analyzed or a location onto which the blood should be deposited. In some cases, one or both plates may comprise a scale marker, either on a surface of or inside the plate, that provides information of a lateral dimension of a structure of the blood sample and/or the plate. In some embodiments, one or both plates comprises an imaging marker, either on surface of or inside the plate that assists an imaging of the sample. For example, the imaging marker could help focus the imaging device or direct the imaging device to a location on the device. In some embodiments, the spacers can function as a location marker, a scale marker, an imaging marker, or any combination of thereof.

In some embodiments, on one of the sample surface, it further comprises an enclosure-spacer that encloses a partial or entire VC samples deposited on the collection plate.

In some embodiments, the highly uniform thickness has a value equal to or less than 0.5 um. In some embodiments, the highly uniform thickness has a value in the range of 0.5 um to 1 um, 1 um to 2 um, 2 um to 10 um, 10 um to 20 um or 20 um to 30 um.

In some embodiments, the thickness of the at least a part of VC sample at the closed configuration is larger than the thickness of VC sample deposited on the collection plate at an open configuration.

In some embodiments, the thickness of the at least a part of VC sample at the closed configuration is less than the thickness of VC sample deposited on the collection plate at an open configuration.

In some embodiments, wherein the spacers are fixed on a plate by directly embossing the plate or injection molding of the plate.

In some embodiments, wherein the materials of the plate and the spacers are selected from polystyrene, PMMA, PC, COC, COP, or another plastic.

In some embodiments, the inter-spacer spacing in the range of 1 um to 50 um, 50 um to 100 um, 100 um to 200 um or 200 um to 1000 um.

In some embodiments, the VC sample is an exhaled breath condensate from a human or an animal.

In some embodiments, the spacers regulating the layer of uniform thickness have a filling factor of at least 1%, wherein the filling factor is the ratio of the spacer area in contact with the layer of uniform thickness to the total plate area in contact with the layer of uniform thickness.

In some embodiments, for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

In some embodiments, for a flexible plate, the thickness of the flexible plate times the Young's modulus of the flexible plate is in the range 60 to 750 GPa-um.

In some embodiments, for a flexible plate, the fourth power of the inter-spacer-distance (ISD) divided by the thickness of the flexible plate (h) and the Young's modulus (E) of the flexible plate, $ISD4/(hE)$, is equal to or less than 106 um3/GPa, In some embodiments, one or both plates comprises a location marker, either on a surface of or inside the plate, that provide information of a location of the plate.

In some embodiments, one or both plates comprises a scale marker, either on a surface of or inside the plate, that provide information of a lateral dimension of a structure of the sample and/or the plate.

In some embodiments, one or both plates comprises an imaging marker, either on surface of or inside the plate, that assists an imaging of the sample.

In some embodiments, the spacers functions as a location marker, a scale marker, an imaging marker, or any combination of thereof.

In some embodiments, the average thickness of the layer of uniform thickness is about equal to a minimum dimension of an analyte in the sample.

In some embodiments, the inter-spacer distance is 1 µm or less, 5 µm or less, 7 µm or less, 10 µm or less, 20 µm or less, 30 µm or less, 40 µm or less, 50 µm or less, 60 µm or less, 70 µm or less, 80 µm or less, 90 µm or less, 100 µm or less, 200 µm or less, 300 µm or less, 400 µm or less, or in a range between any two of the values.

In some embodiments, the inter-spacer distance is substantially periodic.

In some embodiments, the inter-spacer distance is aperiodic.

In some embodiments, the spacers are pillars with a cross-sectional shape selected from round, polygonal, circular, square, rectangular, oval, elliptical, or any combination of the same.

In some embodiments, the spacers have are pillar shape and have a substantially flat top surface, wherein, for each spacer, the ratio of the lateral dimension of the spacer to its height is at least 1.

In some embodiments, each spacer has the ratio of the lateral dimension of the spacer to its height is at least 1.

In some embodiments, the minimum lateral dimension of spacer is less than or substantially equal to the minimum dimension of an analyte in the sample.

In some embodiments, the minimum lateral dimension of spacer is in the range of 0.5 um to 100 um.

In some embodiments, the minimum lateral dimension of spacer is in the range of 0.5 um to 10 um.

In some embodiments, the spacers have a density of at least 100/mm2. In some embodiments, the spacers have a density of at least 1000/mm2. In some embodiments, at least one of the plates is transparent.

In some embodiments, at least one of the plates is made from a flexible polymer.

In some embodiments, for a pressure that compresses the plates, the spacers are not compressible and/or, independently, only one of the plates is flexible.

In some embodiments, the flexible plate has a thickness in the range of 10 um to 200 um (e.g. about 10 um, 25 um, 50 um, 75 um, 100 um, 125 um, 150 um, 175 um).

In some embodiments, the variation is less than 30%, 10%, 5%, 3% or 1%.

In some embodiments, the first and second plates are connected and are configured to be changed from the open configuration to the closed configuration by folding the plates.

In some embodiments, the first and second plates are connected by a hinge and are configured to be changed from the open configuration to the closed configuration by folding the plates along the hinge.

In some embodiments, the first and second plates are connected by a hinge that is a separate material to the plates, and are configured to be changed from the open configuration to the closed configuration by folding the plates along the hinge In some embodiments, the first and second plates are made in a single piece of material and are configured to be changed from the open configuration to the closed configuration by folding the plates.

In some embodiments, the layer of uniform thickness sample is uniform over a lateral area that is at least 100 um$^2$.

In some embodiments, the layer of uniform thickness sample is uniform over a lateral area that is at least 1 mm$^2$.

In some embodiments, the device is configured to analyze the sample in 60 seconds or less.

In some embodiments, at the closed configuration, the final sample thickness device is configured to analyze the sample in 60 seconds or less.

In some embodiments, the device further comprises, on one or both of the plates, one or a plurality of amplification sites that are each capable of amplifying a signal from the analyte or a label of the analyte when the analyte or label is within 500 nm from an amplification site.

In some embodiments, at the closed configuration, the final sample thickness device is configured to analyze the sample in 10 seconds or less.

In some embodiments, the dry binding site comprises a capture agent.

In some embodiments, the dry binding site comprises an antibody or nucleic acid. In some embodiments, the releasable dry reagent is a labeled reagent. In some embodiments, the releasable dry reagent is a fluorescently-labeled reagent.

In some embodiments, the releasable dry reagent is a dye. In some embodiments, the releasable dry reagent is a beads. In some embodiments, the releasable dry reagent is a quantum dot. In some embodiments, the releasable dry reagent is a fluorescently-labeled antibody.

In some embodiments, the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

In some embodiments, the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the releasable dry reagent is a cell stain. In some embodiments, the device further comprises a detector that is an optical detector for detecting an optical signal. In some embodiments, the device further comprises a detector that is an electrical detector for detecting an electric signal.

In some embodiments, the device comprises discrete spacers that are not fixed to any of the plates, wherein at the closed configuration, the discrete spacers are between the inner surfaces of the two plates, and the thickness of the sample is confined by the inner surfaces of the two plates, and regulated by the discrete spacers and the plates.

In some embodiments, the device further comprises a binding site that has a chemical sensor that is made from a material selected from the group consisting of: silicon nanowire (Si NW; single-walled carbon nanotubes (SWCNT); random networks of carbon nanotubes (RN-CNTs); molecularly capped metal nanoparticles (MCNPs); metal oxide nanoparticles (MONPs); and chemically sensitive field-effect transistors (CHEM-FETs).

A system is provided herein for rapidly analyzing a vapor condensate sample using a mobile phone comprising:
  (a) a device of any prior claim;
  (b) a mobile communication device comprising:
    i. one or a plurality of cameras for the detecting and/or imaging the vapor condensate sample; and
    ii. electronics, signal processors, hardware and software for receiving and/or processing the detected signal and/or the image of the vapor condensate sample and for remote communication.

In some embodiments, the system further comprise a light source from either the mobile communication device or an external source.

In some embodiments, one of the plates has a binding site that binds an analyte, wherein at least part of the uniform sample thickness layer is over the binding site, and is substantially less than the average lateral linear dimension of the binding site.

In some embodiments, the system further comprising:

(d) a housing configured to hold the sample and to be mounted to the mobile communication device.

In some embodiments, the housing comprises optics for facilitating the imaging and/or signal processing of the sample by the mobile communication device, and a mount configured to hold the optics on the mobile communication device.

In some embodiments, an element of the optics in the housing is movable relative to the housing.

In some embodiments, the mobile communication device is configured to communicate test results to a medical professional, a medical facility or an insurance company.

In some embodiments, the mobile communication device is further configured to communicate information on the test and the subject with the medical professional, medical facility or insurance company.

In some embodiments, the mobile communication device is further configured to communicate information of the test to a cloud network, and the cloud network process the information to refine the test results.

In some embodiments, the mobile communication device is further configured to communicate information of the test and the subject to a cloud network, the cloud network process the information to refine the test results, and the refined test results will send back the subject.

In some embodiments, the mobile communication device is configured to receive a prescription, diagnosis or a recommendation from a medical professional.

Analysis of EBC

Figure 11:
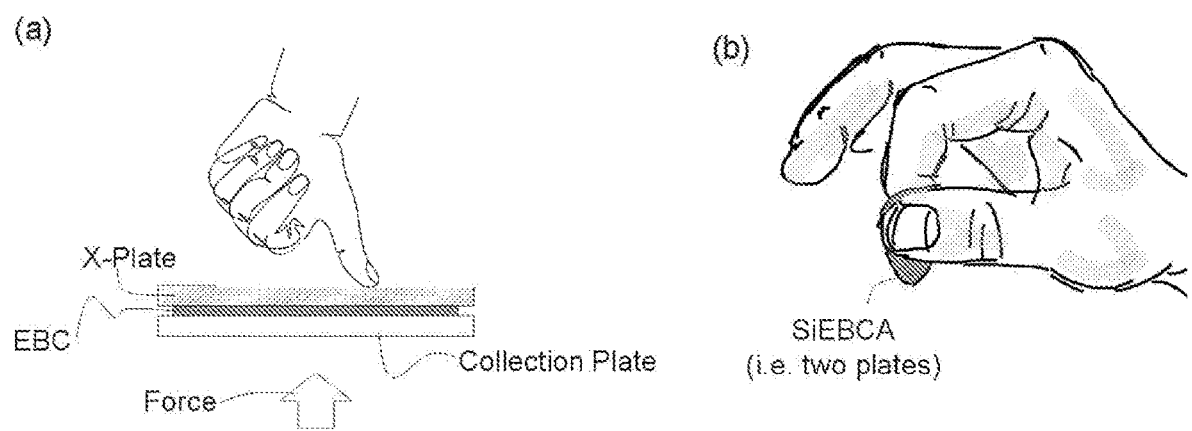
FIG. 11. The surface wetting properties for an untreated and a treated (for better wetting than untreated surface) surface of a collection plate.

Breath tests are among the least invasive methods available for clinical diagnosis, disease state monitoring, health monitoring and environmental exposure assessment. Exemplary methods and devices for analyzing EBC are shown in FIGS. 9-11.

EBC analysis can be used for detection of inflammatory markers, which reflect the state of chronic airways diseases such as chronic obstructive pulmonary disease (COPD), asthma, and cystic fibrosis (CF). EBC analysis can also be used for identification of metabolic, proteomic, and genomic fingerprints of breathing, aiming for an early diagnosis of not only respiratory, but also systemic diseases.

A breath matrix from a subject is a mixture of nitrogen, oxygen, CO2, H2O, and inert gases. The remaining small fraction consists of more than 1000 trace volatile organic compounds (VOCs) with concentrations in the range of parts per million (ppm) to parts per trillion (ppt) by volume. In terms of their origin, these volatile substances may be generated in the body (endogenous) or may be absorbed as contaminants from the environment (exogenous). The composition of VOCs in breath varies widely from person to person, both qualitatively and quantitatively.

Although the number of VOCs found to date in human breath is more than 1000, only a few VOCs are common to all humans. These common VOCs, which include isoprene, acetone, ethane, and methanol, are products of core metabolic processes and are very informative for clinical diagnostics. The bulk matrix and trace VOCs in breath exchange between the blood and alveolar air at the blood-gas interface in the lung. One exception is NO, which is released into the airway in the case of airway inflammation.

The endogenous compounds found in human breath, such as inorganic gases (e.g., NO and CO), VOCs (e.g., isoprene, ethane, pentane, acetone), and other typically nonvolatile substances such as isoprostanes, peroxynitrite, or cytokines, can be measured in breath condensate. Testing for endogenous compounds can provide valuable information concerning a possible disease state. Furthermore, exogenous molecules, particularly halogenated organic compounds, can indicate recent exposure to drugs or environmental pollutants.

Volatile Organic Compounds (VOCs) are organic substances that have a high vapor pressure and therefore evaporate at room temperature. The VOCs that may be assayed as target analytes by the methods and devices provided by the present invention include, but not limited to, biologically generated VOCs (e.g., terpenes, isoprene, methane, green leaf volatiles) and anthropogenic VOCs (e.g., typical solvents used in paints and coatings, like ethyl acetate, glycol ethers, and acetone, vapors from adhesives, paints, adhesive removers, building materials, etc., like methylene chloride, MTBE, and formaldehyde, chlorofurocarbons and perchloroethylene used in dry cleaning, vapor and exhaustive gas from fossil fuels, like benzene and carbon monoxide).

Detailed discussion on certain breath markers for diseases and other health conditions is given in Table 1.

Besides the diseases listed in Table 1, various VOCs contained in exhaled breath have also been linked to different types of cancers. A non-exclusive list of breath VOCs identified as biomarkers for cancers is shown in Table 2.

Besides some of the non-volatile compounds listed in Table 1, various non-volatile compounds have also been lined to or identified as biomarkers of various diseases/conditions. Among these, a particular application of the device and method provided by the present disclosure is to assay the glucose level in EBC. Other applications include, but not limited to, detecting the levels of nitrogen reactive species, arachidonic acid metabolites (e.g., isoprostanes, leukotrienes, prostanoids), cytokines, glutathione, proteins and metabolites, small molecules (e.g., chloride, sodium, potassium, urea, and small organic acids), and pH.

In some embodiments, the devices and methods of the present invention also find applications in the detection of drugs of abuse in EBC sample. The drugs of abuse to be detected using the devices and methods of the present invention include, but not limited to, ethanol, cannabis, methadone, amphetamine, methamphetamine, 3,4-methylenedioxymethamphetamine, codeine, 6-acetylmorphine, diazepam, oxazepam, morphine, benzoylecgonine, cocaine, buprenorphine and tetrahydrocannabinol.

TABLE 1

Breath markers in certain diseases or conditions

| Disease/Condition | Breath Marker |
| --- | --- |
| Diabetes/diabetic ketoacidosis | Acetone, Ethylbenzene, Xylene, Toluene, Ethane, Pentane, Propane, Isoprene, Ethanol, Methanol, Isopropanol, 2,3,4-Trimethylhexane, 2,6,8-Trimethyldecane, Tridecane, Undecane |

TABLE 1-continued

Breath markers in certain diseases or conditions

| Disease/Condition | Breath Marker |
|---|---|
| Helicobacter pylori infection | Ammonia, volatile organic compounds |
| Uremia/kidney failure | Dimethylamine, trimethylamine |
| Liver disease | Dimethylamine, trimethylamine |
| Liver disease | Ethanethiol, dimethylsulfide, hydrogen disulfide |
| Liver cirrhosis | Acetone, styrene, dimethylsulfide, dimethylselene |
| Liver disease/fetor hepaticus | C2-C5 Aliphatic acids, methylmercaptan |
| Angina, ischemic heart disease | Alkanes, methylated alkanes |
| Heart-transplant rejection | Methylated alkane contour |
| Rheumatoid arthritis | Pentane |
| Allograft rejection | CS2 |
| Oxidative stress | NO, CO, nitrosothiol, 8-isoprostane, 4-hydroxy-2-nonenal, malondialdehyde, hydrogen peroxide |
| Chronic obstructive pulmonary disease | NO, CO, nitrosothiol, hydrogen peroxide |
| Rhinitis, rhinorrhea chronic cough | NO |
| Asthma | Pentane, ethane, 8-isoprostane, NO, pH, H2O2, leukotrienes (e.g., LTs, Cys-LTs, LTE4), 8-Isoprostane, PGE2, ILs, IL-4, IL-5, IL-6, IL-8, IL-10, IL-17, INF-☐, RANTES, MIP☐, MIP☐, TNF-☐, TGF-☐, ET-1, Cytokeratine 1, MDA, ADMA, CCL11, hs-CRP, sICAM-1 |
| Cystic fibrosis | NO, CS2, leukotrienes (e.g., LTE4), pH, Nitrotyrosine, Nitrites, Nitric oxide, 8-Isoprostane, IL-6, IL-8, IL-5, TNF-☐ |
| Bronchiectasis | NO |
| Lung cancer | Alkanes, monomethylated alkanes, nitric oxide |
| Lung carcinoma | Acetone, methylethylketone, n-propanol, alkanes, aniline, o-toluidine |
| Breast cancer | 2-propanol, 2,3-dihydro-1-4(1H)-quinazolinone, 1-phenyl-ethanone, heptanal, isopropyl myristate |
| Idiopathic pulmonary fibrosis (IPF) | 8-Isoprostane, H2O2, 3-nitrotyrosine, NOx, docosatetraenoyl-LPA |
| Pulmonary arterial hypertension (PAH) | Natriuretic peptide, pro-BNP, ET-1, 6-keto-PGF1α, 8-isoprostane, IL-6 |
| Sarcoidosis | 8-Isoprostane, Cys-LTs, Neopterin, TGF-☐ |
| Obstructive SleepApnea Syndrome (OSA) | |
| Pediatric patients | 8-Isoprostane, IL-6, LTB4, Cys-LTs, H2O2, Uric salts |
| Adult patients | 8-Isoprostane, IL-6, TNF-☐, pH, H2O2, ICAM-1, IL-8 |
| Systemic Lupus Erythematosus (SLE) | IL-6, IL-8, IL-10 |
| Chronic Renal Disease (CRD) | pH, Nitrites, Nitrates, H2O2 |

TABLE 2

VOCs from exhaled breath that are identified in biomarkers of various cancers

| Disease | Compound name |
|---|---|
| Lung cancer | 1,3-Cyclopentadiene, 1-methyl- |
| | 1-Cyclopentene |
| | 2,3-Butanedione |
| | 2-Butanol, 2,3-dimethyl- |
| | 2-Butanone (methyl ethyl ketone) |
| | 2-Butanone, 3-hydroxy- |
| | 2-Butene, 2-methyl- |
| | 3-Butyn-2-ol |
| | Acetophenone |
| | Benzaldehyde |
| | Benzene, cyclobutyl- |
| | Butane, 2-methyl- |
| | Butyl acetate |
| | Ethylenimine |
| | Isoquinoline, 1,2,3,4-tetrahydro- |
| | Methyl propyl sulfide |
| | n-Pentanal |
| | n-Undecane |
| | Undecane, 3,7-dimethyl- |
| | Urea, tetramethyl- |
| | Cyclopentane |
| | Acetone |
| | Methyl ethyl ketone |
| | n-Propanol |

TABLE 2-continued

VOCs from exhaled breath that are identified in biomarkers of various cancers

| Disease | Compound name |
|---|---|
| | 1,1'-(1-Butenylidene)bis benzene |
| | 1-Methyl-4-(1-methylethyl)benzene |
| | 2,3,4-Trimethyl hexane |
| | 3,3-Dimethyl pentane |
| | Dodecane |
| | 1,3-Butadiene, 2-methyl-(isoprene) |
| | 1-Heptene |
| | 1-Hexene |
| | Benzene |
| | Benzene, 1,2,4-trimethyl- |
| | Benzene, 1,4-dimethyl |
| | Benzene, 1-methylethenyl- |
| | Benzene, propyl- |
| | Cyclohexane |
| | Cyclopentane, methyl- |
| | Cyclopropane, 1-methyl-2-pentyl- |
| | Decane |
| | Heptane, 2,2,4,6,6-pentamethyl |
| | Heptane, 2,4-dimethyl |
| | Heptane, 2-methyl |
| | Hexanal |
| | Methane, trichlorofluoro- |
| | Nonane, 3-methyl- |
| | Octane, 3-methyl- |
| | Styrene (ethenylbenzene) |
| | Undecane |
| | Butane |
| | Decane, 5-methyl |
| | Heptane |
| | Hexane, 2-methyl |
| | Hexane, 3-methyl |
| | Octane, 4-methyl |
| | Pentane |
| | Tridecane, 3-methyl |
| | Tridecane, 7-methyl |
| | 1,1-Biphenyl, 2,2-diethyl- |
| | 1,2-Benzenedicarboxylic acid, diethyl ester |
| | 1,5,9-Cyclododecatriene, 1,5,9-trimethyl- |
| | 10,11-Dihydro-5H-dibenz[b,f]azepine |
| | 1H-Indene, 2,3-dihydro-1,1,3-trimethyl-3-phenyl- |
| | 1-Propanol |
| | 2,4-Hexadiene, 2,5-dimethyl- |
| | 3-Pentanone, 2,4-dimethyl- |
| | 2,5-Cyclohexadiene-1,4-dione, 2,6-bis(1,1-dimethylethyl)- |
| | Benzene, 1,1-oxybis- |
| | Benzoic acid, 4-ethoxy-, ethyl ester |
| | Decane, 4-methyl- |
| | Furan, 2,5-dimethyl- |
| | Pentan-1,3-dioldiisobutyrate, 2,2,4-trimethyl |
| | Propanoic acid, 2-methyl-, 1-(1,1-dimethylethyl)-2-methyl-1,3-propanediyl ester |
| | trans-Caryophyllene |
| | 1,2,4,5-Tetroxane, 3,3,6,6-tetraphenyl- |
| | 1H-Indene, 2,3-dihydro-4-methyl- |
| | 1-Propene, 1-(methylthio)-, (E)- |
| | 2,2,4-Trimethyl-1,3-pentanediol diisobutyrate |
| | 2,2,7,7-Tetramethyltricyclo-[6.2.1.0(1,6)]undec-4-en-3-one |
| | 2,3-Hexanedione |
| | 2,5-Cyclohexadien-1-one, 2,6-bis(1,1-dimethylethyl)-4-ethylidene |
| | 2-Methyl-3-hexanone |
| | 4-Penten-2-ol |
| | 5,5-Dimethyl-1,3-hexadiene |
| | 5-Isopropenyl-2-methyl-7-oxabicyclo[4.1.0]heptan-2-ol |
| | 9,10-Anthracenediol, 2-ethyl- |
| | Anthracene, 1,2,3,4-tetrahydro-9-propyl- |
| | Benzene, 1,1-(1,2-cyclobutanediyl)bis,cis- |
| | Benzene, 1,1-[1-(ethylthio)propylidene]bis- |
| | Benzene, 1,1-ethylidenebis, 4-ethyl- |
| | Benzophenone |
| | Bicyclo[3.2.2]nonane-1,5-dicarboxylic acid, 5-ethyl ester |
| | Camphor |
| | Ethane, 1,1,2-trichloro-1,2,2-trifluoro- |
| | Furan, 2-[(2-ethoxy-3,4-dimethyl-2-cyclohexen-1-ylidene)methyl]- |
| | Isomethyl ionone |
| | Isopropyl alcohol |
| | Pentanoic acid, 2,2,4-trimethyl-3-carboxyisopropyl, isobutyl ester |

TABLE 2-continued

VOCs from exhaled breath that are identified in biomarkers of various cancers

| Disease | Compound name |
|---|---|
| | Propane, 2-methoxy-2-methyl- |
| | α-Isomethyl ionone |
| | Butanal |
| | Heptanal |
| | Nonanal |
| | Octanal |
| | Pentanal |
| | Propanal |
| | Ethylbenzene |
| | Octane |
| | Pentamethylheptane |
| | Toluene |
| | 2-Methylpentane |
| | Isoprene |
| | Xylenes total |
| | Styrene |
| | Aniline |
| | o-Toluidine |
| | 1-Butanol |
| | 3-Hydroxy-2-butanone |
| | 2,6,10-Trimethyltetradecane |
| | 2,6,11-Trimethyldodecane |
| | 2,6-Dimethylnaphthalene |
| | 2,6-Di-tert-butyl-, 4-methylphenol |
| | 2-Methylhendecanal |
| | 2-Methylnaphthalene |
| | 2-Pentadecanone |
| | 3,7-Dimethylpentadecane |
| | 3,8-Dimethylhendecane |
| | 4-Methyltetradecane |
| | 5-(1-Methyl)propylnonane |
| | 5-(2-Methyl)propylnonane |
| | 5-Butylnonane |
| | 5-Propyltridecane |
| | 7-Methylhexadecane |
| | 8-Hexylpentadecane |
| | 8-Methylheptadecane |
| | Eicosane |
| | Hexadecanal |
| | Nonadecane |
| | Nonadecanol |
| | Tridecane |
| | Tridecanone |
| | Formaldehyde (methanal) |
| | Isopropanol |
| Breast cancer | 2,3,4-Trimethyldecane |
| | 2-Amino-5-isopropyl-8-methyl-1-azulenecarbonitrile |
| | 3,3-Dimethyl pentane |
| | 5-(2-Methylpropyl)nonane |
| | 6-Ethyl-3-octyl ester 2-trifluoromethyl benzoic acid |
| | Nonane |
| | Tridecane, 5-methyl |
| | Undecane, 3-methyl |
| | Pentadecane, 6-methyl |
| | Propane, 2-methyl |
| | Nonadecane, 3-methyl |
| | Dodecane, 4-methyl |
| | Octane, 2-methyl |
| | 1-Phenylethanone |
| | 2,3-Dihydro-1-phenyl-4(1H)-quinazolinone |
| | 2-Propanol |
| | Heptanal |
| | Isopropyl myristate |
| | (+)-Longifolene |
| | 1,3-Butadiene, 2-methyl- |
| | 1,4-Pentadiene |
| | 1H-Cycloprop[e]azulene, decahydro-1,1,7-trimethyl-4-methylene- |
| | 1-Octanol, 2-butyl- |
| | 2,5-Cyclohexadiene-1,4-dione, 2,6-bis(1,1-dimethylethyl)- |
| | 2,5-Di-tert-butyl-1,4-benzoquinone |
| | 2-Hexyl-1-octanol |
| | 3-Ethoxy-1,1,1,5,5,5-hexamethyl-3-(trimethylsiloxy)trisiloxane |
| | Acetic acid, 2,6,6-trimethyl-3-methylene-7-(3-oxobutylidene)oxepan-2-yl ester |
| | Benzene, 1,2,3,5-tetramethyl- |
| | Benzene, 1,2,4,5-tetramethyl- |

TABLE 2-continued

VOCs from exhaled breath that are identified in biomarkers of various cancers

| Disease | Compound name |
|---|---|
| | Benzene, 1-ethyl-3,5-dimethyl- |
| | Benzoic acid, 4-methyl-2-trimethylsilyloxy-, trimethylsilyl ester |
| | Cyclohexene, 1-methyl-5-(1-methylethenyl)- |
| | Cyclohexene, 1-methyl-5-(1-methylethenyl)-, (R)- |
| | Cyclopropane, ethylidene |
| | Cyclotetrasiloxane, octamethyl- |
| | D-Limonene |
| | Dodecane |
| | Dodecane, 2,6,11-trimethyl- |
| | Dodecane, 2,7,10-trimethyl- |
| | Longifolene-(V4) |
| | Pentadecane |
| | Tetradecane |
| | Tridecane |
| | Trifluoroacetic acid, n-octadecyl ester |
| | Undecane |
| Colon cancer | 1,1'-(1-Butenylidene)bis benzene |
| | 1,3-Dimethylbenzene |
| | 4-(4-Propylcyclohexyl)-4'-cyano[1,1'-biphenyl]-4-yl ester benzoic acid |
| | 2-Amino-5-isopropyl-8-methyl-1-azulenecarbonitrile |
| | [(1,1-Dimethylethyl)thio]acetic acid |
| Esophagogastric cancer | Ethylphenol |
| | Hexanoic acid |
| | Methylphenol |
| | Phenol |
| Gastric cancer | 2-Butoxyethanol |
| | Isoprene |
| | 2-Propenenitrile |
| | 6-Methyl-5-hepten-2-one |
| | Furfural (furfuraldehyde) |
| Head and neck cancer | 4,6-Dimethyldodecane |
| | 5-Methyl-3-hexanone |
| | 2,2-Dimethyldecane |
| | Limonene |
| | 2,2,3-Trimethyl-exobicyclo[2.2.1]heptane |
| | 2,2-Dimethyl-propanoic acid |
| | Ammonium acetate |
| | 3-Methylhexane |
| | 2,4-Dimethylheptane |
| | 4-Methyloctane |
| | p-Xylene |
| | 2,6,6-Trimethyloctane |
| | 3-Methylnonane |
| Liver cancer | 3-Hydroxy-2-butanone |
| | Styrene |
| | Decane |
| Ovarian cancer | Decanal |
| | Nonanal |
| | Styrene |
| | 2-Butanone |
| | Hexadecane |
| Prostate cancer | Toluene |
| | p-Xylene |
| | 2-Amino-5-isopropyl-8-methyl-1-azulenecarbonitrile |
| | 2,2-Dimethyldecane |

EBC-3.2. Collection and Analysis of Other Vapor Condensates.

Certain embodiments of the present invention are related to the applications of the SiEBCA methods and devices for collection and analysis of the vapor condensates other than the EBC. The other moistures include, but not limited to, fog, clouds, steams, etc. The target analysis of these vapor condensates can be for different purpose environmental monitoring, emission control, etc. In some embodiments, the sample is a vapor from a biological sample, an environmental sample, a chemical sample, or clinical sample.

EBC-3.3. Automatic and High Throughput.

In certain embodiments, the devices and methods of the present invention are automatic and high speed, where the steps are performed by machines. In some embodiments, the plates are in the form of roll of sheets and are controlled by rollers to put certain area of the plates into an open configuration or a closed configuration.

EBC-3.4. Identification and Validation of Markers in Vapor Condensate

In certain embodiments, the devices and methods of the present invention are particularly useful for the identification and validation of biomarkers for human diseases/conditions, or other markers for environmental, food safety, or other conditions/events. Due to the ease, fast speed, small sample volume, and multiplexing potential of the present devices and methods, it is easy to adapt the present device for high-throughput and even automatic screening and validation of these markers. In certain embodiments, the present devices and methods are particularly useful when coupled with data processing system capable of pattern recognition for such purposes.

In certain embodiments, the devices and methods of the present invention are also advantageous to create large sample dataset for refining the algorithms for pattern recognition through machine learning and/or other methodologies.

EBC-4. EBC Collection and Analysis Without Spacers

Another aspect of the present invention is to provide devices and methods for collecting and analyzing vapor condensate using the aforementioned collection plate and cover plate but without spacers.

In some embodiments of the present invention, the spacers that are used to regulate the sample or a relevant volume of the EBC sample are replaced by (a) positioning sensors that can measure the plate inner spacing, and/or (b) devices that can control the plate positions and move the plates into a desired plate inner spacing based on the information provided the sensors. In some embodiment, all the spacers are replaced by translation stage, monitoring sensors and feedback system.

In some embodiments, the collection plate and the cover plate comprise no spacers at all, and the EBC sample is compressed by the two plates into a thin layer, the thickness of which is regulated by the spacing between the inner surfaces of the plates (the plate spacing).

A4. A Device for Collecting EBC Without Spacers, Comprises:
  a first plate and a second plate, wherein:
    i. the plates are movable relative to each other into different configurations, and one or both plates are flexible;
    ii. both plates comprise a sample contact area on the respective surface of each plate for contacting EBC sample;
  wherein one of the configurations is an open configuration, in which: the two plates are separated apart, and the EBC sample is deposited on one or both of the plates from a subject; and
  wherein another of the configurations is a closed configuration which is configured after the EBC sample deposition in the open configuration; and in the closed configuration: at least part of the EBC sample is compressed by the two plates into a thin layer, wherein the thin layer is in contact with and confined by the inner surfaces of the two plates.

A5. A Method of Collecting EBC Without Spacers, Comprises the Steps:
  (a) obtaining a collection plate and a cover plate of paragraph A4;
  (b) depositing, when the plates are configured in the open configuration, an EBC sample by exhaling breath from a subject toward the collection plate, wherein the exhaled breath condensates on a collection surface of the collection plate to form droplets and/or puddles that have different lateral sizes and different heights, depending upon the surface wetting properties of the collection surface;
  (c) after (b), bringing the cover plate over the collection surface and then bringing the two plates into a closed configuration by pressing the plates, wherein at the closed configuration:
    (i) at least a part of the EBC sample is between the cover plate and the collection plate, and a relevant area of the collection surface of the collection plate is covered by the cover plate; and
    (ii) in the relevant area, a substantial number or all of the droplets or puddles formed in step (b) at the open configuration merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced; and
  wherein the plate spacing is the spacing between the inner surfaces of the cover plate and the collection plate, the relevant area is a portion or entire surface of the collection surface, and the collection surface is a portion or entire surface of the collection plate.

A6. A method of analyzing EBC without spacers, comprises the steps:
  (a) obtaining a collection plate and a cover plate of paragraph A4;
  (b) depositing, when the plates are configured in the open configuration, an EBC sample by exhaling breath from a subject toward the collection plate, wherein the exhaled breath condensates on a collection surface of the collection plate to form droplets and/or puddles that have different lateral sizes and different heights, depending upon the surface wetting properties of the collection surface;
  (c) after (b), bringing the cover plate over the collection surface and then bringing the two plates into a closed configuration by pressing the plates, wherein at the closed configuration:
    (i) at least a part of the EBC sample is between the cover plate and the collection plate, and a relevant area of the collection surface of the collection plate is covered by the cover plate; and
    (ii) in the relevant area, a substantial number or all of the droplets or puddles formed in step (b) at the open configuration merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced; and
  (d) analyzing the EBC,
  wherein the plate spacing is the spacing between the inner surfaces of the cover plate and the collection plate, the relevant area is a portion or entire surface of the collection surface, and the collection surface is a portion or entire surface of the collection plate.

In some embodiments, it is unlikely to obtain a layer of highly uniform thickness without using the spacers as discussed in the foregoing sessions. However, it is still advantageous to use the device and method of paragraphs A4-A5 for collecting and analyzing EBC sample, for it is easy, rapid to handle, requires no professional training and a very small volume of sample.

In some embodiments, the analyzing step (d) of paragraph A6 comprises determining the thickness of the collected EBC sample at the closed configuration after the formation of the thin layer during step (c). In some embodiments, the thickness of the collected EBC sample at the closed configuration is equal to the spacing between the inner surfaces of the two plates.

In some embodiments, measuring the spacing between the inner surfaces comprises the use of optical interference. The optical interference can use multiple wavelength. For example, the light signal due to the interference of a light reflected at the inner surface of the first plate and the second plate oscillate with the wavelength of the light. From the oscillation, one can determine the spacing between the inner surfaces. To enhance the interference signal, one of the inner surfaces or both can be coated with light reflection material.

In some embodiments, measuring the spacing between the inner surfaces comprises taking optical imaging (e.g. taking a 2D (two-dimensional)/3D (three-dimensional) image of the sample and the image taking can be multiple times with different viewing angles, different wavelength, different phase, and/or different polarization) and image processing.

In some embodiments, the analyzing step (d) of paragraph A6 comprises measuring the volume of the collected EBC sample based on the lateral area and the thickness of the thin layer that are determined after the formation of the thin layer during step (c).

In some embodiments, measuring the entire sample area or volume comprises taking optical imaging (e.g. taking a 2D (two-dimensional)/3D (three-dimensional) image of the sample and the image taking can be multiple times with different viewing angles, different wavelength, different phase, and/or different polarization) and image processing. The sample lateral area means the area in the direction approximately parallel to the first plate and the second plate. The 3D imaging can use the method of fringe projection profilometry (FPP), which is one of the most prevalent methods for acquiring three-dimensional (3D) images of objects.

In some embodiments, the measuring of the sample area or volume by imaging comprises: (a) calibration of the image scale by using a sample of the known area or volume (e.g., The imager is a smartphone and the dimensions of the image taken by the phone can be calibrated by comparing an image of the a sample of known dimension taken the same phone); (b) comparison of the image with the scale markers (rulers) placed on or near the first plate and second plate (discussed further herein), and (c) a combination of thereof.

As used herein, light may include visible light, ultraviolet light, infrared light, and/or near infrared light. Light may include wavelengths in the range from 20 nm to 20,000 nm.

In some embodiments, the pressing during step (c) of paragraphs A5-A6 is performed by human hand.

In some embodiments, the formation and properties of the thin layer is dependent on the pressing force applied during step (c) of paragraphs A5-A6 for bringing the two plates into the closed configuration. In some embodiments, the pressing force applied during step (c) of paragraphs A5-A6 is well adjusted for forming a thin layer of EBC sample between the two plates that has prerequisite parameters.

More Examples of EBC Collection and Analysis Experiments

Additional exemplary experimental testing and observation, and additional preferred embodiments of the present invention are given.

All the exemplary experimental testing and demonstration of the present invention described in Section 4 (Examples) were performed under the following conditions and share the following common observations.

Plates. Only one of the two plates of SiEBCA device, termed "X-Plate", has the spacers fixed on the sample surface of the plate, and the other plate, termed "the substrate plate", has a planar surface and does not have spacers.

EBC Formation With No Spacers at Open and Closed Configurations

In a separate set of experiments, we tested the possibility of collecting EBC samples using plates with no spacers.

As presented here, the exemplary SiEBCA device also comprises a collection plate and a cover plate, while the collection plate we used was 25 mm×25 mm×1 mm PMMA planar plate with untreated surfaces, and the cover plate was 25 mm×25 mm×0.175 mm PMMA planar plate with bare untreated surfaces. The EBC sample was collected by having a subject breathe on a collection plate for 2 sec and a cover plate was immediately brought to cover the collection plate and pressed against it as described above. Later, the SiEBCA together with the sample collected therein were subject to optical measurement and microscopy imaging.

FIG. 15 in U.S. Provisional Patent Application 62/459, 972, filed on Feb. 16, 2017, which is herein incorporated by reference in its entirety, schematically illustrates the optical measurement and imaging taken for the measurement of the EBC sample thickness and lateral area, respectively. As shown in panel (A), Fabry-Pérot interferometer was used to measure the F-P cavity resonance in the reflectance spectra at 25 points on the 4×4 grid artificially generated in the center of the SiEBCA device, from which the plate spacing (and the sample thickness) is thus deduced. Each of the 25 measuring points is about 2 um by 2 um in area, and all 25 points cover an area of 20 mm by 20 mm. An average plate spacing over the 25 points was taken as the estimate of the sample thickness ($\widetilde{T_{EBC}}$). As shown in panel (B), a direct photo of the SiEBCA device was taken to delineate the general contour of the EBC sample between the two plates and measure the overall lateral area ($S_t$). Then microscopic images were taken at each of the 25 points (each image covers an area $S_i$ of 1.6 mm×1.1 mm), and then these images were analyzed by an image processing software to recognize and measure the total area of the air bubbles ($S_b$) in each image.

To estimate the total EBC sample lateral area, first, the percentage of EBC liquid lateral area ($a_i$) for each measuring point is calculated as (Si−Sb)/Si×100%; second, an average value ($\tilde{a}$) is taken from all 25 points; and finally, the total EBC sample lateral area ($S_{EBC}$) is estimated as $S_t * \tilde{a}$.

The volume of the EBC sample ($V_{EBC}$) is thus determined as $S_{EBC} * \widetilde{T_{EBC}}$.

FIG. 16 in U.S. Provisional Patent Application 62/459, 972, filed on Feb. 16, 2017, which is herein incorporated by reference in its entirety, demonstrates the principle of plate spacing measurement based on F-P cavity resonance. Panel (a) shows the schematic of F-P cavity from the SiEBCA device; panel (b) shows the typical reflectance spectrum and resonances from the device. The plate spacing (h) at each measuring point is calculated as:

$$h = \frac{c}{2n\Delta v}$$

where h is the plate spacing, c is light speed, $\Delta v$ is the period in frequency domain and n is the reflective index of the EBC liquid.

As described above, the average EBC sample thickness is equal to $$\frac{\sum_{1}^{25} h}{25}.$$

EBC sample thickness uniformity is calculated as $$\sqrt{\frac{\sum_{1}^{25}(h-H)^2}{25}}.$$

FIG. 17 in U.S. Provisional Patent Application 62/459,972, filed on Feb. 16, 2017, which is herein incorporated by reference in its entirety, shows microscopic images of the EBC sample collected using the exemplary SiEBCA device without spacers. Panels (a)-(b) respectively show the images of the EBC samples at the closed configuration after hand pressing the two plates with low, medium, and high pressing strength. Low strength was less than 10 kg, high strength was higher than 15 kg, and medium strength was in between the low and high strength.

Under these three different conditions, the performance of the exemplary SiEBCA device without spacers was examined and summarized in Table 3, based on the measurement and calculation methods described above. As shown in Table 3 and FIG. 17, low strength gives thicker liquid thickness with larger bubble area, while high strength gives thinner EBC sample layer with smaller bubble area.

TABLE 3

Performance of SiEBCA without spacers

| Press Strength | Average EBC area percentage ã | EBC Area $S_{EBC}$ (mm²) | Average EBC thickness $\widetilde{T_{EBC}}$ (um) | Collected EBC volume $V_{EBC}$ (uL) | EBC thickness uniformity |
|---|---|---|---|---|---|
| 1 Low | 38% | 240 | 1.45 | 0.35 | 58% |
| 2 Medium | 72% | 450 | 0.87 | 0.39 | 47% |
| 3 High | 98% | 620 | 0.51 | 0.32 | 43% |

AA0. A device for collecting and analyzing vapor condensate (VC) sample, comprising:
a collection plate and a cover plate, wherein:
i. the plates are movable relative to each other into different configurations;
ii. one or both plates are flexible; and
iii. each of the plates has, on its inner respective surface, a sample contact area for contacting a vapor condensate (VC) sample that contains an analyte;
wherein one of the configurations is an open configuration, in which: the two plates are either completely or partially separated apart, and the VC sample is deposited on one or both of the plates; and
wherein another of the configurations is a closed configuration which is configured after the VC sample deposition in the open configuration; and in the closed configuration: at least a part of the VC sample is between the two plates and in contact with the two plates, and has a thickness that is regulated by the two sample surfaces of the plates and is equal to or less than 30 □m with a small variation.

AA1. A device for collecting and analyzing vapor condensate (VC) sample, comprising:
a collection plate, a cover plate, and spacers, wherein:
i. the plates are movable relative to each other into different configurations;
ii. one or both plates are flexible;
iii. each of the plates has, on its respective inner surface, a sample contact area for contacting a vapor condensate (VC) sample that contains an analyte;
iv. the spacers are fixed to the respective inner surface of one or both of the plates and have a predetermined substantially uniform height and a predetermined constant inter-spacer distance and wherein at least one of the spacers is inside the sample contact area;
wherein one of the configurations is an open configuration, in which: the two plates are either completely or partially separated apart, the spacing between the plates is not regulated by the spacers, and the VC sample is deposited on one or both of the plates; and
wherein another of the configurations is a closed configuration which is configured after the VC sample deposition in the open configuration; and in the closed configuration: at least a part of the VC sample is between the two plates and in contact with the two plates, and has a highly uniform thickness that is regulated by the spacers and the two sample surfaces of the plates and is equal to or less than 30 □m with a small variation.

AA2. The device of embodiment AA0 or AA1, wherein the device further comprises a dry reagent coated on one or both of the plates.

AA3. The device of any prior embodiment, wherein the device further comprises, on one or both plates, a dry binding site that has a predetermined area, wherein the dry binding site binds to and immobilizes an analyte in the sample.

AA4. The device of any prior embodiment, wherein the device further comprises, on one or both plates, a releasable dry reagent and a release time control material that delays the time that the releasable dry regent is released into the sample.

AA5. The device of embodiment 4, wherein the release time control material delays the time that the dry regent starts is released into the sample by at least 3 seconds.

AA6. The device of any prior embodiment, wherein the device further comprises, on one or both plates, one or a plurality of dry binding sites and/or one or a plurality of reagent sites.

AA7. The device of any prior embodiment, wherein the sample is exhale breath condensate.

AA8. The device of any prior embodiment, wherein the sample is a vapor from a biological sample, an environmental sample, a chemical sample, or clinical sample.

AA9. The device of any prior embodiment, wherein the analyte comprises a molecule (e.g., a protein, peptides, DNA, RNA, nucleic acid, or other molecules), cells, tissues, viruses, and nanoparticles with different shapes.

AA10. The device of any prior embodiment, wherein the analyte comprises volatile organic compounds (VOCs).

AA11. The device of any prior embodiment, wherein the analyte comprises nitrogen, oxygen, CO2, H2O, and inert gases.

AA12. The device of any prior embodiment, wherein the analyte is stained.

AA13. The device of any prior embodiment, wherein on one of the sample surface, it further comprises an enclosure-spacer that encloses a partial or entire VC samples deposited on the collection plate.

AA14. The device of any prior embodiment, wherein the highly uniform thickness has a value equal to or less than 0.5 um.

AA15. The device of any prior embodiment, wherein the highly uniform thickness has a value in the range of 0.5 um to 1 um.

AA16. The device of any prior embodiment, wherein the highly uniform thickness has a value in the range of 1 um to 2 um.

AA17. The device of any prior embodiment, wherein the highly uniform thickness has a value in the range of 2 um to 10 um.

AA18. The device of any prior embodiment, wherein the highly uniform thickness has a value in the range of 10 um to 20 um.

AA19. The device of any prior embodiment, wherein the highly uniform thickness has a value in the range of 20 um to 30 um.

AA20. The device of any prior embodiment, wherein the thickness of the at least a part of VC sample at the closed configuration is larger than the thickness of VC sample deposited on the collection plate at an open configuration.

AA21. The device of any prior embodiment, wherein the thickness of the at least a part of VC sample at the closed configuration is less than the thickness of VC sample deposited on the collection plate at an open configuration.

AA22. The device of any prior device embodiment, wherein the spacers are fixed on a plate by directly embossing the plate or injection molding of the plate.

AA23. The device of any prior device embodiment, wherein the materials of the plate and the spacers are selected from polystyrene, PMMA, PC, COC, COP, or another plastic.

AA24. The device of any prior embodiment, wherein the inter-spacer spacing is in the range of 1 um to 200 um.

AA25. The device of any prior embodiment, wherein the inter-spacer spacing is in the range of 200 um to 1000 um.

AA26. The device of any prior embodiment, wherein the VC sample is an exhaled breath condensate from a human or an animal.

AA27. The device of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.

AA28. The device of any prior embodiment, wherein for spacers regulating the layer of uniform thickness, the Young's modulus of the spacers times the filling factor of the spacers is equal to or larger than 10 MPa, wherein the filling factor is the ratio of the spacer area in contact with the layer of uniform thickness to the total plate area in contact with the layer of uniform thickness.

AA29. The device of any prior embodiment, wherein for a flexible plate, the thickness of the flexible plate times the Young's modulus of the flexible plate is in the range 60 to 750 GPa-um.

AA30. The device of any prior embodiment, wherein for a flexible plate, the fourth power of the inter-spacer-distance (ISD) divided by the thickness of the flexible plate (h) and the Young's modulus (E) of the flexible plate, ISD4/(hE), is equal to or less than 106 um3/GPa, AA31. The device of any prior paragraph, wherein one or both plates comprises a location marker, either on a surface of or inside the plate, that provides information of a location of the plate.

AA32. The device of any prior paragraph, wherein one or both plates comprises a scale marker, either on a surface of or inside the plate, that provides information of a lateral dimension of a structure of the sample and/or the plate.

AA33. The device of any prior embodiment, wherein one or both plates comprises an imaging marker, either on surface of or inside the plate, that assists an imaging of the sample.

AA34. The device of any prior embodiment, wherein the spacers function as a location marker, a scale marker, an imaging marker, or any combination of thereof.

AA35. The device of any prior embodiment, wherein the average thickness of the layer of uniform thickness is about equal to a minimum dimension of an analyte in the sample.

AA36. The device of any prior embodiment, wherein the inter-spacer distance is in the range of 1 □m to 50 □m.

AA37. The device of any prior embodiment, wherein the inter-spacer distance is in the range of 50 □m to 120 □m.

AA38. The device of any prior embodiment, wherein the inter-spacer distance is in the range of 120 □m to 200 □m.

AA39. The device of any prior embodiment, wherein the inter-spacer distance is substantially periodic.

AA40. The device of any prior embodiment, wherein the inter-spacer distance is aperiodic.

AA41. The device of any prior embodiment, wherein the spacers are pillars with a cross-sectional shape selected from round, polygonal, circular, square, rectangular, oval, elliptical, or any combination of the same.

AA42. The device of any prior embodiment, wherein the spacers have a pillar shape and have a substantially flat top surface, wherein, for each spacer, the ratio of the lateral dimension of the spacer to its height is at least 1.

AA43. The device of any prior embodiment, wherein each spacer has a ratio of the lateral dimension of the spacer to its height at least 1.

AA44. The device of any prior embodiment, wherein the minimum lateral dimension of spacer is less than or substantially equal to the minimum dimension of an analyte in the sample.

AA45. The device of any prior embodiment, wherein the minimum lateral dimension of spacer is in the range of 0.5 um to 100 um.

AA46. The device of any prior embodiment, wherein the minimum lateral dimension of spacer is in the range of 0.5 um to 10 um.

AA47. The device of any prior embodiment, wherein the spacers have a density of at least $100/mm^2$.

AA48. The device of any prior embodiment, wherein the spacers have a density of at least $1000/mm^2$.

AA49. The device of any prior embodiment, wherein at least one of the plates is transparent.

AA50. The device of any prior embodiment, wherein at least one of the plates is made from a flexible polymer.

AA51. The device of any prior embodiment, wherein, for a pressure that compresses the plates, the spacers are not compressible and/or, independently, only one of the plates is flexible.

AA52. The device of any of any prior embodiment, wherein the flexible plate has a thickness in the range of 10 □m to 200 □m.

AA53. The device of any prior embodiment, wherein the variation is less than 30%.
AA54. The device of any prior embodiment, wherein the variation is less than 10%.
AA55. The device of any prior embodiment, wherein the variation is less than 5%.
AA56. The device of any prior embodiment, wherein the first and second plates are connected and are configured to be changed from the open configuration to the closed configuration by folding the plates.
AA57. The device of any prior embodiment, wherein the first and second plates are connected by a hinge and are configured to be changed from the open configuration to the closed configuration by folding the plates along the hinge.
AA58. The device of any prior embodiment, wherein the first and second plates are connected by a hinge that is a separate material to the plates, and are configured to be changed from the open configuration to the closed configuration by folding the plates along the hinge.
AA59. The device of any prior embodiment, wherein the first and second plates are made in a single piece of material and are configured to be changed from the open configuration to the closed configuration by folding the plates.
AA60. The device of any prior embodiment, wherein the layer of uniform thickness sample is uniform over a lateral area that is at least 100 um$^2$.
AA61. The device of any prior embodiment, wherein the layer of uniform thickness sample is uniform over a lateral area that is at least 1 mm$^2$.
AA62. The device of any prior embodiment, wherein the device is configured to analyze the sample in 60 seconds or less.
AA63. The device of any prior embodiment, wherein at the closed configuration, the final sample thickness device is configured to analyze the sample in 60 seconds or less.
AA64. The device of any prior embodiment, wherein the device further comprises, on one or both of the plates, one or a plurality of amplification sites that are each capable of amplifying a signal from the analyte or a label of the analyte when the analyte or label is within 500 nm from an amplification site.
AA65. The device of any prior embodiment, wherein at the closed configuration, the final sample thickness device is configured to analyze the sample in 10 seconds or less.
AA66. The device of any prior embodiment, wherein the dry binding site comprises a capture agent.
AA67. The device of any prior embodiment, wherein the dry binding site comprises an antibody or nucleic acid.
AA68. The device of any prior embodiment, wherein the releasable dry reagent is a labeled reagent.
AA69. The device of any prior embodiment, wherein the releasable dry reagent is a fluorescently-labeled reagent.
AA70. The device of any prior embodiment, wherein the releasable dry reagent is a fluorescently-labeled antibody.
AA71. The device of any prior embodiment, wherein the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.
AA72. The device of any prior embodiment, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.
AA73. The device of any prior embodiment, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.
AA74. The device of any prior embodiment, wherein the releasable dry reagent is a cell stain.
AA75. The device of any prior embodiment, wherein the device further comprises a detector that is an optical detector for detecting an optical signal.
AA76. The device of any prior embodiment, wherein the device further comprises a detector that is an electrical detector for detecting an electric signal.
AA77. The device of any prior embodiment, wherein the device comprises discrete spacers that are not fixed to any of the plates, wherein at the closed configuration, the discrete spacers are between the inner surfaces of the two plates, and the thickness of the sample is confined by the inner surfaces of the two plates, and regulated by the discrete spacers and the plates.
AA78. The device of any prior embodiment, wherein the device further comprises a binding site that has a chemical sensor that is made from a material selected from the group consisting of: silicon nanowire (Si NW); single-walled carbon nanotubes (SWCNT); random networks of carbon nanotubes (RN-CNTs); molecularly capped metal nanoparticles (MCNPs); metal oxide nanoparticles (MONPs); and chemically sensitive field-effect transistors (CHEM-FETs).
BB1. A system for rapidly analyzing a vapor condensation sample using a mobile phone comprising:
(a) a device of any prior AA embodiment;
(b) a mobile communication device comprising:
i. one or a plurality of cameras for the detecting and/or imaging the vapor condensate sample; and
ii. electronics, signal processors, hardware and software for receiving and/or processing the detected signal and/or the image of the vapor condensate sample and for remote communication.
BB2. The system of any prior BB embodiment, wherein the system further comprise a light source from either the mobile communication device or an external source.
BB3. The system of any prior BB embodiment, wherein one of the plates has a binding site that binds an analyte, wherein at least part of the uniform sample thickness layer is over the binding site, and is substantially less than the average lateral linear dimension of the binding site.
BB4. The system of any prior BB embodiment, further comprising:
(d) a housing configured to hold the sample and to be mounted to the mobile communication device.
BB5. The system of any prior BB embodiment, wherein the housing comprises optics for facilitating the imaging and/or signal processing of the sample by the mobile communication device, and a mount configured to hold the optics on the mobile communication device.

BB6. The system of any prior BB embodiment, wherein an element of the optics in the housing is movable relative to the housing.

BB7. The system of any prior BB embodiment, wherein the mobile communication device is configured to communicate test results to a medical professional, a medical facility or an insurance company.

BB8. The system of any prior BB embodiment, wherein the mobile communication device is further configured to communicate information on the test and the subject with the medical professional, medical facility or insurance company.

BB9. The system of any prior BB embodiment, wherein the mobile communication device is further configured to communicate information of the test to a cloud network, and the cloud network process the information to refine the test results.

BB10. The system of any prior BB embodiment, wherein the mobile communication device is further configured to communicate information of the test and the subject to a cloud network, the cloud network process the information to refine the test results, and the refined test results will send back the subject.

BB11. The system of any prior BB embodiment, wherein the mobile communication device is configured to receive a prescription, diagnosis or a recommendation from a medical professional.

BB12. The system of any prior BB embodiment, wherein the mobile communication device is configured with hardware and software to:

(a) capture an image of the sample;
(b) analyze a test location and a control location in in image; and
(c) compare a value obtained from analysis of the test location to a threshold value that characterizes the rapid diagnostic test.

BB13. The system of any prior BB embodiment, wherein at least one of the plates comprises a storage site in which assay reagents are stored.

BB14. The system of any prior BB embodiment, at least one of the cameras reads a signal from the CROF device.

BB15. The system of any prior BB embodiment, wherein the mobile communication device communicates with the remote location via a wifi or cellular network.

BB16. The system of any prior BB embodiment, wherein the mobile communication device is a mobile phone.

CC1. A method for rapidly analyzing an analyte in a sample using a mobile phone, comprising:

(a) depositing a sample on the device of any prior BB embodiment;
(b) assaying an analyte in the sample deposited on the device to generate a result; and
(c) communicating the result from the mobile communication device to a location remote from the mobile communication device.

CC2. The method of any prior CC embodiment, wherein the analyte comprises a molecule (e.g., a protein, peptides, DNA, RNA, nucleic acid, or other molecule), cells, tissues, viruses, and nanoparticles with different shapes.

CC3. The method of any prior CC embodiment, wherein the analyte comprises white blood cell, red blood cell and platelets.

CC4. The method of any prior CC embodiment, wherein the method comprises: analyzing the results at the remote location to provide an analyzed result; and communicating the analyzed result from the remote location to the mobile communication device.

CC5. The method of any prior CC embodiment, wherein the analysis is done by a medical professional at a remote location.

CC6. The method of any prior CC embodiment, wherein the mobile communication device receives a prescription, diagnosis or a recommendation from a medical professional at a remote location.

CC7. The method of any prior CC embodiment, wherein the thickness of the at least a part of VC sample at the closed configuration is larger than the thickness of VC sample deposited on the collection plate at an open configuration.

CC8. The method of any prior CC embodiment, wherein the thickness of the at least a part of VC sample at the closed configuration is less than the thickness of VC sample deposited on the collection plate at an open configuration.

CC9. The method of any prior CC paragraph, wherein the assaying step comprises detecting an analyte in the sample.

CC10. The method of any prior CC paragraph, wherein the analyte is a biomarker.

CC11. The method of any prior CC embodiment, wherein the analyte is a protein, nucleic acid, cell, or metabolite.

CC12. The method of any prior CC embodiment, wherein the assay done in step (b) is a binding assay or a biochemical assay.

DD1. A method for analyzing an analyte in a vapor condensate sample comprising: obtaining a device of any prior device claim;

depositing the vapor condensate sample onto one or both pates of the device; placing the plates in a closed configuration and applying an external force over at least part of the plates; and analyzing the analytes in the layer of uniform thickness while the plates are the closed configuration.

DD2. The method of any prior DD embodiment, wherein the method comprises:

(a) obtaining a sample;
(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
  i. a predetermined substantially uniform height,
  ii. a shape of pillar with substantially uniform cross-section and a flat top surface;
  iii. a ratio of the width to the height equal or larger than one;
  iv. a predetermined constant inter-spacer distance that is in the range of 10 $\mu$m to 200 $\mu$m;
  v. a filling factor of equal to 1% or larger;
(c) depositing the sample on one or both of the plates when the plates are configured in an open configuration, wherein the open configuration is a configuration in which the two plates are either partially or completely separated apart and the spacing between the plates is not regulated by the spacers;
(d), after (c), using the two plates to compress at least part of the sample into a layer of substantially uniform thickness that is confined by the sample contact surfaces of the plates, wherein the uniform thickness of the layer is regulated by the spacers and the plates, and has an average value equal to or less than 30 um with a variation of less than 10%, wherein the compressing comprises:

bringing the two plates together; and conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and (e) analyzing the in the layer of uniform thickness while the plates are the closed configuration;

wherein the filling factor is the ratio of the spacer contact area to the total plate area; wherein a conformable pressing is a method that makes the pressure applied over an area is substantially constant regardless the shape variation of the outer surfaces of the plates; and wherein the parallel pressing applies the pressures on the intended area at the same time, and a sequential pressing applies the pressure on a part of the intended area and gradually move to other area.

DD3. The method of any prior DD embodiment, wherein the method comprises:

removing the external force after the plates are in the closed configuration; and imaging the analytes in the layer of uniform thickness while the plates are the closed configuration; and counting a number of analytes or the labels in an area of the image.

DD4. The method of any prior DD embodiment, wherein the method comprises removing the external force after the plates are in the closed configuration; and measuring optical signal in the layer of uniform thickness while the plates are the closed configuration.

DD5. The method of any prior DD embodiment, wherein the inter-spacer distance is in the range of 20 □m to 200 □m.

DD6. The method of any prior DD embodiment, wherein the inter-spacer distance is in the range of 5 □m to 20 □m.

DD7. The method of any prior DD embodiment, wherein a product of the filling factor and the Young's modulus of the spacer is 2 MPa or larger.

DD8. The method of any prior DD embodiment, the surface variation is less than 50 nm.

DD9. The method of any prior DD embodiment, further comprising a step of calculating the concentration of an analyte in the relevant volume of sample, wherein the calculation is based on the relevant sample volume defined by the predetermined area of the storage site, the uniform sample thickness at the closed configuration, and the amount of target entity detected.

DD10. The method of any prior DD embodiment, wherein the analyzing step comprise counting the analyte in the sample.

DD11. The method of any prior DD embodiment, wherein the imaging and counting is done by:
i. illuminating the cells in the layer of uniform thickness;
ii. taking one or more images of the cells using a CCD or CMOS sensor;
iii. identifying cells in the image using a computer; and
iv. counting a number of cells in an area of the image.

DD12. The method of any prior DD embodiment, wherein the external force is provided by human hand.

DD13. The method of any prior DD embodiment, wherein it future comprises a dry reagent coated on one or both plates.

DD14. The method of any prior DD embodiment, wherein the layer of uniform thickness sample has a thickness uniformity of up to +/−5%.

DD15. The method of any prior DD embodiment, wherein the spacers are pillars with a cross-sectional shape selected from round, polygonal, circular, square, rectangular, oval, elliptical, or any combination of the same.

DD16. The method of any prior DD embodiment, wherein the spacing between the spacers is approximately the minimum dimension of an analyte.

EE1. The method of any prior CC or DD embodiment, wherein one or both plate sample contact surfaces comprises one or a plurality of amplification sites that are each capable of amplifying a signal from the analyte or a label of the analyte when the analyte or label is within 500 nm from an amplification site.

EE2. The method of any prior CC or DD embodiment, wherein the sample is exhale breath condensate.

EE3. The method of any prior CC or DD embodiment, wherein the sample is a vapor from a biological sample, an environmental sample, a chemical sample, or clinical sample.

EE4. The method of any prior CC or DD embodiment, wherein the analyte comprises a molecule (e.g., a protein, peptides, DNA, RNA, nucleic acid, or other molecules), cells, tissues, viruses, and nanoparticles with different shapes.

EE5. The method of any prior CC or DD embodiment, wherein the analyte comprises volatile organic compounds (VOCs).

EE6. The method of any prior CC or DD embodiment, wherein the analyte comprises nitrogen, oxygen, $CO_2$, $H_2O$, and inert gases.

EE7. The method of any prior CC or DD embodiment, wherein the analyte is stained.

EE8. The method of any prior CC or DD embodiment, wherein on one of the sample surface, it further comprises an enclosure-spacer that encloses a partial or entire VC samples deposited on the collection plate.

EE9. The method of any prior CC or DD embodiment, wherein the highly uniform thickness has a value equal to or less than 0.5 um.

EE10. The method of any prior CC or DD embodiment, wherein the highly uniform thickness has a value in the range of 0.5 um to 1 um.

EE11. The method of any prior CC or DD embodiment, wherein the highly uniform thickness has a value in the range of 1 um to 2 um.

EE12. The method of any prior CC or DD embodiment, wherein the highly uniform thickness has a value in the range of 2 um to 10 um.

EE13. The method of any prior CC or DD embodiment, wherein the highly uniform thickness has a value in the range of 10 um to 20 um.

EE14. The method of any prior CC or DD embodiment, wherein the highly uniform thickness has a value in the range of 20 um to 30 um.

Biomarks and Applications

Further aspects of the present disclosure include a CROF device that includes a plurality of capture agents that each binds to a plurality of analytes in a sample, i.e., a multiplexed CROF device. In such instances, the CROF device containing a plurality of capture agents can be configured to detect different types of analytes (protein, nucleic acids, antibodies, etc.). The different analytes can be distinguishable from each other on the array based on the location within the array, the emission wavelength of the detectable label that binds to the different analytes, or a combination of the above.

Other pathogens that can be detected in a diagnostic sample using the devices, systems and methods in the present invention include, but are not limited to: *Varicella zoster Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus wameri, Klebsiella pneumoniae, Haemophilus influenzae, Staphylococcus simulans, Streptococcus pneumoniae* and *Candida albicans*; gonorrhea (*Neisseria gorrhoeae*), syphilis (*Treponena pallidum*), clamydia (*Clamyda tracomitis*), nongonococcal urethritis (*Ureaplasm urealyticum*), chancroid (*Haemophilus ducreyi*), trichomoniasis (*Trichomonas vaginalis*); *Pseudomonas aeruginosa*, methicillin-resistant *Staphlocccccus aureus* (MSRA), *Klebsiella pneumoniae, Haemophilis influenzae, Staphlococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*, etc., as well as those listed in Tables B2 and 6.

TABLE B1

Diagnostic Markers

| Marker | disease |
|---|---|
| Aβ42, amyloid beta-protein (CSF) | Alzheimer's disease. |
| fetuin-A (CSF) | multiple sclerosis. |
| tau (CSF) | niemann-pick type C. |
| secretogranin II (CSF) | bipolar disorder. |
| prion protein (CSF) | Alzheimer disease, prion disease |
| Cytokines (CSF) | HIV-associated neurocognitive disorders |
| Alpha-synuclein (CSF) | parkinsonian disorders (neuordegenerative disorders) |
| tau protein (CSF) | parkinsonian disorders |
| neurofilament light chain (CSF) | axonal degeneration |
| parkin (CSF) | neuordegenerative disorders |
| PTEN induced putative kinase 1 (CSF) | neuordegenerative disorders |
| DJ-1 (CSF) | neuordegenerative disorders |
| leucine-rich repeat kinase 2 (CSF) | neuordegenerative disorders |
| mutated ATP13A2 (CSF) | Kufor-Rakeb disease |
| Apo H (CSF) | parkinson disease (PD) |
| ceruloplasmin (CSF) | PD |
| Peroxisome proliferator-activated receptor gamma coactivator-1 alpha (PGC-1α)(CSF) | PD |
| transthyretin (CSF) | CSF rhinorrhea (nasal surgery samples) |
| Vitamin D-binding Protein (CSF) | Multiple Sclerosis Progression |
| proapoptotic kinase R (PKR) and its phosphorylated PKR (pPKR) (CSF) | AD |
| CXCL13 (CSF) | multiple sclerosis |
| IL-12p40, CXCL13 and IL-8 (CSF) | intrathecal inflammation |
| Dkk-3 (semen) | prostate cancer |
| p14 endocan fragment (blood) | Sepsis: Endocan, specifically secreted by activated-pulmonary vascular endothelial cells, is thought to play a key role in the control of the lung inflammatory reaction. |
| Serum (blood) | neuromyelitis optica |
| ACE2 (blood) | cardiovascular disease |
| autoantibody to CD25 (blood) | early diagnosis of esophageal squamous cell carcinoma |
| hTERT (blood) | lung cancer |
| CAI25 (MUC 16) (blood) | lung cancer |
| VEGF (blood) | lung cancer |
| sIL-2 (blood) | lung cancer |
| Osteopontin (blood) | lung cancer |
| Human epididymis protein 4 (HE4) (blood) | ovarian cancer |
| Alpha-Fetal Protein (blood) | pregnancy |
| Albumin (urine) | diabetics |
| albumin (urine) uria | albuminuria |
| microalbuminuria | kidney leaks |
| AFP (urine) | mirror fetal AFP levels |
| neutrophil gelatinase-associated lipocalin (NGAL) (urine) | Acute kidney injury |
| interleukin 18 (IL-18) (urine) | Acute kidney injury |
| Kidney Injury Molecule -1 (KIM-1) (urine) | Acute kidney injury |
| Liver Fatty Acid Binding Protein (L-FABP) (urine) | Acute kidney injury |
| LMP1 (saliva) | Epstein-Barr virus oncoprotein (nasopharyngeal carcinomas) |

TABLE B1-continued

Diagnostic Markers

| Marker | disease |
| --- | --- |
| BARF1 (saliva) | Epstein-Barr virus oncoprotein (nasopharyngeal carcinomas) |
| IL-8 (saliva) | oral cancer biomarker |
| carcinoembryonic antigen (CEA) (saliva) | oral or salivary malignant tumors |
| BRAF, CCNI, EGRF, FGF19, FRS2, GREB1, and LZTS1 (saliva) | Lung cancer |
| alpha-amylase (saliva) | cardiovascular disease |
| carcinoembryonic antigen (saliva) | Malignant tumors of the oral cavity |
| CA 125 (saliva) | Ovarian cancer |
| IL8 (saliva) | spinalcellular carcinoma. |
| thioredoxin (saliva) | spinalcellular carcinoma. |
| beta-2 microglobulin levels - monitor activity of the virus (saliva) | HIV |
| tumor necrosis factor-alpha receptors - monitor activity of the virus (saliva) | HIV |
| CA15-3 (saliva) | breast cancer |

TABLE B2

Diagnostic Markers

HPA axis activity (Cushing's disease, Adrenal cortex diseases, etc.): Cortisol

Pregnancy/fetal development: Progesterone, human chorionic gonadotropin, Levonorgestrel, alpha-fetoprotein, early conception factor, Unconjugated Estriol, Estradiol, interleukin-6, Inhibin-A Infant development: NGAL, KIM-1, Cys-C, and B2mG, AFP, S100B, MBP
Menopause: Follicle stimulating hormone (FSH), Estrogen and progesterone, testosterone, free testosterone, and dehydroepiandrosterone sulfate (DHEAS), cortisol and dehydroepiandrosterone (DHEA)

Polycystic ovary syndrome: testosterone

Andropause: testosterone; testosterone precursors such as pregnenolone, progesterone, 17-hydroxypregnenolone, 17-hydroxyprogesterone, dehydroepiandrosterone (DHEA) and delta-4-androstene-3,17-dione; testosterone and dihydrotestosterone metabolites such as the 17-ketosteroids androsterone and etiocholanolone, polar metabolites in the form of diols, triols, and conjugates, as well as estradiol, estrogens, androsteindione, cortisol, FSH (follicle stimulating hormone), LH (luteinizing hormone), and GnRH (gonadotropin-releasing hormone)

Coagulation status/disorders: b-Thromboglobulin, Platelet factor 4, Von Willebrand factor, Factor I: Fibrinogen, Factor II: Prothrombin, Factor III: Tissue factor, Factor IV: Calcium, Factor V: Proaccelerin, Factor VI, Factor VII: Proconvertin, Factor VIII:, Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1)

Autism: miR-484, miR-21, miR-212, miR-23a, miR-598, miR-95, miR-129, miR-431, miR-7, miR-15a, miR-27a, miR-15b, miR-148b, miR-132, or miR-128; miR-93, miR-106a, miR-539, miR-652, miR-550, miR-432, miR-193b, miR-146b, miR-181d, miR-140, miR-146b, miR-381, miR-320a, or miR-106b; GM1, GD1a, GD1b, or GT1b; Ceruloplasmin, Metalothioneine, Zinc, Copper, B6, B12, Glutathione, Alkaline phosphatase, and Activation of apo-alkaline phosphatases Alzheimer's Disease: miR-107, miR-29a, miR-29b-1, or miR-9; miR-128; HIF-1α, BACE1, Reelin, CHRNA7, or 3Rtau/4Rtau, Reelin, Cystatin C, Truncated Cystatin C, C3a, t-Tau, Complement factor H, or alpha-2-macroglobulin; β-amyloid(1-42), β-amyloid(1-40), tau, phosphor-tau-181, acetylcholinesterase enzyme (AChE), GSK-3, PKC, VCAM-1 and ICAM-1, macrophage inflammatory proteins-1δ and -4 (MIP1δ and MIP4), regulated upon activation normal T-cell (RANTES), tumor necrosis factor-alpha (TNFα), midregional pro-atrial natriuretic peptide (MR-proANP), AD-associated neuronal thread protein (AD7c-NTP)

Parkinson's Disease: miR-133b; Nurr1, BDNF, TrkB, gstm1, or 5100 beta; apo-H, Ceruloplasmin, BDNF, Beta2-microglobulin, apoAII, tau, ABeta1-42, DJ-1, cTnI, myoglobin, MMP-9, MMP-8, MMP-2, sICAM-1, myeloperoxidase [MPO], IL-4, and/or IL-5; B-type natiuretic peptide [BNP], IL-1α, IL-11, IL-10, TNF-α, IFN-γ, VEGF, insulin, GLP-1 (active), GLP-1 (total), TREM1, Leukotriene E4, Akt1, Aβ-40, Aβ-42, Fas ligand, PSA, G-CSF, MIP-1α, IL-22, IL-8, IL-15, IL-6, IL-7, GM-CSF, IL-2, IL-12, IL-17α, IL-1β, MCP, IL-32 or RANTES, apolipoproteins A1, D and E, ischemia-modified albumin (IMA), fibronectin, s. alpha-amylase, aspartate aminotransferase, lactate dehydrogenase, tissue factor activity, MCP-1, sVCAM-1, sCD-40, insulin-like growth factor I (IGF-I), IGF-II TABLE B2-continued Diagnostic Markers Schizophrenia: miR-181b; miR-7, miR-24, miR-26b, miR-29b, miR-30b, miR-30e, miR-92, or miR-195; IFITM3, SERPINA3, GLS, or ALDH7A1BASP1; TP5B, ATP5H, ATP6V1B, DNM1, NDUFV2, NSF, PDHB Bipolar disease: FGF2, ALDH7A1, AGXT2L1, AQP4, or PCNT2

Mood disorder: Mbp, Edg2, Fgfr1, Fzd3, Mag, Pmp22, Ugt8, Erbb3, Igfbp4, Igfbp6, Pde6d, Ptprm, Nefh, Atp2c1, Atxn1, Btg1, C6orf182, Dicer1, Dnajc6, and Ednrb Major Depressive Disorder: FGFR1, FGFR2, FGFR3, or AQP4, Secretogranin, VGF, Cortisol, EGF, GCS, PPY, ACTH, AVP, CRH, MAT, A2M, ApoC3, CD40L, IL-6, IL-13, IL-18, IL-1ra, MPO, PAI-1, TNFA, ACRP30, ASP, FABP, INS, LEP, PRL, RETN, Testosterone, TSH, BDNF, S100B, NTF3, GDNF, ARTN Prion disease: Amyloid B4, App, IL-1R1, or SOD1; PrP(c), 14-3-3, NSE, S-100, Tau, AQP-4

Inflammation: TNF-α, IL-6, IL1β, Rheumatoid factor (RF), Antinuclear Antibody (ANA), acute phase markers including C-reactive protein (CRP), Clara Cell Protein (Uteroglobin); 14-3-3 protein epsilon; Isoform Long of Protocadherin alpha C2 precursor; Insulin-like growth factor IA precursor; Isoform 1 of Protocadherin-8 precursor; Isoform 1 of Sodium/potassium/calcium exchanger 2 precursor; Complement factor H-related 5; Di-N-acetylchitobiase precursor; Isoform 1 of Protein NDRG2; N-acetylglucosamine-6-sulfatase precursor; Isoform 1 of Semaphorin-3B precursor; Cadherin-5 precursor; UPF0454 protein Cl2orf49 precursor; Dihydrolipoyl dehydrogenase, mitochondria! precursor; Metallothionein-3; Fas apoptotic inhibitory molecule 2; Coactosin-like protein; Isoform Long of Platelet-derived growth factor A chain Precursor; Isoform Long of Endothelin-3 precursor; HLA class I histocompatibility antigen, A-1 alpha chain Precursor; Neuronal pentraxin-2 precursor; retbindin isoform 2; Neuroendocrine convertase 2 precursor; 15 kDa selenoprotein isoform 1 precursor; Phospholipase D4; Isoform 1 of CD109 antigen precursor; Ectonucleotide pyrophosphatase/phosphodiesterase family; member 6 precursor; Fascin; Golgi phosphoprotein 2; Isoform Delta 6 of Calcium/calmodulin-dependent protein kinase type II delta chain; Isoform 1 of FRAS1-related extracellular matrix protein 2 Precursor; Putative uncharacterized protein LOC130576; Isoform 1 of L-lactate dehydrogenase A chain; Isoform 1 of Polypeptide N-acetylgalactosaminyltransferase 13; Papilin; Protein DJ-1; Beta-mannosidase precursor; Protein YIPF3; Isoform 1 of Receptor-type tyrosine-protein phosphatase N2 Precursor; Cell growth regulator with EF hand domain protein 1; Sulfhydryl oxidase 2 precursor; Ig lambda chain V-II region TRO; Ig lambda chain V-VI region AR; Ig heavy chain V-III region WEA; Ig heavy chain V-III region CAM; Ig heavy chain V-III region BUR; Myosin-reactive immunoglobulin kappa chain variable region (Fragment); Microfibrillar protein 2 (Fragment); Ig kappa chain V-III region IARC/BL41 precursor; Ig kappa chain V-I region Kue; Ig kappa chain V-I region Scw; Ig kappa chain V-III region B6; IGLV6-57 protein; hypothetical protein LOC402665; Isoform 1 of Proline-rich acidic protein 1 precursor; Rheumatoid factor RF-ET13; Rheumatoid factor D5 heavy chain (Fragment); Uncharacterized protein ENSP00000375027; Uncharacterized protein ENSP00000375043; Uncharacterized protein ENSP00000375019; Isoform 1 of Protocadherin-1 precursor; Isoform 1 of Epithelial discoidin domain-containing receptor 1 precursor; Serine protease HTRA1 precursor; Isoform Delta of Poliovirus receptor-related protein 1 Precursor; chemokine (C-X-C motif) ligand 16; Plastin-2; 14-3-3 protein zeta/delta; Apolipoprotein C-II precursor; Brain-specific angiogenesis inhibitor 1 precursor; Semaphorin-3G precursor; Follistatin-related protein 3 precursor; Hepatocyte growth factor activator precursor; Isoform 1 of Contactin-associated protein-like 2 precursor; Phosphoglycerate kinase 1; Gamma-enolase; Phosphoglycerate mutase 2; Low affinity immunoglobulin gamma Fc region receptor III-A precursor; Isoform Beta of Poliovirus receptor precursor; Serine protease inhibitor Kazal-type 6 precursor; Isoform 1 of Chordin precursor; Out at first protein homolog precursor; Isoform 1 of Carboxypeptidase B2 precursor; ROBO2 isoform a Ig kappa chain V-III region POM; Isoform 1 of Protein-L-isoaspartate(D-aspartate) O-Methyltransferase CDNA FLJ45296 fis, clone BRHIP3003340, moderately similar to Actin, alpha skeletal muscle 2; Isoform 1 of RGM domain family member B precursor; Carboxypeptidase N subunit 2 precursor; Hypothetical LOC284297; L-6, IL-17, PAR-3, IL-17, T1/ST2, JunD, 5-LO, LTA4H, MBP, PLP, or alpha-beta crystalline; antithrombin III; α-2 glycoprotein 1, zinc; transthyretin (prealbumin); NADH dehydrogenase (ubiquinone) 1 beta subcomplex, 2; neurotrimin; orosomucoid 1 precursor (α-1-acid glycoprotein-1); leucine-rich α-2-glycoprotein; leucine-rich repeat protein; α-1-antitrypsin Chronique fatigue syndrome: Cortisol; Ig alpha-1 chain C region; Polymeric immunoglobulin receptor; Protein S100-A7; Cystatin-C; Cystatin-B; 14-3-3 protein zeta/delta; Zinc-alpha-2-glycoprotein (ZAG)

Sjögren's syndrome: IgA, IgG, IgM autoantibodies; IgA, lactoferrin and beta2-microglobulin; lysozyme C, and cystatin C, amylase and carbonic anhydrase; Autoantibodies (SSA/Ro; LA/SS-B)

Systemic lupus erythematosus (SLE): Autoantibodies (CDC25B, APOBEC3G, ARAF, BCL2A1, CLK1, CREB1, CSNK1G1, CSNK2A1, CWC27, DLX4, DPPA2, EFHD2, EGR2, ERCC2, EWSR1, EZH2, FES, FOS, FTHL17, GEM, GNA15, GNG4, HMGB2, HNRNPUL1, HOXB6, ID2, IF135, IGF2BP3, IGHG1, JUNB, KLF6, LGALS7, LIN28A, MLLT3, NFIL3, NRBF2, PABPC1, PATZ1, PCGF2, PPP2CB, PPP3CC, PRM1, PTK2, PTPN4, PYGB, RET, RPL18A, RPS7, RRAS, SCEL, SH2B1, SMAD2, STAM, TAF9, TIE1, UBA3, VAV1, WT1, TABLE B2-continued Diagnostic Markers ZAP70, ZNRD1, KIT, C6orf93, RPL34, DOM3Z, COPG2, DNCL12, RRP41, FBX09, RALBP1, PIA52, EEF1D, CONI, KATNB1, POLR2E, CCT3, KIAA0643, RPL37A, GTF2H2, MAP2K5, CDK3, RPS6KA1, MARK4, MTO1, MGC42105, NFE2L2, WDR45L, STK4, PFKFB3, NTRK3, MLF1, TRIM37, ACTL7B, RPL18A, CKS1B, TUBA1, NME6, SUCLA2, IGHG1, PRKCBP1, BAG3, TCEB3, RPL15, SSX4, MAP2K7, EEF1G, RNF38, PHLDA2, KCMF1, NUBP2, VPS45A, SSA/Ro, dsDNA, Smith, histones, thrombin)

CREST syndrome: Autoantibodies (centromere)

Systemic sclerosis: Autoantibodies (Type I topoisomerase)

Primary biliary cirrhosis: Autoantibodies (nucleoporin 62, Sp100 nuclear antigen, nucleoporin 210 kDa, mitochondria)

Cirrhosis: NLT; NLT, HBsAG, AST, YKL-40, Hyaluronic acid, TIMP-1, alpha 2 macroglobulin, a-1-antitrypsin P1Z allele, haptoglobin, or acid phosphatase ACP AC Autoimmune hepatitis: Autoantibodies (Liver kidney microsomal type 1, smooth muscle)

Celiac disease: Autoantibodies (tTG, actin)

Celiac disease Irritable Bowel Syndrome (IBS): Anti-IgA gliadin, REG1A, MMP3

Inflammatory bowel disease (IBD): Trypsinogen IV, SERT; Il-16, Il-1beta, Il-12, TNF-alpha, interferon gamma, 11-6, Rantes, MCP-1, Resistin, or 5-HT Ulcerative colitis: IFITM1, IFITM3, STAT1, STAT3, TAP1, PSME2, PSMB8, HNF4G, KLF5, AQP8, APT2B1, SLC16A, MFAP4, CCNG2, SLC44A4, DDAH1, TOB1, 231152_at, MKNK1, CEACAM7*, 1562836_at, CDC42SE2, PSD3, 231169_at, IGL@*, GSN, GPM6B, CDV3*, PDPK1, ANP32E, ADAM9, CDH1, NLRP2, 215777_at, OSBPL1, VNN1, RABGAP1L, PHACTR2, ASH1L, 213710_s_at, CDH1, NLRP2, 215777_at, OSBPL1, VNN1, RABGAP1L, PHACTR2, ASH1, 213710_s_at, ZNF3, FUT2, IGHA1, EDEM1, GPR171, 229713_at, LOC643187, FLVCR1, SNAP23*, ETNK1, LOC728411, POSTN, MUC12, HOXA5, SIGLEC1, LARP5, PIGR, SPTBN1, UFM1, C6orf62, WDR90, ALDH1A3, F2RL1, IGHV1-69, DUOX2, RAB5A, or CP; (P)ASCA Hyperplastic Polyp: SLC6A14, ARHGEF10, ALS2, IL1RN, SPRy4, PTGER3, TRIM29, SERPINB5, 1560327_at, ZAK, BAG4, TRIB3, TTL, FOXQ1

Psoriasis: miR-146b, miR-20a, miR-146a, miR-31, miR-200a, miR-17-5p, miR-30e-5p, miR-141, miR-203, miR-142-3p, miR-21, or miR-106a; miR-125b, miR-99b, miR-122a, miR-197, miR-100, miR-381, miR-518b, miR-524, let-7e, miR-30c, miR-365, miR-133b, miR-10a, miR-133a, miR-22, miR-326, or miR-215; IL-20, VEGFR-1, VEGFR-2, VEGFR-3, or EGR1;

Dermatitis herpetiformis: Autoantibodies (eTG)

Miller-Fisher Syndrome: Autoantibodies (ganglioside GQ1B)

Wegener's granulomatosis: Autoantibodies (c-ANCA)

Neuropathies: Autoantibodies (ganglioside GD3, ganglioside GM1)

Microscopic polyangiitis: Autoantibodies (p-ANCA)

Polymyositis: Autoantibodies (Signal recognition particles)

Scleromyositis: Autoantibodies (exosome complex Signal recognition particles)

Myasthenia gravis: Autoantibodies (nicotinic acetylcholine receptor Signal recognition particles, muscle-specific kinase (MUSK) Signal recognition particles)

Lambert-Eaton myasthenic syndrome: Autoantibodies (voltage-gated calcium channel (P/Q-type))

Hashimoto's thyroiditis: Autoantibodies (thyroid peroxidase)

Graves' disease: Autoantibodies (TSH receptor)

Paraneoplastic cerebellar syndrome: Autoantibodies (Hu, Yo (cerebellar Purkinje Cells), amphiphysin)

Encephalitis: Autoantibodies (voltage-gated potassium channel (VGKC), N-methyl-D-aspartate receptor (NMDA))

Sydenham's chorea: Autoantibodies (basal ganglia neurons)

Neuromyelitis: Autoantibodies (aquaporin-4)

TABLE B2-continued

Diagnostic Markers

Allergies: Allergen-specific IgAs

Rheumatic disease: miR-146a, miR-155, miR-132, miR-16, or miR-181; HOXD10, HOXD11, HOXD13, CCL8, LIM homeobox2, or CENP-E; TNFα

Rheumatoid arthritis: Autoantibodies (Rheumatoid factor, cyclic citrullinated protein), ATP-binding cassette, sub-family A, member 12 isoform b; ATP-binding cassette A12; apolipoprotein; B-100 precursor - human; complement component 3 precursor; alpha-2-glycoprotein 1, zinc; Alpha-2-glycoprotein, zinc; serine (or cysteine) proteinase inhibitor, clade A (alpha-1 antiproteinase, antitrypsin), member 2; Protease inhibitor 1-like; protease inhibitor 1 (alpha-1-antitrypsin)-like; group-specific component (vitamin D binding protein); hDBP; serine (or cysteine) proteinase inhibitor, clade A (alpha-1 antiproteinase, antitrypsin), member 1; Protease inhibitor (alpha-1-antitrypsin); protease inhibitor 1 (anti-elastase), alpha-1-antitrypsin; Vitronectin precursor V65 subunit; A kinase anchor protein 9 isoform 2; retrovirus-related hypothetical protein II - human retrotransposon LINE-1; nuclear receptor coactivator RAP250; peroxisome proliferator-act; nuclear receptor coactivator RAP2; Ig kappa chain NIG26 precursor - human; Vitamin D-binding protein precursor (DBF) (Group-specific component) (GC-globulin) (VDB) complement C4A precursor [validated] Human; guanine nucleotide binding protein (G protein), gamma transducing activity polypeptide 1; nucleoporin 98 kD isoform 4; nucleoporin 98 kD; Nup98-Nup96 precursor; GLFG-repeat containing; nucleoporin; vitronectin precursor; serum spreading factor; somatomedin B; complement S-protein; Alpha-1-antitrypsin precursor; HMG-BOX transcription; factor BBX; x 001; protein; hect domain and RLD 2; calcium channel, voltage-dependent, L type, alpha 1C subunit; Alpha-2-antiplasmin precursor (Alpha-2-plasmin inhibitor) (Alpha-2-PI) (Alpha-2-AP); Neuronal PAS domain protein 2 (Neuronal PAS2) (Member of PAS protein 4) (MOP4); Retinoic acid receptor gamma-2 (RAR-gamma-2) alpha-1-B-glycoprotein - human; Heparin cofactor II precursor (HC-II) (Protease inhibitor leuserpin 2) (HLS2); Ig gamma-1 chain C region; isocitrate dehydrogenase 3 (NAD+) alpha precursor; H-IDH alpha; isocitric dehydrogenase; isocitrate dehydrogenase [NAD] sub- unit alpha, mitochondrial; NAD+-specific ICDH; NAD(H)-specific isocitrate dehydrogenase alpha subunit precursor; isocitrate dehydrogenase (NAD+) alpha chain precursor; ferroxidase (EC 1.16.3.1) precursor [validated]-human; similar to zona pellucida binding protein; N-acetylneuraminic acid phosphate synthase; sialic acid synthase; sialic acid phosphate synthase; triple functional domain (PTPRF interacting); deleted in bladder cancer chromosome region candidate 1; ceruloplasmin (ferroxidase); Ceruloplasmin; RAB3A interacting protein (rabin3)-like 1; talin 2; similar to Ceruloplasmin precursor (Ferroxidase); orosomucoid 1 precursor; Orosomucoid-1 (alpha-1-acid glycoprotein-1); Ig lambda chain precursor - human; cold autoinflammatory syndrome 1; chromosome 1 open reading frame 7; angio-tensin/vasopressin receptor; similar to KIAA0913 protein; sodium channel, voltage-gated, type V, alpha polypeptide; hypothetical protein FLJ10379; orosomucoid 2; alpha-1-acid glycoprotein, type 2; Ig alpha-1 chain C region; corticosteroid binding globulin precursor; corticosteroid binding globulin; alpha-1 anti-proteinase, antitrypsin; KV3M_HUMAN IG KAPPA CHAIN V-III REGION HIC PRECURSOR; MUC_HUMAN Ig mu chain C region; similar to Ig gamma-2 chain C region; alpha-1-antichymotrypsin, precursor; alpha-1-antichymotrypsin; Antichymotrypsin; thyroid hormone receptor-associated protein, 240 kDa subunit; Ig heavy chain - human; Alpha-1-antichymotrypsin precursor (ACT) hypothetical protein XP_173158; hypothetical protein DKFZp434G2226; haptoglobin; Plasma protease C1 inhibitor precursor (C1 Inh) (C1Inh) Haptoglobin-1 precursor; leucine-rich alpha-2-glycoprotein; S-arrestin; S-antigen; NAD(P)H dehydrogenase, quinone 2; NAD(P)H menadione oxidoreductase-1, di-oxin-inducible-2; NAD(P)H menadione oxi-doreductase 2, dioxin-inducible; angiotensin precursor [validated]-human; similar to KIAA1902 protein; similar to KIAA1728 protein; calpain 3 isoform d; calpain, large polypep- tide L3; calpain p94, large [catalytic] subunit; muscle-specific calcium-activated neutral protease 3 large subunit; asp (abnormal spindle)-like, microcephaly associated; haptoglobin-related protein; Haptoglobin-related locus; Ig alpha-2 chain C region; hypothetical protein DKFZp434P1818.1 - human (fragment); GC3_HUMAN Ig gamma-3 chain C region (Heavy chain disease protein) (HDC)

Organ Rejection: miR-658, miR-125a, miR-320, miR-381, miR-628, miR-602, miR-629, or miR-125a; miR-324-3p, miR-611, miR-654, miR-330_MM1, miR-524, miR-17-3p_MM1, miR-483, miR-663, miR-5,6-5p, miR-326, miR-197_MM2, or miR-346; matix metaloprotein-9, proteinase 3, or HNP Bone turnover/Osteoporosis: Pyridinoline, deoxypyridinoline, collagen type 1 corss-linked N-telopeptide (NTX), collagen type 1 corss-linked C-telopeptide (CTX), bone sialoprotein (BSP), Tartrate-resistant acid phosphatase 5b, deoxypyridinium (D-PYR) and osteocalcin (OC), hepatocyte growth factor and interleukin-1 beta, Osteocalcin, alkaline phosphatase, bone-specific alkaline phosphatase, serum type 1 procollagen (C1NP, P1NP)

Jaw osteonecrosis: PTH, insulin, TNF-α, leptin, OPN, OC, OPG and IL6

Gaucher's disease: lyso-GbI, Chitotriosidase and CCL18

Traumatic brain injury: apoA-1, S-100B, isoprostane, GFAP, NGAL, neuron-specific enolase (NSE)

TABLE B2-continued

Diagnostic Markers

Septic shock: 15-Hydroxy-PG dehydrogenase (up), LAIR1 (up), NFKB1A (up), TLR2,
PGLYPR3, TLR4, MD2, TLR5, IFNAR2, IRAK2, IRAK3, IRAK4, PI3K, PI3KCB, MAP2K6,
MAPK14, NFKB1A, NFKB1, ILIR1, MAP2K1IP1, MKNK1, FAS, CASP4, GADD45B, SOCS3,
TNFSF10, TNFSF13B, OSM, HGF, IL18R1, IL-6, Protein-C, IL-1beta Cancer: FEN-1; CEA, NSE, CA 19-9, CA 125, PSA, proGRP, SCC, NNMT, anti-p53
autoantibodies, Separase and DPPFV/Separase, SERPINA3; ACTB; AFM; AGT; AMBP;
APOF; APOA2; APOC1; APOE; APOH; SERPINC1; C1QB; C3; C4BPA; C8G; C9;
SERPINA6; CD14; CP; CRP; CSK; F9; FGA; FGG; FLNA; FN1; GC; HRG; IF; IGFALS;
ITGA1; ITIH1; ITIH2; ITIH4; KLKB1; LPA; MLL; MRC1; MYL2; MYO6; ORM1; SERPINF1;
SERPINA1; SERPINA4; PROS1; QSCN6; RGS4; SAA4; SERPINA7; TF; TFRC; TTN; UBC;
ALMS1; ATRN; PDCD11; KIAA0433; SERPINA10; BCOR; C10orf18; YY1AP1; FLJ10006;
BDP1; SMARCAD1; MKL2; CHST8; MCPH1; MYO18B; MICAL-L1; PGLYRP2; KCTD7;
MGC27165; A1BG; A2M; ABLIM1; ACTA1; AHSG; ANK3; APCS; APOA1; APOA4; APOB;
APOC3; APOL1; AZGP1; B2M; BF; C1R; C1S; C2; C4B; C5; C6; C7; C8A; C8B;
CDK5RAP2/CDK5RA2; CHGB; CLU; COMP; CORO1A; CPN1; CUL1; DET1; DSC1; F13A1;
F2; F5; FGB; GOLGA1; GSN; HBA1; HBB; HP; HPX; HSPA5; HUNK; IGFBP5; IGHG1;
IGLV4-3; KIF5C; KNG1; KRT1; KRT10; KRT9; LBP; LGALS3BP; LRG1; LUM; MMP14;
MYH4; NEB; NUCB2; ORM2; PF4V1; PIGR; PLG; PON1; PPBP; RBP4; RIMS1; RNF6;
SAA1; SEMA3D; SERPIND1; SERPINF2; SERPING1; SF3B1; SPINK1; SPP1; SPTB;
SYNE1; TAF4B; TBC1D1; TLN1; TMSB4X; TRIP11; TTR; UROC1; VTN; VWF; ZFHX2;
ZYX; PSA (total prostate specific antigen), Creatinine, Prostatic acid phosphatase, PSA
complexes, Prostrate-specific gene-1, CA 12-5, Carcinoembryonic Antigen (CEA), Alpha feto
protein (AFP), hCG (Human chorionic gonadotropin), Inhibin, CAA Ovarian C1824, CA 27.29,
CA 15-3, CAA Breast C1924, Her-2, Pancreatic, CA 19-9, CAA pancreatic, Neuron-specific
enolase, Angiostatin DcR3 (Soluble decoy receptor 3), Endostatin, Ep-CAM (MK-1), Free
Immunoglobulin Light Chain Kappa, Free Immunoglobulin Light Chain Lambda, Herstatin,
Chromogranin A, Adrenomedullin, Integrin, Epidermal growth factor receptor, Epidermal
growth factor receptor-Tyrosine kinase, Pro-adrenomedullin N-terminal 20 peptide, Vascular
endothelial growth factor, Vascular endothelial growth factor receptor, Stem cell factor
receptor, c-kit/KDR, KDR, and Midkine; Zinc α2-glycoprotein (ZAG)

Adenoma: SI, DMBT1, CFI*, AQP1, APOD, TNFRSF17, CXCL10, CTSE, IGHA1, SLC9A3,
SLC7A1, BATF2, SOCS1, DOCK2, NOS2A, HK2, CXCL2, IL15RA, POU2AF1, CLEC3B,
ANI3BP, MGC13057, LCK*, C4BPA, HOXC6, GOLT1A, C2orf32, IL10RA, 240856_at,
SOC53, MEIS3P1, HIPK1, GLS, CPLX1, 236045_x_at, GALC, AMN, CCDC69, CCL28,
CPA3, TRIB2, HMGA2, PLCL2, NR3C1, EIF5A, LARP4, RP5-1022P6.2, PHLDB2, FKBP1B,
INDO, CLDN8, CNTN3, PBEF1, SLC16A9, CDC25B, TPSB2, PBEF1,1D4, GJB5, CHN2,
LIMCH1, or CXCL9; ABCA8, KIAA1199, GCG, MAMDC2, C2orf32, 229670_at, IGF1,
PCDH7, PRDX6, PCNA, COX2, or MUC6

Head and Neck cancer: IL-1, IL-6, IL-8, VEGF, MMP-9, TGF-β, TNF-α, MMP-7,
plasminogen activated (PA), uPA, IGF, or INF-2

Barrett's esophagus: miR-21, miR-143, miR-145, miR-194, or miR-215; S100A2, S100A4;
p53, MUC1, MUC2

Lung cancer: miR-21, miR-205, miR-221 (protective), let-7a (protective), miR-137 (risky),
miR-372 (risky), or miR-122a (risky); miR-17-92, miR-19a, miR-92, miR-155, miR-191, or
miR-210; EGFR, PTEN, RRM1, RRM2, ABCB1, ABCG2, LRP, VEGFR2, VEGFR3, class III
b-tubulin; KRAS, hENT1; RLF-MYCL1, TGF-ALK, or CD74-ROS1, CCNI, EGFR, FGF19,
FRS2, and GREB1 LZTS, BRAF, FRS2, ANXA1, Haptoglobin Hp2, Zinc Alpha2-Glycoprotein,
Calprotectin, *Porphyromonas catoniae* 16S rRNA, *Campylobacter showae* 16S rRNA,
*Streptococcocus salivaris* 16S rRNA, *Campylobacter rectus* 16S rRNA, *Veillonella parvula*
16S rRNA, *Kigella oralis* 16S rRNA, and *Granulicatella adiacens* 16S rRNA Pancreatic cancer: miR-221, miR-181a, miR-155, miR-210, miR-213, miR-181b, miR-222,
miR-181b-2, miR-21, miR-181b-1, miR-220, miR-21, miR-181d, miR-223, miR-100-1/2, miR-125a,
miR-143, miR-10a, miR-146, miR-99, miR-100, miR-199a-1, miR-10b, miR-199a-2, miR-221,
miR-181a, miR-155, miR-210, miR-213, miR-181b, miR-222, miR-181b-2, miR-21, miR-181b-
1, miR-181c, miR-220, miR-181d, miR-223, miR-100-1/2, miR-125a, miR-143, miR-10a, miR-
146, miR-99, miR-100, miR-199a-1, miR-10b, miR-199a-2, miR-107, miR-103, miR-103-2,
miR-125b-1, miR-205, miR-23a, miR-221, miR-424, miR-301, miR-100, miR-376a, miR-125b-
1, miR-21, miR-16-1, miR-181a, miR-181c, miR-92, miR-15, miR-155, let-7f-1, miR-212, miR-
107, miR-024-1/2, miR-18a, miR-31, miR-93, miR-224, or let-7d; miR-148a, miR-148b, miR-
375, miR-345, miR-142, miR-133a, miR-216, miR-217 or miR-139; KRAS, CTNNLB1, AKT,
NCOA3, or B-RAF; BRCA2, PALB2, or p16, MBD3L2, KRAS, STIM2, DMXL2, ACRV1, DMD
and CABLES1, TK2, GLTSCR2, CDKL3, TPT1 and DPM1

Breast cancer: miR-21, miR-155, miR-206, miR-122a, miR-210, miR-155, miR-206, miR-
210, or miR-21; let-7, miR-10b, miR-125a, miR-125b, miR-145, miR-143, miR-16, miR-10b,
miR-125a; hsp70, MART-1, TRP, HER2, hsp70, MART-1, TRP, HER2, ER, PR, Class III b-
tubulin, or VEGFA; GAS5; ETV6-NTRK3; CAH6 (Carbonic anhydrase VI), K2C4 (Cytokeratin
4), CYTA (Cystatin A), FABP4 (Epid. Fatty acid binding prot.), IGHGI (Ig gamma-1 chain C

TABLE B2-continued

Diagnostic Markers region), TRFL (Lactoferrin), BPIL1 (Bact. Perm.-increasing prot.-1), CYTC (Cystatin C), HPT (Haptoglobin), PROF1 (Profilin-1), ZA2G (Zinc-alpha-2-glycoprotein), ENOA (Alpha enolase), IGHA2 (Ig alpha-2 chain C region), IL-1 ra (Interleukin-1 receptor anatagonist protein precursor), S10A7 (S100 calcium-binding protein A7), and SPLC2 (Short palate, lung and nasel epith Carc. assoc. protein 2)

Ovarian cancer: c-erbB-2, cancer antigen 15-3, p53, HER2/neu (c-erbB-2), 47D10 antigen, PTCD2, SLC25A20, NFKB2, RASGRP2, PDE7A, MLL, PRKCE, GPATC3, PRIC285 and GSTA4, MIPEP, PLCB2, SLC25A19, DEF6, ZNF236, C18orf22, COX7A2, DDX11, TOP3A, C9orf6, UFC1, PFDN2, KLRD1, LOC643641, HSP90AB1, CLCN7, TNFAIP2, PRKCE, MRPL40, FBF1, ANKRD44, CCT5, USP40, UBXD4, LRCH1, MRPL4, SCCPDH, STX6, LOC284184, FLJ23235, GPATC3, CPSF4, CREM, HIST1H1D, HPS4, FN3KRP, ANKRD16, C8 orf16, ATF71P2, PRIC285, miR-200a, miR-141, miR-200c, miR-200b, miR-21, miR-200a, miR-200b, miR-200c, miR-203, miR-205, miR-214, miR-199", or miR-215; miR-199a, miR-140, miR-145, miR-100, miR-let-7 cluster, or miR-125b-1; ERCC1, ER, TOPO1, TOP2A, AR, PTEN, CD24 or EGFR; VEGFA, VEGFR2, CA 125

Prostate cancer: AGPAT1, B2M, BASP2, IER3,1L1B, miR-9, miR-21, miR-141, miR-370, miR-200b, miR-210, miR-155, or miR-196a; miR-202, miR-296, miR-320, miR-370, miR-373, miR-498, miR-503, miR-184, miR-198, miR-302c, miR-345, miR-491, miR-513, miR-32, miR-182, miR-31, miR-26a-1/2, miR-200c, miR-375, miR-196a-1/2, miR-370, miR-425, miR-425, miR-194-1/2, miR-181a-1/2, miR-34b, let-71, miR-188, miR-25, miR-106b, miR-449, miR-99b, miR-93, miR-92-1/2, miR-125a, or miR-141; let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-199, miR-221, miR-222, miR-497, let-7f, miR-19b, miR-22, miR-26b, miR-27a, miR-27b, miR-29a, miR-29b, miR-30_5p, miR-30c, miR-100, miR-141, miR-148a, miR-205, miR-520h, miR-494, miR-490, miR-133a-1, miR-1-2, miR-218-2, miR-220, miR-128a, miR-221, miR-499, miR-329, miR-340, miR-345, miR-410, miR-126, miR-205, miR-7-1/2, miR-145, miR-34a, miR-487, or let-7b; miR-15a, miR-16-1, miR-143 or miR-145; AR, PCA3; FASLG or TNFSF10; U50; ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5, KLK2-ETV4, kallikrein-2 (KLK2), C reactive protein (CRP), cysteine-rich secretory protein 3 (CRISP3) and chromogranin A (CHGA), comprises prostatic acid phosphatase (PAP), lactate dehydrogenase (LDH), alkaline phosphatase (ALP), PSA Esophageal Cancer: PCA3, GOLPH2, SPINK1, TMPRSS2:ERG, miR-192, miR-194, miR-21, miR-200c, miR-93, miR-342, miR-152, miR-93, miR-25, miR-424, or miR-151; miR-27b, miR-205, miR-203, miR-342, let-7c, miR-125b, miR-100, miR-152, miR-192, miR-194, miR-27b, miR-205, miR-203, miR-200c, miR-99a, miR-29c, miR-140, miR-103, miR-107

Gastric cancer: miR-106a, miR-21, miR-191, miR-223, miR-24-1, miR-24-2, miR-107, miR-92-2, miR-214, miR-25, or miR-221; let-7a; RRM2, or surviving; EphA4

Gastrointestinal Stromal Tumor (GIST): DOG-1, PKC-theta, KIT, GPR20, PRKCQ, KCNK3, KCNH2, SCG2, TNFRSF6B, or CD34; PDGFRA, c-kit Colorectal carcinoma: miR-24-1, miR-29b-2, miR-20a, miR-10a, miR-32, miR-203, miR-106a, miR-17-5p, miR-30c, miR-223, miR-126, miR-128b, miR-21, miR-24-2, miR-99b, miR-155, miR-213, miR-150, miR-107, miR-191, miR-221, miR-20a, miR-510, miR-92, miR-513, miR-19a, miR-21, miR-20, miR-183, miR-96, miR-135b, miR-31, miR-21, miR-92, miR-222, miR-181b, miR-210, miR-20a, miR-106a, miR-93, miR-335, miR-338, miR-133b, miR-346, miR-106b, miR-153a, miR-219, miR-34a, miR-99b, miR-185, miR-223, miR-211, miR-135a, miR-127, miR-203, miR-212, miR-95, or miR-17-5p; miR-143, miR-145, miR-143, miR-126, miR-34b, miR-34c, let-7, miR-9-3, miR-34a, miR-145, miR-455, miR-484, miR-101, miR-145, miR-133b, miR-129, miR-124a, miR-30-3p, miR-328, miR-106a, miR-17-5p, miR-342, miR-192, miR-1, miR-34b, miR-215, miR-192, miR-301, miR-324-5p, miR-30a-3p, miR-34c, miR-331, or miR-148b; EFNB1, ERCC1, HER2, VEGF, or EGFR; AFRs, Rabs, ADAM10, CD44, NG2, ephrin-B1, MIF, b-catenin, Junction, plakoglobin, galectin-4, RACK1, tetrspanin-8, FasL, TRAIL, A33, CEA, EGFR, dipeptidase 1, hsc-70, tetraspanins, ESCRT, TS, PTEN, or TOP01; GREM1, DDR2, GUCY1A3, TNS1, ADAMTS1, FBLN1, FLJ38028, RDX, FAM129A, ASPN, FRMD6, MCC, RBMS1, SNA12, MEIS1, DOCK10, PLEKHC1, FAM126A, TBC1D9, VWF, DCN, ROBO1, MSRB3, LATS2, MEF2C, IGFBP3, GNB4, RCN3, AKAP12, RFTN1, 226834_at, COL5A1, GNG2, NR3C1*, SPARCL1, MAB21L2, AXIN2, 236894_at, AEBP1, AP1S2, C10orf56, LPHN2, AKT3, FRMD6, COL15A1, CRYAB, COL14A1, LOC286167, QKI, WWTR1, GNG11, PAPPA, or ELDT1; 227458_at, INDO, CXCL9, CCCR2, CD38, RARRES3, CXCL10, FAM26F, TNIP3, NOS2A, CCRL1, TLR8, IL18BP, FCRL5, SAMD9L, ECGF1, TNFSF13B, GBPS, or GBP1; TMEM37*, IL33, CA4, CCDC58, CLIC6, VERSUSNL1, ESPN, APCDD1, C13orf18, CYP4X1, ATP2A3, LOC646627, MUPCDH, ANPEP, C1orf115, HSD3B2, GBA3, GABRB2, GYLTL1B, LYZ, SPC25, CDKN2B, FAM89A, MOGAT2, SEMA6D, 229376_at, TSPAN5, IL6R, or SLC26A2

Melanoma: miR-19a, miR-144, miR-200c, miR-211, miR-324-5p, miR-331, or miR-374; miR-9, miR-15a, miR-17-3p, miR-23b, miR-27a, miR-28, miR-29b, miR-30b, miR-31, miR-34b, miR-34c, miR-95, miR-96, miR-100, miR-104, miR-105, miR-106a, miR-107, miR-122a, miR-124a, miR-125b, miR-127, miR-128a, miR-128b, miR-129, miR-135a, miR-135b, miR-137, miR-138, miR-139, miR-140, miR-141, miR-149, miR-154, miR-154+190C3, miR-181a, miR-182, miR-183, miR-184, miR-185, miR-189, miR-190, miR-199, miR-199b, miR-200a, miR-200b, TABLE B2-continued Diagnostic Markers miR-204, miR-213, miR-215, miR-216, miR-219, miR-222, miR-224, miR-299, miR-302a, miR-302b, miR-302c, miR-302d, miR-323, miR-325, let-7a, let-7b, let-7d, let-7e, or let-7g; MUM-1, beta-catenin, or Nop/5/Sik; DUSP-1, Alix, hsp70, Gib2, Gia, moesin, GAPDH, malate dehydrogenase, p120 catenin, PGRL, syntaxin-binding protein 1 & 2, septin-2, or WD-repeat containing protein 1; H/ACA (U1071), SNORA11D Head and neck cancer: miR-21, let-7, miR-18, miR-29c, miR-142-3p, miR-155, miR-146b, miR-205, or miR-21; miR-494; HPV E6, HPV E7, p53, IL-8, SAT, H3FA3; EGFR, EphB4, or EphB2; CHCHD7-PLAG1, CTNNB1-PLAG1, FHIT-HMGA2, HMGA2-NFIB, LIFR-PLAG1, or TCEA1-PLAG1

Oral squamous cell carcinoma: p53 autoantibodies, defensing-1, lncRNAs (MEG-3, MALAT-1, HOTAIR, NEAT-1, UCA) Cortisol, lactate dehydrogenase, Transferrin, cyclin D1, Maspin, alpha-amylase, IL-8, TNF-α, IL-1, IL-6, Basic fibroblast growth factor, Statherin, Cyfra 21.1, TPA, CA125, Endothelin-1, IL-1β, CD44, IGF-1, MMP-2, MMP-9, CD59, Catalase, Profilin, S100A9/MRP14, M2BP, CEA, Carcinoma associated antigen CA-50, Salivary carbonyls, Maspin, 8-oxoguanine DNA glycosylase, OGG1, Phosphorylated-Src, Ki-67, Zinc finger protein 501 peptide, Hemopexin, Haptoglobin, Complement C3, Transthyretin, α1-antitrypsin, Peroxidase, GST, SOD, 8-OHdG, Glutathione, MDA, miR-125a, miR-200a, miR-31

Salivary gland tumors: Fibroblast growth factor 2 (FGF2) and fibroblast growth factor receptor 1 (FGFR1)

Hepatocellular carcinoma: miR-221; et-7a-1, let-7a-2, let-7a-3, let-7b, let-7c, let-7d, let-7e, let-7f-2, let-fg, miR-122a, miR-124a-2, miR-130a, miR-132, miR-136, miR-141, miR-142, miR-143, miR-145, miR-146, miR-150, miR-155(BIC), miR-181a-1, miR-181a-2, miR-181c, miR-195, miR-199a-1-5p, miR-199a-2-5p, miR-199b, miR-200b, miR-214, miR-223, or pre-miR-594; miR-122, miR-100, or miR-10a; miR-198 or miR-145

Renal cell carcinoma: miR-141, miR-200; miR-28, miR-185, miR-27, miR-let-7f-2; laminin receptor 1, betaig-h3, Galectin-1, a-2 Macroglobulin, Adipophilin, Angiopoietin 2, Caldesmon 1, ClassII MHC-associated invariant chain (CD74), Collagen IV-al, Complement component, Complement component 3, Cytochrome P450, subfamily IIJ polypeptide 2, Delta sleep-inducing peptide, Fc g receptor 111a (CD16), HLA-B, HLA-DRa, HLA-DRb, HLA-SB, IFN-induced transmembrane protein 3, IFN-induced transmembrane protein 1, or Lysyl Oxidase; IF1 alpha, VEGF, PDGFRA; ALPHA-TFEB, NONO-TFE3, PRCC-TFE3, SFPQ-TFE3, CLTC-TFE3, or MALAT1-TFEBf Renal cell carcinoma: Akt, total Erk1/2, total Met, total GSK3b, total Hif1a, total p21, total AMPKa1, total VEGF, total PIGF, total VEGFR-1/Flt-1, phosphorylated Akt, phosphorylated Erk1/2, phosphorylated. Met, phosphorylated STAT3, phosphorylated GSK3b, and phosphorylated AMPKa1

Cervical cancer: HPV E6, HPV E7, or p53

Thyroid cancer: AKAP-BRAF, CCDC6-RET, ERC1-RETM, GOLGA5-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET; PAX8-PPARγ

Neuroblastoma: Neuron-specific enolase (NSE)

Glioblastoma: GFAP

Brain cancer: miR-21, miR-10b, miR-130a, miR-221, miR-125b-1, miR-125b-2, miR-9-2, miR-21, miR-25, or miR-123; miR-128a, miR-181c, miR-181a, or miR-181b; GOPC-ROS1; MGMT; EGFR Blood Cancers: HOX11, TAL1, LY1, LMO1, or LMO2; TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, for acute lymphocytic leukemia (ALL); BCL11B-TLX3, IL2-TNFRFS17, NUP214-ABL1, NUP98-CCDC28A, TAL1-STIL, or ETV6-ABL2, for T-cell acute lymphocytic leukemia (T-ALL); ATIC-ALK, KIAA1618-ALK, MSN-ALK, MYH9-ALK, NPM1-ALK, TGF-ALK or TPM3-ALK, for anaplastic large cell lymphoma (ALCL); BCR-ABL1, BCR-JAK2, ETV6-EVI1, ETV6-MN1 or ETV6-TCBA1, for chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAP1, AML-AFF1, MLL-ARHGAP26, MLL-ARHGEF12, MLL-CASC5, MLL-CBL, MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYO1F, MLL-PICALM, MLL-SEPT2, MLL-SEPT6, MLL-SORBS2, MYST-SORBS2, MYST-CREBBP, NPM1-MLF1, NUP98-HOXA13, PRDM16-EVI1, RABEP1-PDGFRB, RUNX1-EVI1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-

TABLE B2-continued

Diagnostic Markers

ZNF-384, for AML; CCND1-FSTL3, for chronic lymphocytic leukemia (CLL); and FLIP1-
PDGFRA, FLT3-ETV6, KIAA1509-PDGFRA, PDE4DIP-PDGFRB, NIN-PDGFRB, TP53BP1-
PDGFRB, or TPM3-PDGFRB, for hyper eosinophilia/chronic eosinophilia; miR-23b, miR-24-1,
miR-146, miR-155, miR-195, miR-221, miR-331, miR-29a, miR-195, miR-34a, or miR-29c;
miR-15a, miR-16-1, miR-29 or miR-223; miR-128b, miR-204, miR-218, miR-331, miR-181b-1,
miR-17-92

B-Cell Chronic Lymphocytic Leukemia: miR-183-prec, miR-190, miR-24-1-prec, miR-33,
miR-19a, miR-140, miR-123, miR-10b, miR-15b-prec, miR-92-1, miR-188, miR-154, miR-217,
miR-101, miR-141-prec, miR-153-prec, miR-196-2, miR-134, miR-141, miR-132, miR-192, or
miR-181b-prec; miR-213, miR-220; ZAP70, AdipoR1; BCL3-MYC, MYC-BTG1, BCL7A-MYC,
BRWD3-ARHGAP20 or BTG1-MYC B-cell lymphoma: miR-17-92 polycistron, miR-155, miR-210, or miR-21, miR-19a, miR-92,
miR-142 miR-155, miR-221 miR-17-92, miR-21, miR-191, miR-205, U50; miR-17-92, miR-
155, miR-210, or miR-21; A-myb, LM02, JNK3, CD10, bcl-6, Cyclin D2, IRF4, Flip, or CD44;
CITTA-BCL6, CLTC-ALK, IL21R-BCL6, PIM1-BCL6, TFCR-BCL6, IKZF1-BCL6 or SEC31A-
ALK Burkitt's lymphoma: pri-miR-155; MYC, TERT, NS, NP, MAZ, RCF3, BYSL, IDE3, CDC7,
TCL1A, AUTS2, MYBL1, BMP7, ITPR3, CDC2, BACK2, TTK, MME, ALOX5, or TOP1; BCL6,
KI-67; IGH-MYC, LCP1-BCL6

Endometrial cancer: miR-185, miR-106a, miR-181a, miR-210, miR-423, miR-103, miR-107,
or let-7c; miR-71, miR-221, miR-193, miR-152, or miR-30c; NLRP7, AlphaV Beta6 integrin
Uterine leiomyomas: let-7 family member, miR-21, miR-23b, miR-29b, or miR-197
Myelofibrosis: miR-190; miR-31, miR-150 and miR-95; miR-34a, miR-342, miR-326, miR-
105, miR-149, miR-147

Pheochromocytoma: Catecholamines (epinephrine, norepinephrine, adrenaline)

Kidney disease/injury: ADBP-26, NHE3, KIM-1, glutamyltransferase, N-acetyl-beta-D-
glucosaminidase, lysozyme, NGAL, L-FABP, bikunin, urea, prostaglandins, creatinine, alpha-
1-microglobulin, retinol binding protein, glutathione-S-transferases, adiponectin, beta-2-
macroglobuin, calbindin-D, cysteine-rich angiogenic inducer 61, endothelial/epithial growth
factors, alpha-1-acid glycoprotein (orosomucoid), prealbumin, modified albumin, albumin,
transferrin, alpha-1-lipoprotein, alpha-1-antitrypsin matrix metalloproteinases (MMPs), alpha-
1-fetoprotein, Tamm Horsfall protein, homoarginine, interleukin 18, monocyte chemotactic
protein-1 (MCP-1), Lipocalin, VCAN, NRP1, CCL2, CCL19, COL3A1, GZMM, alpha-
galactosidase, casein kinase 2, IP-10, Mig, I-TAC, MIP-1α, MIP-3α, and MIP-1β, alpha-2-
glycoprotein-Zinc, leucine-rich alpha-2-glycoprotein, uromodulin, Pacsin 2, hepcidin-20,
hepcidin-25, AIF-2, urinary type-IV collagen, lipocalin-type prostaglandin D synthase (L-
PGDS), urinary neutrophil gelatinase-associated lipocalin (uNGAL), Annexin A1, Rab23, Shh,
Ihh, Dhh, PTCH1, PTCH2, SMO, Gli1, Gli2, Gli3, TLR4, cystatin C, AQPI, AQP2, AQP3,
NKCC2, NaPill, DAHKSEVAHRFKD; [RNA:] SLC12A1, UMOD, vWF, MMPI, MMP3,
SLC22A6, SLC22A 8, SLC22A 12, podocin, cubulin, LRP2, AQP9, and albumin,
carcinoembryonic antigen (CEA), mucin, alpha-fetoprotein, tyrosinase, melanoma associated
antigen, mutated tumor protein 53, p21, PUMA, prostate-specific antigen (PSA) or
thyroglobulin, von Willebrand factor (VWF), thrombin, factor VIII, plasmin, fibrin, osteopontin
(SPP1), Rab23, Shh, Ihh, Dhh, PTCH1, PTCH2, SMO, Gli1, Gli2, Gli3

Liver failure/disease: Lactoferrin, uric acid, cortisol, alpha-amylase, Carnitine; Cholic Acid;
Chenodeoxycholic, Deoxycholic, Lithocholic, Glycocholic; Prostaglandin E$_2$; 13,14-dihydro-15-
keto Prostaglandin A2; Prostaglandin B2; Prostaglandin F2a; 15-keto-Prostaglandin F2α; 6-
keto-Prostaglandin F1α; Thromboxane B2; 11-dehydro-Thromboxane B2; Prostaglandin D2;
Prostaglandin J2; 15-deoxy-Δ12,14-Prostaglandin J2; 11β-Prostaglandin F2α; 5(S)-
Hydroxyeicosatetraenoic acid; 5(S)-Hydroxyeicosapentaenoic acid; Leukotriene B4;
Leukotriene B5; Leukotriene C4; Leukotriene D4; Leukotriene E4; Leukotriene F4; 12(S)-
Hydroxyeicosatetraenoic acid; 12(S)-Hydroxyeicosapentaenoic acid; 15(S)-
Hydroxyeicosatetraenoic acid; 15(S)-Hydroxyeicosapentaenoic acid; Lipoxin A4; 8(S)-
Hydroxyeicosatetraenoic acid; 9-Hydroxyeicosatetraenoic acid; 11-Hydroxyeicosatetraenoic
acid; 8-iso-Prostaglandin F2α; 9-Hydroxyoctadecadienoic acid; 13-Hydroxyoctadecadienoic
acid; 20(S)-Hydroxyeicosatetraenoic acid; 9,10-Epoxyoctadecenoic acid; 12,13-
Epoxyoctadecenoic acid; 12,13-Dihydroxyoctadecenoic acid; 5,6-Epoxyeicosatrienoic acid;
11,12-Epoxyeicosatrienoic acid; 14,15-Epoxyeicosatrienoic acid; 5,6-Dihydroxyeicosatrienoic
acid; 8,9-Dihydroxyeicosatrienoic acid; 11,12-Dihydroxyeicosatrienoic acid; 14,15-
Dihydroxyeicosatrienoic acid; 14,15-Epoxyeicosatetraenoic acid; 17,18-
Epoxyeicosatetraenoic acid; 14,15-Dihydroxyeicosatetraenoic acid; 17,18-
Dihydroxyeicosatetraenoic acid; 19,20-Dihydroxydocosapentaenoic acid; diacetylspermine,
hemopexin, TLR4

Stroke: MMP9, S100-P, S100A12, SI00A9, coag factor V, Arginasel, CA-IV, monocarboxylic
acid transporter, ets-2, EIF2alpha, cytoskeleton associated protein 4, N-formylpeptide
receptor, Ribonuclease2, N-acetylneuraminate pyruvate lyase, BCL-6, or Glycogen
phosphorylase

TABLE B2-continued

Diagnostic Markers

Heart failure/Cardiovascular health: 8-iso-prostaglandin F2a (8-iso-PGF2a), miR-195, miR-208, miR-214, let-7b, let-7c, let-7e, miR-15b, miR-23a, miR-24, miR-27a, miR-27b, miR-93, miR-99b, miR-100, miR-103, miR-125b, miR-140, miR-145, miR-181a, miR-191, miR-195, miR-199a, miR-320, miR-342, miR-451, or miR-499; miR-1, miR-10a, miR-17-5p, miR-19a, miR-19b, miR-20a, miR-20b, miR-26b, miR-28, miR-30e-5p, miR-101, miR-106a, miR-126, miR-222, miR-374, miR-422b, or miR-423; MRP14, CD69; CK-MB, cTnI (cardiac troponin), CRP, BPN, IL-6, MCSF, CD40, CD40L, SFRP-3, NT-proBNP, troponin T, SKITHRIHWESASLL, AHKSEVAHRFK, uroguanylin, BNP, miR-378, miR-497, miR-21, miR-99a, miR 29a, miR-30b, miR-29c, miR-331.3p, miR-19a, miR-22, miR-502.3, and miR-652; IL-16, sFas, Fas ligand, MCP-3, HGF, CTACK, EOTAXIN, adiponectin, IL-18, TIM P.4, TIM P.1, CRP, VEGF, and EGF, C-reactive protein (CRP); myoglobin (MYO), creatinine kinase myocardial band (CK-MB), cardiac troponins (cTn), and myeloperoxidase; TNF-α, and MMP-9; CD40

Vulnerable plaque: Amylase, L-6, MMP-9, PAPP-A, D-dimer, fibrinogen, Lp-PLA2, SCD40L, II-18, oxLDL, GPx-1, MCP-1, P1GF, or CRP High blood pressure: lysozyme Fibromyalgia: NR2D Neuropathic Pain: CCR2/4, CNP; ICAM-1, CGRP, TIMP-1, CLR-1, HSP-27, FABP, or apolipoprotein D; OX42, ED9

Tiredness/fatigue: PPGKPQGPPPQGGNQPQGPPPPPGKPQ (SEQ ID NO: //); GNPQGPSPQGGNKPQGPPPPPGKPQ (SEQ ID NO: //); SPPGKPQGPPQQEGNKPQGPPPPPGKPQ (SEQ ID NO: //); GGHPPPP (SEQ ID NO: //), ESPSLIA (SEQ ID NO: //); endorepellin; human herpesvirus 6, human herpesvirus 7, human cytomegalovirus, and Epstein-Barr virus (EBV)

Stress: Cortisol, chromogranin A, alpha-amylase, secretary IgA, lysozyme, dehydro-androsteronesulfate; 17-ketosteroidsulfate; dehydro-epiandrostronesulfate; corticosteroid, 17-hydroxycorticosteroid, growth hormone, oxytocin, aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione 5-transferase p, GroEL, heat shock protein 25/27, heat shock protein 40, heat shock protein 60, heat shock protein 70, heat shock protein 90, heat shock transcription factor-1, heme oxygenase-1, interleukin 113, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide Malnutrition: sIgA Nutritional status: Prealbumin, Albumin, Retinol-binding protein (RBP), Transferrin, Acylation-Stimulating Protein (ASP), Adiponectin, Agouti-Related Protein (Ag RP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor)

Energy balance (protein excretion)/energy status/metabolic state: AMPK, pre-albumin, retinol binding protein, urea, cholesterol, lipoproteins, insulin, insulin C peptide, IGF binding proteins, e.g. IGF-BPI, liver enzymes Diabetes: 11-8, CTSS, ITGB2, HLA-DRA, CD53, PLAG27, or MMP9; RBP4; 8-iso-prostaglandin F2a (8-iso-PGF2a), 11-dehydro-thromboxane $B_2$ (TXM), C-peptide, Advanced glycosylation end products (AGEs), 1,5-anhydroglucitol, NGPTL3 and 4, autoantibodies (Zn transporter 8, glutamic acid decarboxylase (GAD)), ATP-binding cassette, sub-family C (CFTR/MRP), member 8; ATP-binding cassette, sub-family C (CFTR/MRP), member 9; angiotensin 1 converting enzyme (peptidyl-dipeptidase A) 1; adenylate cyclase activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product-specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes insipidus, neurohypophyseal); bombesin receptor subtype 3; betacellulin; benzodiazepine receptor (peripheral); complement TABLE B2-continued Diagnostic Markers component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine palmitoyltransferase I; carnitine palmitoyltransferase II; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; forkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; glucagon-like peptide 1 receptor; guanine nucleotide binding protein (G protein), beta polypeptide 3; glutamic-pyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like growth factor binding protein 1; insulin-like growth factor binding protein 3; inhibitor of kappa light polypeptide gene enhancer in B-cells, kinase beta; interleukin 10; interleukin 18 (interferon-gamma-inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor co-repressor 1; neurogenic differentiation 1; nuclear factor of kappa light polypeptide gene enhancer in B-cells 1 (p105); nerve growth factor, beta polypeptide; non-insulin-dependent Diabetes Mellitus (common, type 2) 1; non-insulin-dependent Diabetes Mellitus (common, type 2) 2; Noninsulin-dependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; nuclear respiratory factor 1; oxytocin, prepro-(neurophysin I); purinergic receptor P2Y, G-protein coupled, 10; purinergic receptor P2Y, G-protein coupled, 12; purinergic receptor P2Y, G-protein coupled, 2; progestagen-associated endometrial; protein (placental protein 14, pregnancy-associated endometrial alpha-2-globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; endothelial growth factor-related protein; phosphoinositide-3-kinase, catalytic, alpha polypeptide; phosphoinositide-3-kinase, regulatory subunit 1 (p85 alpha); phospholipase A2, group XIIA; phospholipase A2, group IID; plasminogen activator, tissue; patatin-like phospholipase domain containing 2; proopiomelanocortin (adrenocorticotropin/beta-lipotropin/alpha-melanocyte stimulating hormone/beta- melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B' (PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandin-endoperoxide synthase 2 (prostaglandin G/H synthase and cyclooxygenase); protein tyrosine phosphatase, mitochondrial 1; Peptide YY retinol binding protein 4, plasma (RBP4); regenerating islet-derived 1 alpha (pancreatic stone protein, pancreatic thread protein); resistin; ribosomal protein S6 kinase, 90 kDa, polypeptide 1; Ras-related associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid TABLE B2-continued Diagnostic Markers regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1 (ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMG-box); transforming growth factor, beta 1 (Camurati-Engelmann disease); transglutaminase 2 (C polypeptide, protein-glutamine-gamma-glutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondria!, proton carrier); upstream transcription factor 1; urotensin 2; vascular cell adhesion molecule 1; vascular endothelial growth factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin;
interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline Metabolic syndrome/prediabetes: GFAP autoantibodies Alcohol abuse/dependence: aminotransferases, gamma-glutamyltransferase, ethanol, ethyl glucuronide, sialic acid, β-hexosaminidase A, oral peroxidase, methanol, diethylene/ethylene glycol, α-amylase, clusterin, haptoglobin, heavy/light chains of immunoglobulins and transferrin; α-fucosidase (FUC), α-mannosidase (MAN), β-galactosidase (GAL), and β-glucuronidase (GLU)

Non-alcoholic fatty liver disease: cytokeratin CK-18 (M65 antigen), caspase-cleaved CK-18 (M30-antigen), resistin, adiponectin, visfatin, insulin, tumor necrosis factor-alpha (TNF-α), interleukin 6 (IL-6), or interleukin 8 (IL-8), aspartate aminotransferase (AST) and alanine aminotransferase (ALT); gamma-glutamyltransferase (GGT), immunoglobulin A, carbohydrate-deficient transferrin (CDT), glutamic oxaloacetic transaminase (GOT), glutamic pyruvic transaminase (GPT), bilirubin Cystic fibrosis: amylase, cathepsin-D, lactate dehydrogenase Ectodermal dysplasia: alpha-amylase Sarcoidosis: IL-6, TNF-α, IFN-α, IL-17, IP-10, MIG, HGF, VEGF, TNF-RII, G-CSF, IFN-γ, MCP-1, RANTES and IL-5

Asthma: eotaxin-1/CCL11, RANTES/CCL5, and IL-5; IL-113, IL-6, MCP-1/CCL2, and IL-8/CXC L8; IP-10/CXCL10

Periodontitis/dental caries: aspartate aminotransferase (AST) and alkaline phosphatase (ALP), uric acid and albumin; 12-HETE; MMP-8, TIMP-1, and ICTP Muscle damage: Myoglobin, creatine kinase (CK), lactate dehydrogenase (LDH), aldolase, troponin, carbonic anhydrase type 3 and fatty acid-binding protein (FABP), transaminases Infection (*Mycobacterium tuberculosis*): IL-32, NXNL1, PSMA7, C6orf61, EMP1, CLIC1, LACTB and DUSP3, LOC389541, MIDI IP 1, KLRC3, KLF9, FBXQ32, C50RF29, CHUK, LOC652062, C6ORF60, MTMR I I,sCD170; IFN-gamma; IL-Iβ, IL-6, IL-8, IL-10, IL-12p70, sCD4, SCD25, SCD26, sCD32b/c, SCD50, SCD56, SCD66a, SCD83, sCD85j, SCD95, SCD106, sCD120b, sCD121b, SCD127, SCD154, SCD222, SCD226, sCDw329 and TNF alpha; VEGF, AAT, CRP, IL-IRA, TIMP-1, IL- 18, A2Macro, Haptoglobin ICAM-1, VCAM- 1, SCF, IL-17, Fibrinogen, beta-2-macroglobulin, TNF-alpha, C3 and TNFR2, GPR117, TAZ, HSDL I, HIP 1 (host)

Infection (*Helicobacter pylori*): MUC-5B and MUC 7

Infection (*Candida* species): Hsp70, calprotectin, histatins, mucins, basic proline rich proteins and peroxidases (host);

Infection (influenza): Hemagglutinin (H1), neuraminidase (N1); C-reactive protein, [RNA:] DNA cross-link repair 1A, PSO2 homolog, synaptonemal complex protein 3, v-maf musculoaponeurotic fibrosarcoma oncogene family, chitinase 3-like 3, matrix TABLE B2-continued Diagnostic Markers metalloproteinase 12, ATP-binding cassette, sub-family E (OABP), member 1, ATP-binding
cassette, sub-family F (GCN20), member 1, feminization 1 homolog a (*C. elegans*), general
transcription factor II H. polypeptide 2, forkhead box P1, zinc finger protein 282, arginyl-tRNA
synthetase-like, Mitochondrial ribosomal protein L48, ribosomal protein S4, X-linked,
eukaryotic translation elongation factor 1 alpha 1, proteaseome (prosome, macropain) 28
subunit 3, GLE1 RNA export mediator-like (yeast), small nuclear ribonucleoprotein
polypeptide A', cleavage and polyadenylation specific factor 2, ribosomal protein L27a, ,
thioredoxin domain containing 4 (endoplasmic reticulum), flap structure specific endonuclease
1, ADP-ribosylation factor-like 6 interacting protein 2, cytidine 5'-triphosphate synthase 2,
glutathione S-transferase, mu 5, phospholipase D1, aspartate-beta-hydroxylase, leukotriene
A4 hydrolase, cytochrome P450 family 17, subfamily a, polypeptide 1, thioredoxin interacting
protein, carbonyl reductase 2, alpha globin regulatory element containing gene, male-specific
lethal-2 homolog (I Drosophila[L ), RAB1, member RAS oncogene family, protein tyrosine
phosphatase, non-receptor type 21, potassium voltage-gated channel, Isk-related subfamily,
gene 3, Bcl2-associated athanogene 3, lymphocyte cytosolic protein 2, pore forming protein-
like, tumor necrosis factor receptor superfamily, member 19, filamin beta, microtubule-actin
crosslinking factor 1, keratin complex 1, acidic, gene 18, keratin complex 1, acidic, gene 19,
mesoderm development candiate 2, tubulin, alpha 4, , glutathione peroxidase 1, integrin
linked kinase, guanine nucleotide binding protein, alpha inhibiting 2, cyclin L2, tubulin, alpha
2, DEAD (Asp-Glu-Ala-Asp) box polypeptide 5, programmed cell death 4, proteasome
(prosome, macropain) 26S subunit, non-ATPase 8, signal sequence receptor, beta, RAD23b
homolog (host)

Infection (HIV-1): p24, gp41, gp120

Infection (Hepatitis B virus): Core, Envelope, Surface (Ay)

Infection (Hepatitis C virus): Core, NS3, NS4, NS5

Infection (Hepatitis E virus): orf2 3 KD, orf2 6 KD, orf3 3 KD

Infection (*Vibrio cholerae*): Cholera Toxin

Infection (*Corynebacterium diphtheria*): Diphtheria toxin

Infection (Epstein-Barr virus): EA, VCA, NA

Infection (Herpes simplex virus HSV-1): gD

Infection (Herpes simplex virus HSV-2): gG

Infection (*Clostridium tetani*): Tetanus toxin

Infection (*Treponema pallidum*): 15 kd, p47

Infection (*Entamoeba histolytica*): M17

Infection (*Toxoplasma gondii*): a2-HS glycoprotein and apB glycoprotein (host); TGME49
052280, TGME49_021500, TGME49J) 19630, TGME49_061720 and TGME49_076220
Infection (Dengue virus): IL-10, fibrinogen, C4A, immunoglobulin, tropomyosin, albumin,
SCSb-9 complement complex (host); NS-1

Infection (*Streptococcus pneumonia*): stratifin, cullin 1, selenoprotein K, metal response
element binding transcription factor 2, prostaglandin E synthase 2, HLA-B associated
transcript 4, zinc finger protein (C2H2 type) 276, GCIP-interacting protein p29, mitochondrial
ribosomal protein L20, aryl hydrocarbon receptor nuclear translocator-like, secretory carrier
membrane protein 1, nuclear receptor subfamily 5, group A, member 2, NIMA (never in
mitosis gene a)-related expressed, kinase 7, ribosomal protein L28, ribosomal protein S25,
lysosomal-associated protein transmembrane 5, neural precursor cell expressed,
developmentally, down-regulted gene 4, alpha glucosidase 2, alpha neutral subunit, coatomer
protein complex, subunit beta 2 (beta prime), ribosomal protein L3, NADH dehydrogenase
(ubiquinone) 1 alpha, subcomplex, assembly factor 1, isoprenylcysteine carboxyl
methyltransferase, , cytoplasmic polyadenylation element binding protein 3, mannoside
acetylglucosaminyltransferase 1, RNA-binding region (RNP1, RRM) containing 1, , folate
receptor 4 (delta), ATPase, H+ transporting, lysosomal 50/57 kDa, V1, subunit H, zinc finger,
DHHC domain containing 6, phosphoribosyl pyrophosphate synthetase-associated, protein 2,
choline/ethanolaminephosphotransferase, , solute carrier family 38, member 1, ATP
synthase, H+ transporting, mitochondriaL F0, complex, subunit f, isoform 2, glucose
phosphate isomerase 1, 2'-5' oligoadenylate synthetase 1A, tyrosine hydroxylase,
hemoglobin alpha, adult chain 1, selenoprotein P, plasma, 1, acetyl-Coenzyme A
dehydrogenase, long-chain, mannosidase, beta A, lysosomal, , deltex 3 homolog
(*Drosophila*), ras homolog gene family, member AB, estrogen receptor 1 (alpha),
phosphoglycerate kinase 1, , keratin complex 2, basic, gene 8, emerin, nucleoporin 153,
formin 2, prothymosin alpha, synapsin 1, , cullin 4B, regulator of chromosome condensation
(RCC1) and, BTB (POZ) domain containing protein 1, , immediate early response 5, SAM
domain and HD domain, 1, tumor rejection antigen gp96, lymphocyte antigen 6 complex,
locus E, , DAZ associated protein 2, general transcription factor II I, RNA polymerase II
transcriptional coactivator, SWI/SNF-related, matrix-associated actin-dependent, regulator of

TABLE B2-continued

Diagnostic Markers chromatin, subfamily a, containing DEAD/H, box 1, structure specific recognition protein 1, ankyrin repeat and FYVE domain containing 1, SET translocation, myocyte enhancer factor 2A, homeo box D9, H2A histone family, member Z, cellular nucleic acid binding protein, , golgi reassembly stacking protein 2, cathepsin L, eukaryotic translation initiation factor 5, ubiquitin specific protease 9, X chromosome, proteasome (prosome, macropain) subunit, alpha type 7, pescadillo homolog 1, containing BRCT domain, (zebrafish), heterogeneous nuclear ribonucleoprotein K, DEAD (Asp-Glu-Ala-Asp) box polypeptide 52, sorting nexin 5, cathepsin B, DnaJ (Hsp40) homolog, subfamily B, member 9, ribosomal protein S3a, , cytoplasmic polyadenylation element binding protein 4, 5'-3' exoribonuclease 2, small nuclear ribonucleoprotein polypeptide F, , arachidonate 5-lipoxygenase activating protein, cytochrome c oxidase, subunit Vic, RIKubiquinol cytochrome c reductase core protein 2, lactate dehydrogenase 2, B chain, ubiquinol-cytochrome c reductase core protein 1, ATP synthase, H+ transporting, mitochondrial F0, complex, subunit b, isoform 1, microsomal glutathione 5-transferase 1, ras homolog gene family, member A, RAB7, member RAS oncogene family, EGF-like module containing, mucin-like, hormone, receptor-like sequence 1, annexin A6, mitogen activated protein kinase 3, tyrosine kinase, non-receptor, 2, villin 2, tubulin, beta 5, catenin src (host); Pneumolysin, pneumococcal histidine triad D (PhtD), pneumococcal histidine triad E (PhtE), LytB, and pneumococcal choline-binding protein A (PcpA)

Infection (*Mycoplasma pneumonia*): DnaK, L7/L12, P1, exotoxin

Infection (*Campylobacter jejuni*): gyrA, 16S rDNA, or flaA/flaB

Infection (*Bacillus anthracis*): Lethal factor, HtrA (BA3660), NlpC/P60-domain endopeptidase (BA1952), BA0796 locus (BA0796), SAP Infection (West Nile virus):

Infection (Human papilloma virus): E6, E7

Infection: RNase 7 (host)

In some instances, the present method is used to inform the subject from whom the sample is derived about a health condition thereof. Health conditions that may be diagnosed or measured by the present method, device and system include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause. The following Table B3 provides a list of biomarker that can be detected using the present invention, and their associated health conditions.

TABLE B3

Diagnostic Markers

| Health Condition | Source | Marker |
|---|---|---|
| Diabetes | Saliva miscellaneous | pIgR, Arp 3, CA VI, and IL-1Ra; PLS-2, LEI, and IGJ chain, resistin ATP-binding cassette, sub-family C (CFTR/M RP), member 8; ATP-binding cassette, sub-family C (CFTR/MRP), member 9; angiotensin I converting enzyme (peptidyl-dipeptidase A) 1; adenylate cyclase activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product-specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes insipidus, neurohypophyseal); bombesin receptor subtype 3; betacellulin; benzodiazepine receptor (peripheral); complement component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 |

TABLE B3-continued

Diagnostic Markers

| Health Condition | Source | Marker |
|---|---|---|
| | | molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine palmitoyltransferase I; carnitine palmitoyltransferase II; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; forkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; glucagon-like peptide 1 receptor; guanine nucleotide binding protein (G protein), beta polypeptide 3; glutamic-pyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like growth factor binding protein 1; insulin-like growth factor binding protein 3; inhibitor of kappa light polypeptide gene enhancer in B-cells, kinase beta; interleukin 10; interleukin 18 (interferon-gamma-inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor co-repressor 1; neurogenic differentiation 1; nuclear factor of kappa light polypeptide gene enhancer in B-cells 1(p105); nerve growth factor, beta polypeptide; non-insulin-dependent Diabetes Mellitus (common, type 2) 1; non-insulin-dependent Diabetes Mellitus (common, type 2) 2; Noninsulin-dependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; nuclear respiratory factor 1; oxytocin, prepro-(neurophysin I); purinergic receptor P2Y, G-protein coupled, 10; purinergic receptor P2Y, G-protein coupled, 12; purinergic receptor P2Y, G-protein coupled, 2; progestagen-associated endometrial; protein (placental protein 14, pregnancy-associated endometrial alpha-2-globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; endothelial growth factor-related protein; phosphoinositide-3-kinase, catalytic, alpha polypeptide; phosphoinositide-3-kinase, regulatory |

TABLE B3-continued

Diagnostic Markers

| Health Condition | Source | Marker |
|---|---|---|
| | | subunit 1 (p85 alpha); phospholipase A2, group XIIA; phospholipase A2, group IID; plasminogen activator, tissue; patatin-like phospholipase domain containing 2; proopiomelanocortin (adrenocorticotropin/beta-lipotropin/alpha-melanocyte stimulating hormone/beta- melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B'(PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandin-endoperoxide synthase 2 (prostaglandin G/H synthase and cyclooxygenase); protein tyrosine phosphatase, mitochondrial 1; Peptide YY retinol binding protein 4, plasma (RBP4); regenerating islet-derived 1 alpha (pancreatic stone protein, pancreatic thread protein); resistin; ribosomal protein S6 kinase, 90 kDa, polypeptide 1; Ras-related associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1(ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMG-box); transforming growth factor, beta 1 (Camurati-Engelmann disease); transglutaminase 2 (C polypeptide, protein-glutamine-gamma-glutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondrial, proton carrier); upstream transcription factor 1; urotensin 2; vascular cell adhesion molecule 1; vascular endothelial growth factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin; interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline |
| Metabolic syndrome/ prediabetes | Serum | GFAP autoantibodies |
| Kidney failure/ disease | saliva miscellaneous | Lactoferrin, uric acid, cortisol, alpha-amylase ADBP-26, NHE3, KIM-1, glutamyltransferase, N-acetyl-beta-D-glucosaminidase, lysozyme, NGAL, L-FABP, bikunin, urea, |

TABLE B3-continued

Diagnostic Markers

| Health Condition | Source | Marker |
|---|---|---|
| | | prostaglandins, creatinine, alpha-1-microglobulin, retinol binding protein, glutathione-S-transferases, adiponectin, beta-2-macroglobuin, calbindin-D, cysteine-rich angiogenic inducer 61, endothelial/epithial growth factors, alpha-1-acid glycoprotein (orosomucoid), prealbumin, modified albumin, albumin, transferrin, alpha-1-lipoprotein, alpha-1-antitrypsin matrix metalloproteinases (MMPs), alpha-1-fetoprotein, Tamm Horsfall protein, homoarginine, interleukin 18, monocyte chemotactic protein-1 (MCP-1), Lipocalin, VCAN, NRP1, CCL2, CCL19, COL3A1, GZMM, alpha-galactosidase, casein kinase 2, IP-10, Mig, I-TAC, MIP-1α, MIP-3α, and MIP-1β, alpha-2-glycoprotein-Zinc, leucine-rich alpha-2-glycoprotein, uromodulin, Pacsin 2, hepcidin-20, hepcidin-25, AIF-2, urinary type-IV collagen, lipocalin-type prostaglandin D synthase (L-PGDS), urinary neutrophil gelatinase-associated lipocalin (uNGAL), Annexin A1, Rab23, Shh, Ihh, Dhh, PTCH1, PTCH2, SMO, Gli1, Gli2, Gli3, TLR4, cystatin C, AQPI, AQP2, AQP3, NKCC2, NaPill, DAHKSEVAHRFKD<br>[RNA:] SLC12A1, UMOD, vWF, MMPI, MMP3, SLC22A6, SLC22A 8, SLC22A 12, podocin, cubulin, LRP2, AQP9, and albumin, carcinoembryonic antigen (CEA), mucin, alpha-fetoprotein, tyrosinase, melanoma associated antigen, mutated tumor protein 53, p21, PUMA, prostate-specific antigen (PSA) or thyroglobulin, von Willebrand factor (VWF), thrombin, factor VIII, plasmin, fibrin, osteopontin (SPP1), Rab23, Shh, Ihh, Dhh, PTCH1, PTCH2, SMO, Gli1, Gli2, Gli3 |
| Liver failure/ disease | miscellaneous | Carnitine; Cholic Acid; Chenodeoxycholic, Deoxycholic, Lithocholic, Glycocholic; Prostaglandin E2; 13,14-dihydro-15-keto Prostaglandin A2; Prostaglandin B2; Prostaglandin F2a; 15-keto-Prostaglandin F2α; 6-keto-Prostaglandin F1α; Thromboxane B2; 11-dehydro-Thromboxane B2; Prostaglandin D2; Prostaglandin J2; 15-deoxy-Δ12,14-Prostaglandin J2; 11β-Prostaglandin F2α; 5(S)-Hydroxyeicosatetraenoic acid; 5(S)-Hydroxyeicosapentaenoic acid; Leukotriene B4; Leukotriene B5; Leukotriene C4; Leukotriene D4; Leukotriene E4; Leukotriene F4; 12(S)-Hydroxyeicosatetraenoic acid; 12(S)-Hydroxyeicosapentaenoic acid; 15(S)-Hydroxyeicosatetraenoic acid; 15(S)-Hydroxyeicosapentaenoic acid; Lipoxin A4; 8(S)-Hydroxyeicosatetraenoic acid; 9-Hydroxyeicosatetraenoic acid; 11-Hydroxyeicosatetraenoic acid; 8-iso-Prostaglandin F2α; 9-Hydroxyoctadecadienoic acid; 13-Hydroxyoctadecadienoic acid; 20(5)-Hydroxyeicosatetraenoic acid; 9,10-Epoxyoctadecenoic acid; 12,13-Epoxyoctadecenoic acid; 12,13-Dihydroxyoctadecenoic acid; 5,6-Epoxyeicosatrienoic acid; 11,12-Epoxyeicosatrienoic acid; 14,15-Epoxyeicosatrienoic acid; 5,6-Dihydroxyeicosatrienoic acid; 8,9-Dihydroxyeicosatrienoic acid; 11,12-Dihydroxyeicosatrienoic acid; 14,15-Dihydroxyeicosatrienoic acid; 14,15-Epoxyeicosatetraenoic acid; 17,18-Epoxyeicosatetraenoic acid; 14,15-Dihydroxyeicosatetraenoic acid; 17,18-Dihydroxyeicosatetraenoic acid; 19,20-Dihydroxydocosapentaenoic acid; diacetylspermine, hemopexin, TLR4 |
| Heart failure | miscellaneous | SFRP-3, NT-proBNP, troponin T, SKITHRIHWESASLL (SEQ ID NO: //), AHKSEVAHRFK (SEQ ID NO: //), uroguanylin, BNP |
| Cardiovascular health | miscellaneous | miR-378, miR-497, miR-21, miR-15b, miR-99a, miR 29a, miR-24, miR-30b, miR-29c, miR-331.3p, miR-19a, miR-22, miR-126, let-7b, miR-502.3, and miR-652<br>IL-16, sFas, Fas ligand, MCP-3, HGF, CTACK, EOTAXIN, adiponectin, IL-18, TIM P.4, TIM P.1, CRP, VEGF, and EGF |
| | saliva | C-reactive protein (CRP); myoglobin (MYO), creatinine kinase myocardial band (CK-MB), cardiac troponins (cTn), and myeloperoxidase; TNF-α, and MMP-9; CD40 |
| High blood pressure | saliva | lysozyme |
| Tiredness/ fatigue | urine | endorepellin |
| | saliva | PPGKPQGPPPQGGNQPQGPPPPPGKPQ (SEQ ID NO: //); GNPQGPSPQGGNKPQGPPPPPGKPQ (SEQ ID NO: //); SPPGKPQGPPQQEGNKPQGPPPPPGKPQ (SEQ ID NO: //) |
| | urine | human herpesvirus 6, human herpesvirus 7, human cytomegalovirus, and Epstein-Barr virus (EBV) |
| | miscellaneous | GGHPPPP (SEQ ID NO: //), ESPSLIA (SEQ ID NO: //); |

TABLE B3-continued

Diagnostic Markers

| Health Condition | Source | Marker |
|---|---|---|
| Malnutrition | Saliva | sIgA |
| Depressive disorder | miscellaneous | Secretogranin, VGF |
| Alzheimer's disease | CSF, serum, saliva | β-amyloid(1-42), β-amyloid(1-40), tau, phosphor-tau-181 |
| Stress | saliva | Cortisol, dehydro-androsteronesulfate; 17-ketosteroidsulfate; dehydro-epiandrostronesulfate; corticosteroid, 17-hydroxycorticosteroid, chromogranin A, alpha-amylase, secretary IgA, lysozyme, growth hormone, oxytocin |
|  | miscellaneous | aldose reductase, apoptosis signal-regulating kinase 1, aquaporin 5, beta-endorphin, betaine GABA transporter, caspase recruitment domain protein 9, caspase 8, cyclin D, cyclooxygenase 2, cytochrome P450, cytochrome c, c-fos, c-jun, epidermal growth factor receptor, ferritin, glucocorticoid receptor, glucose regulated protein 58, glucose regulated protein 75, glutathione 5-transferase p, GroEL, heat shock protein 25/27, heat shock protein 40, heat shock protein 60, heat shock protein 70, heat shock protein 90, heat shock transcription factor-1, heme oxygenase-1, interleukin 113, interleukin 6, interleukin 8, interleukin 10, interleukin 12, laminin, leptin receptor, matrix metalloproteinase 9, metallothionein, Mek-1, Mekk-1, inducible nitric oxide synthase, peripheral benzodiazepine receptor, p38 MAPK, salivary alpha amylase, SAPK, serotonin, serotonin receptor, substance P, superoxide dismutase Mn, superoxide dismutase Cu/Zn, superoxide dismutase EC, transforming growth factor β, tumor suppressor p53, and vasoactive intestinal peptide |
| Circadian-rhythm | saliva | melatonin |
| Bone turnover/ Osteoporosis | Urine | Pyridinoline, deoxypyridinoline, collagen type 1 corss-linked N-telopeptide (NTX), collagen type 1 corss-linked C-telopeptide (CTX), bone sialoprotein (BSP), Tartrate-resistant acid phosphatase 5b |
|  | saliva | deoxypyridinium (D-PYR) and osteocalcin (OC), hepatocyte growth factor and interleukin-1 beta |
| Muscle damage | Serum, urine | Myoglobin, creatine kinase (CK), lactate dehydrogenase (LDH), aldolase, troponin, carbonic anhydrase type 3 and fatty acid-binding protein (FABP), transaminases |
| Exercise/ athletic activity | sweat serum saliva | urea Myostatin, follistatin-like related gene testosterone |
| Performance enhancement | miscellaneous | interleukin-6, interleukin-1 beta, G-CSF, interferon-gamma, interleukin-8, interleukin-9, MCP-1, MIP-beta, and/or TNF alpha |
| Energy balance (protein excretion/) energy status/ metabolic state | Serum Urine, sweat, feces miscellaneous | AMPK pre-albumin, retinol binding protein, urea cholesterol, lipoproteins, insulin, insulin C peptide, IGF binding proteins, e.g. IGF-BPI, liver enzymes |
| Growth | Saliva | IGF-1 |
| Andropause | saliva | testosterone; testosterone precursors such as pregnenolone, progesterone, 17-hydroxypregnenolone, 17-hydroxyprogesterone, dehydroepiandrosterone (DHEA) and delta-4-androstene-3,17-dione; testosterone and dihydrotestosterone metabolites such as the 17-ketosteroids androsterone and etiocholanolone, polar metabolites in the form of diols, triols, and conjugates, as well estradiol, estrogens, androsteindione, cortisol, DHEA, FSH (follicle stimulating hormone), LH (luteinizing hormone), and GnRH (gonadotropin-releasing hormone) |

TABLE B3-continued

Diagnostic Markers

| Health Condition | Source | Marker |
|---|---|---|
| Menopause | Saliva | Follicle stimulating hormone (FSH)<br>Estrogen and progesterone, testosterone, free testosterone, and edehydroepiandrosterone sulfate<br>(DHEAS), cortisol and dehydroepiandrosterone (DHEA) |
| Pregnancy/ fetal development | Saliva<br>urine<br>serum | progesterone<br>human chorionic gonadotropin, Levonorgestrel, alpha-fetoprotein<br>estradiol |
| Breast cancer | urine | 47D10 antigen, PTCD2, SLC25A20, NFKB2, RASGRP2, PDE7A, MLL, PRKCE, GPATC3, PRIC285 and GSTA4, MIPEP, PLCB2, SLC25A19, DEF6, ZNF236, C18orf22, COX7A2, DDX11, TOP3A, C9orf6, UFC1, PFDN2, KLRD1, LOC643641, HSP90AB1, CLCN7, TNFAIP2, PRKCE, MRPL40, FBF1, ANKRD44, CCT5, USP40, UBXD4, LRCH1, MRPL4, SCCPDH, STX6, LOC284184, F1123235, GPATC3, CPSF4, CREM, HIST1H1D, HPS4, FN3KRP, ANKRD16, C8 orf16, ATF71P2, PRIC285 |
| Prostate cancer | Serum/ saliva<br>Urine | Prostate specific antigen (PSA)<br><br>PCA3, GOLPH2, SPINK1, TMPRSS2:ERG |
| Infections | | See Table B2 |
| Dental caries/ periodontal disease | Saliva | aspartate aminotransferase (AST) and alkaline phosphatase (ALP), uric acid and albumin; 12-HETE; MMP-8, TIMP-1, and ICTP |
| Heavy metal poisoning | saliva | lead, cadmium |
| Drugs/drug metabolites | saliva<br><br><br><br><br>urine | marijuana, Cocaine (crystalline tropane alkaloid), methamphetamine, amphetamine, heroin, methyltestosterone, mesterolone, morphine, cyclophosphamide metabolites, Haloperidol, barbiturates; antipyrine, caffeine, cisplatin, cyclosporine, diazepam, digoxin, methadone, phenytoin, theophylline, tolbutamide, Nicotine/cotinine, cannabis<br>trichloroethanol glucuronide, Anabolic steroids, Androstenedione, Benzodiazepines, Chlordiazepoxide, Lorazepam, Zidovudine |
| Allergies | saliva | Allergen-specific IgAs (see Tables B7 and 9) |

In some instances, the biomarker that can be detected by the present method is an antibody in a sample, e.g., a diagnostic sample, that is probative for diagnosing a disease or health condition of the subject from which the sample is derived.

Tables B4 provides a list of autoantibody targets, which can be used, in whole or as an epitope fragment, as a capture agent in the present method to measure the amount of the epitope-binding antibody analyte in a sample and thereby diagnose the associated disease or health condition, e.g., an autoimmune disease. In some cases, the disease or health condition is related to an immune response to an allergen. Table B5 provides a list of allergens, which can be used, in whole or as an epitope fragment, as a capture agent in the present method to measure the amount of the epitope-binding antibody analyte in a sample and thereby diagnose the associated disease or health condition, e.g., an allergy. In certain instances, the disease or health condition is related to an infectious disease, where the infectious agent may be diagnosed based on information including the measured amount of antibodies against one or more epitopes derived from the infectious agent (e.g., lipopolysaccharides, toxins, proteins, etc.). Tables B6 provides a list of infectious-agent derived epitopes which can be used, in whole or as an epitope fragment, as a capture agent in the present method to measure the amount of the epitope-binding antibody analyte in a sample and thereby diagnose the associated disease or health condition, e.g., an infection. Other epitopes or antigens that may be suitable for use in the present diagnostic method are described in, e.g., PCT App. Pub. No. WO 2013164476, which is incorporated herein by reference.

TABLE B4

Diagnostic Autoantibody Epitopes

| Disease/condition | Autoantibody Targets |
|---|---|
| Cancer | ACAA2; ANXA13; AQP2; ASPA; BCL2; BCL2L1; BIK; CD160; CD37; CDK4; CDK6; CHEK2; CITED2; CNN2; CTSC; CTSZ; CycE2; ELK1; FGF10; FN1; GATA3; GJA1; GNRH1; GRB2; HBB; HBE1; HIST2H2AA; HPRT1; ID2; IER2; IFI27; IFITM1; IFITM2; IL15; IL18; IL8; IL9; KRT16; LALBA; LDHA; |

TABLE B4-continued

Diagnostic Autoantibody Epitopes

| Disease/condition | Autoantibody Targets |
|---|---|
| | LDHB; LECT1; MAFK; Mage3; MAGEA3; MMP2; NPPB; OAS1, p21; p53; PCNA; PENK; PEX3; PHB; PHYH; PI3; PKBα; PLN; S100A7; SCAMP1; SCGB1A1; SLC38A5; SNRP2; SNX9; SST; SSTR2; TACSTD1; TNNC2; TOB1; TSG101; VDRIP; WNT2, p62 and Koc; ZFP161, Ubiquilin-1, HOX-B6, YB-1, Osteonectin, ILF3 |
| Squamous cell lung carcinoma | protein kinase C and p53-binding protein (TP53 BP), lymphoid blast crisis oncogene (LBC), |
| Small cell lung cancer | SOX families B1 and B2, MUC-1, |
| Lung cancer | MUC-1, p53, surviving, LAMR1, annexin I, 14-3-3-theta; AKR1B10; GOT2; HNRPR; PDIA3; NME2; RTN4; H1FX; G3BP; HSPCA; ACTN4; PGP9.5; |
| Colorectal cancer | MUC-1, surviving, p-53; translationally controlled tumor protein; HSPC218; Ribosomal protein S18; v-Fte-1; v-Fos transformation effector protein; MAGEA3, SSX2, NY-ESO-1, HDAC5, MBD2, TRIP4, NY-CO-45, KNSL6, HIP1R, Seb4D, KIAA1416, and LMNA; UCHL3 |
| Hepatocellular carcinoma | fibrillarin and p330d/CENP-F, insulin-like growth factor II mRNA-binding proteins (IMP) 1, IMP3 and p53, NOR-90, nucleophosmin/protein B23, cyclin B1, DNA topoisomerase II (topo II), p62, HCC1, SG2NA, MAGE-C2, AF146731; AF219119; AF146019; Ligatin; AF220416; AF218421; AF257175; AF244135; AF243495; AF287265; AF258340; AF270491; AF286340; small nuclear RNA-associated sm-like protein; Dna J protein; CENP-F; translationally controlled tumor protein; LDH-A; Albumin; Hsp89αΔN; SEC63; AF100141; 14, 5 kDa protein; GCF2; Metallopanstimulin 1; SMP-30 D31815; Cg1 protein,; C3VS protein; F1-ATPase, β subunit; Human ribosomal protein L10; Pre-apolipoprotein CIII; Galactose-1-phosphate-uridyl-transferase (GALT); DNA polymerase Δ, small subunit; Mitochondrial DNA |
| Renal cancer | AF257175; small nuclear RNA-associated sm-like protein; Dna J protein; smooth muscle protein 22-alpha (SM22-alpha); carbonic anhydrase I (CAI) |
| Acute leukemia | Rho GDP dissociation inhibitor 2, γ-actin, F-actin capping protein (CAPZA1), heterogeneous nuclear ribonucleoprotein L (hnRNP L), tubulin-α 6, PCNA |
| Chronic lymphocytic leukemia | KIAA1641; PIPMT; FosB; ZNF268; SEBD4; Ikaros; p75/LDEGF; CHIP; PYGB; ZNF148; KIAA0336; RPL11; FMNL; HGRG8 |
| non-Hodgkin's lymphoma | CENP-F, |
| Multiple myeloma | NY-ESO-1 |
| melanoma | NY-ESO-1, MAGE-1, BAGE, GAGE, MART-1/melan A, gp100, and tyrosinase |
| Pancreatic cancer | Calreticulin, DEAD-box protein 48 (DDX48) |
| Ovarian cancer | ACSBG1, AFP, CSNK1A1 L, DHFR, MBNL1, TP53, PRL, PSMC1, PTGFR, PTPRA, RAB7L1, and SCYL3, her2/neu, MUC1, c-myc, ECPKA, and NY-ESO-1, p53, UBQLN1, HOXB6, TOP2A, putative helicase-RUVBL (RUVBL), HMBA-inducible (HEXIM1), DDX5 and HDCMA |
| Prostate cancer | Bcl2, NY-ESO-1, survival protein lens epithelium-derived growth factor p75 (LEDGF/p75), PRDX6/AOP2, clusterin, DJ-1, superoxide dismutase, alcohol dehydrogenase, HSP70, HSP27/HSPB1, lactoylglutathione lyase, glucose-regulated protein-78 kDa (GRP78), p62, Koc, and IMP1, α-Methylacyl-coenzyme A racemase and 5-α-reductase, AKRIA1; Brd2; C17 orf 25; CAPZA1; c-MYC; Cyclin A; Cyclin B1; Cyclin D1; Drebrin; eIF4G1; HIP1; HSPA8; Lactoylglutathione lyase; MAD-CT-1; MAD-CT-2; No55; P53; P62; P90; PP4R; PIP; PSA; RPL13a; RPL22; Survivin; Syntenin 1; TDP-43; VCP; vWF; Lage-1, and Xage-1; bromo domain-containing protein 2 (BRD2), ribosomal proteins L22 and L13a, XP_373908 |
| Breast cancer | p53, c-myc, NY-ESO-1, BRCA1, BRCA2, HER2, MUC1, IGFBP-2, TOPO2α, ribosomal protein S6, eukaryotic elongation factor 2, eukaryotic elongation factor 2 kinase, and heat shock protein 90 (HSP90), Ku protein, topoisomerase I, and the 32-kDa subunit of replication factor A; CENP-F; AF146731; int-2, pentraxin I, integrin beta5, cathepsin L2 and S3 ribosomal protein; RNA-binding protein regulatory subunit (RS), DJ-1 oncogene, glucose-6-phosphate dehydrogenase, heat shock 70-kDa protein 1 (HS71), and dihydrolipoamide dehydrogenase |
| Nasopharyngeal carcinoma | MAGE, HSP70, Fibronectin, CD44, EBV antigens |
| Oral cancer | Cyclin B1, p53 |
| Oral squamous cell carcinoma | p53 |
| Head and neck squamous cell carcinoma | CASP-8, SART-1, TREX1, 3' repair exonuclease; BRAP (BRCA1 associated): Nuclear localization protein; Trim 26 zinc finger domains; GTF21 transcription factor. Murine homolog TF11-1; NSEP1 (YB-1) transcription factor; MAZ transcription factor associated with c-myc; SON (DBP-5; KIAA1019; NREBP DNA binding protein); NACA nascent polypeptide-associated complex; NUBP2 nucleotide binding protein; EEF2 Translation elongation factor 2; GU2 Putative RNA helicase; RPLI3A ribosomal protein; SFRS21P (CASP11; SIP1; SRRP1290 splicing factor); |

TABLE B4-continued

Diagnostic Autoantibody Epitopes

| Disease/condition | Autoantibody Targets |
|---|---|
| | RPS12 ribosomal protein; MGC2835 RNA helicase; TMF1, TATA modulatory factor; PRC1 regulator of cytokinesis; KRT14 keratin 14; Viniculin; H2AFY histone family member; SLK (KIAA02304) Ste related kinase; NOL3 (ARC) nuclear protein 3, apoptosis repressor; DNAJA2 member of Hsp40 family; DNAJA1 member of HSP40 family; LINE-1 retrotransposon; MOG (HSPC 165) Homolog of yeast protein; LIMS1 (PINCH): LIM and senescent antigen-like domain; COPB2 coatomer protein complex subunit protein; FLJ22548 hypothetical protein; C21orf97; FLJ21324; MGC15873; SSNA1 Sjogrens syndrome nuclear autoantigen 1; KIAA0530, zinc finger domain; rat stannin; hypothetical protein DKFZp4340032; human FLJ23089; PC326 |
| Esophageal cancer | NY-ESO-1; SURF1, HOOK2, CENP-F, ZIC2, hCLA-iso, Ki-1/57, enigma, HCA25a, SPK, LOC146223 and AGENCOURT_7565913 |
| Metabolic syndrome/ prediabetes | GFAP |
| Diabetes | Zn transporter 8, glutamic acid decarboxylase (GAD), CD38, gad65, IA2, insulin, MRPS31, ICA1, L-type voltage gated calcium channel; SNRPB2; DDX42; C11orf63; TCOF1; TSSK2; KDM4B; PDGFB; LTK; RPL14; VIM; GTF2I; BCL2L13; LARP6; DKFZP434K028; USP39; SERBP1; CCL19; GAD2; MCM10; ZNF688; PTEN; RP6-166C19.11; GIPC1; TIGD1; CCDC131; HTF9C; SOX5; MCF2L; TRAF3IP1; 6CKINE; ACY3; AMMECR1L; ARHGAP9; ASNS; BATF2; BMX; C9ORF25; CDC2; CHGB; CXORF38; CXORF56; DMD; ECHDC1; EIF3F; EPHA2; ERMN; FAM136A; (includes; EG: 84908); FILIP1; FLT1; GART; GIMAP6; GNG7; GTF2F1; HGS; IFI6; KDM4B; LACE1; LGALS1; LGALS7; LIMS2; LTK; LUC7L; NCAPG; (includes; EG: 64151); NME6; NUPL1; PAK4; PDE4DIP; PSIP1; RAB20; RNGTT; RPS3; SPG20; TALDO1; TBRG1; THAP1; TRAF3IP2; UBL4A; ZC3HC1; ZNF131; RAD51AP1; HADH; (HADH); C11orf16; (C11orf16); TAC3; ABR; ECE1; PPP1R2; GRINL1A; ABR; C19orf44; MUSTN1; ETHE1; BMI1; BAZ2B; ; TBC1D22A; CAMK2N2; ASS1; CCNY; MARK2; RAD51AP1; RAB38; RIOK1; HSP90AA1; C11orf74; ARID3A; LMOD1; CAPRIN1; ITGB3BP; MND1; SGK; NADK; MED9; LDHA; ARHGAP26; ANKRA2; CRY2; IL23A; DUSP14; ZBTB44; SIRT1; SLC2A3; GPR172B; CCDC89; BATF; HMOX1; ARRDC1; USF2; GBGT1; EDC3; SGIP1; GCGR; ZRANB2; NLGN4Y; GJB6; CDK10; PSG1; CCDC74A; DENND1C; MAP2K6 |
| Autoimmune heart disease | cardiac troponin I (cTnI) |
| Immunoglobulin A nephropathy | PRKD1, MATN2, DDX17, UBE2W, CDKN1 B, SOD2, FLOT2, IQCK, BLZF1, BRD9, CDS2, EFNA3, EIF4A2, FLU, LIMCH1, MAGEA4, MEF2D, MLLT6, MRPL28, MUTED, NKAIN4, PCTK1, PLXNA1, PODN, POLH, PRKD2, RNF1 1 3A, SEPT5, TNS1, TOM1, TRPV4, USP12, ZMYM3, CIAPIN1, GDI2, HSPA8, SERPINA5 and TGM1 |
| End stage renal disease | IGLC1; IGHG1; EDC3; IGHG1; APEX2; CD3D; TRIM21; IGKV1-5; IGHG3; CTLA-FC; CD7; CLIP4; MAPRE1; SNRPB2; IGHG1; ZBTB44; CD3D; IGHG1; TRAM1; ERR beta-; LBD; CNBP; OLFM1; IGHM; SIRT5; CEP290; PHLDA1 |
| Glomerular nephritis | |
| Addison's disease | 21-hydroxylase, P450-17α-hydroxylase (17OH) and P450-side chain cleavage (SCC) |
| Primary ovarian insufficiency | Jo-1, proteinase 3 (PR3) |
| Sjögren's syndrome | IgA, IgG, IgM autoantibodies; IgA, lactoferrin and beta2-microglobulin; lysozyme C, and cystatin C, amylase and carbonic anhydrase SSA/Ro; LA/SS-B |
| Systemic lupus erythematosus (SLE) | CDC25B, APOBEC3G, ARAF, BCL2A1, CLK1, CREB1, CSNK1G1, CSNK2A1, CWC27, DLX4, DPPA2, EFHD2, EGR2, ERCC2, EWSR1, EZH2, FES, FOS, FTHL17, GEM, GNA15, GNG4, HMGB2, HNRNPUL1, HOXB6, ID2, IFI35, IGF2BP3, IGHG1, JUNB, KLF6, LGALS7, LIN28A, MLLT3, NFIL3, NRBF2, PABPC1, PATZ1, PCGF2, PPP2CB, PPP3CC, PRM1, PTK2, PTPN4, PYGB, RET, RPL18A, RPS7, RRAS, SCEL, SH2B1, SMAD2, STAM, TAF9, TIE1, UBA3, VAV1, WT1, ZAP70, or ZNRD1 KIT, C6orf93, RPL34, DOM3Z, COPG2, DNCL12, RRP41; FBXO9; RALBP1, PIAS2; EEF1D; CONI; KATNB1; POLR2E; CCT3; KIAA0643; RPL37A, GTF2H2; MAP2K5; CDK3; RPS6KA1; MARK4, MTO1; MGC42105; NFE2L2; WDR45L, STK4, PFKFB3; NTRK3; MLF1; TRIM37, ACTL7B, RPL18A, CKS1B; TUBA1, NME6, SUCLA2, IGHG1, PRKCBP1; BAG3; TCEB3; RPL15, SSX4; MAP2K7; EEF1G; RNF38, PHLDA2, KCMF1; NUBP2, VPS45A SSA/Ro; dsDNA; Smith; histones; thrombin; v-Fos transformation effector protein, tryptase, Sm antigen, beta 2; cardiolipin; glycoprotein I β2; Endothelial PC/activated PC receptor; human gamma enolase |
| CREST syndrome | centromere |

TABLE B4-continued

Diagnostic Autoantibody Epitopes

| Disease/condition | Autoantibody Targets |
|---|---|
| Systemic sclerosis | Type I topoisomerase |
| Primary biliary cirrhosis | nucleoporin 62, Sp100 nuclear antigen, nucleoporin 210 kDa, mitochondria, mitochondrial pyruvate dehydrogenase (PDH) or E3 binding protein |
| Dermatitis herpetiformis | eTG |
| Miller-Fisher Syndrome | ganglioside GQ1B |
| Wegener's granulomatosis | c-ANCA |
| Neuropathies | ganglioside GD3, ganglioside GM1, GA1, GM2, MAG |
| microscopic polyangiitis | p-ANCA |
| Polymyositis | Signal recognition particles |
| scleromyositis | exosome complex Signal recognition particles |
| myasthenia gravis | nicotinic acetylcholine receptor Signal recognition particles, muscle-specific kinase (MUSK) Signal recognition particles |
| Lambert-Eaton myasthenic syndrome | voltage-gated calcium channel (P/Q-type) |
| Hashimoto's thyroiditis | thyroid peroxidase |
| Graves' disease | TSH receptor |
| paraneoplastic cerebellar syndrome | Hu, Yo (cerebellar Purkinje Cells), amphiphysin |
| encephalitis | voltage-gated potassium channel (VGKC), N-methyl-D-aspartate receptor (NMDA) |
| Sydenham's chorea | basal ganglia neurons |
| antiphospholipid syndrome | glycoprotein 1 (2GPI), Endothelial PC/activated PC receptor |
| Systemic vasculitis | proteinase 3 (PR3) and myeloperoxidase (MPO) |
| Neuromyelitis | aquaporin-4 |
| Allergies | Allergen-specific IgAs |
| Rheumatoid arthritis | Rheumatoid factor, cyclic citrullinated protein; human cartilage gp39 peptides and type II collagen; citrullinated fibrinogen, citrullinated vimentin, citrulline-substituted filaggrin peptides, hnRNP-A2/B1, BiP, tryptase |
| Asthma | tryptase |
| Multiple sclerosis | myelin basic protein, spectrin, fodrin, myelin oligodentrocyte glycoprotein, proteolipid protein (PLP), 2',3'-cyclic nucleotide-phosphodiesterase (CNP), Glc($\alpha$1,4)Glc($\alpha$) (GAGA4), Glc($\alpha$1,6)Glc($\alpha$) (GAGA6) |
| amyotrophic lateral sclerosis (ALS) | HMGB1 |
| Idiopathic thrombocytopenic purpura | platelet glycoprotein (GP) IIb/IIIa, GPIb/IX, GPIa/IIa |
| Thrombosis | thrombomodulin |
| Cardiovascular disease | Endothelial PC/activated PC receptor; IL-1alpha, alpha-actinin-2 (aActn2); alpha-Myosin Heavy Chain (alpha-MHC-S 1); SI fragment of alpha-Myosin Heavy Chain 6 (alpha-MHC6-SI); alpha-Myosin Heavy Chain 7 (MyHC7) |
| post-streptococcal disease such as PANDAS, post-GABHS glomerulonephritis, rheumatic fever, autism and Sydenham's chorea | ELAVL2, ELAVL3, ELAVL4, Nova-1, Nova-2, Cdr1, Cdr2; and Cdr3 |
| Parkinson's Disease | alpha-synuclein; myelin basic protein (MBP), proteolipid protein (PLP), myelin oligodendrocyte glycoprotein (MOG), myelin associated glycoprotein (MAG), oligodendrocytes specific protein (OSP) |
| pernicious anemia | Vitamin $B_{12}$ |

TABLE B5

Allergen Epitopes

| Source | Allergen |
|---|---|
| mites | Acas13, Blot1, Blot3, Blot4, Blot5, Blot6, Blot10, Blot11, Blot12, Blot13, Blot19; American house dust mite (Derf1, Derf2, Derf3, Derf7, Derf10, Derf11, Derf14, Derf15, Derf16, Derf17, Derf18w); house dust mite (Derm1); European house dust mite (Derp1, Derp2, Derp3, Derp4, Derp5, Derp6, Derp7, Derp8, Derp9, Derp10, Derp11, Derp14, Derp20, Derp21); mite (Eurm2; Eurm14); storage mite (Glyd2, Lepd2, Lepd5, Lepd7, Lepd10, Lepd13, Tyrp2, Tyrp13); *Dermatophagoides farinae* (Derf1.0101, Derf1.0102, Derf1.0103, Derf1.0104, Derf1.0105, Derf2.0101, Derf2.0102, Derf2.0103, Derf2.0104, Derf2.0105, Derf2.0106, Derf2.0107, Derf2.0108, Derf2.0109, Derf2.0110, Derf2.0111, Derf2.0112, Derf2.0113, Derf2.0114, Derf2.0115, Derf2.0116, Derf2.0117); *Dermatophagoides pteronyssinus* (Derp1.0101, Derp1.0102, Derp1.0103, Derp1.0104, Derp1.0105, Derp1.0106, Derp1.0107, Derp1.0108, Derp1.0109, Derp1.0110, Derp1.0111, Derp1.0112, Derp1.0113, Derp1.0114, Derp1.0115, Derp1.0116, Derp1.0117, Derp1.0118, Derp1.0119, Derp1.0120, Derp1.0121, Derp1.0122, Derp1.0123, Derp2.0101, Derp2.0102, Derp2.0103, Derp2.0104, Derp2.0105, Derp2.0106, Derp2.0107, Derp2.0108, Derp2.0109, Derp2.0110, Derp2.0111, Derp2.0112, Derp2.0113); *Euroglyphus maynei* (Eurm2.0101, Eurm2.0102); *Glycyphagus domesticus* (Glyd2.0101, Glyd2.0201); and *Lepidoglyphus destructor* (Lepd2.0101, Lepd2.0101, Lepd2.0102, Lepd2.0201, Lepd2.0202) |
| Pollen | Short Ragweed (*Ambrosia artemisiifolia*) allergen, Amb a 1, Amba2, Amba3, Amba5, Amba6, Amba7, Amba8, Amba9, Amba10; *Betula verrucosa* allergen, Bet v 1, *Phleum pratense* allergen, Phl p 5); giant ragweed (Ambt5); mugwort (Artv1, Artv2, Artv3, Artv4, Artv5, Artv6); sunflower (Hela1, Hela2, Hela3); *Mercurialis annua* (Mera1); lamb's-quarters, pigweed (Chea1); white goosefoot (Chea2, Chea3); Russian-thistle (Salk1); Rosy periwinkle (Catr1); English plantain (Plal1); Japanese hop (Humj1); *Parietaria judaica* (Parj1, Parj2, Parj3); *Parietaria officinalis* (Paro1); *Ambrosia artemisiifolia* (Amba8.0101, Amba8.0102, Amba9.0101, Amba9.0102); *Plantago lanceolata* (Plal1.0101, Plal1.0102, Plal1.0103); and *Parietaria judaica* (Parj1.0101, Parj1.0102, Parj1.0201, Par2.0101, Parj2.0102, Parj3.0101, Parj3.0102), Bermuda grass (Cynd1, Cynd7, Cynd12, Cynd15, Cynd22w, Cynd23, Cynd24); orchard grass (Dacg1, Dacg2, Dacg3, Dacg5); meadow fescue (Fesp4w); velvet grass (Holl1); rye grass (Lolp1, Lolp2, Lolp3, Lolp5, Lolp11); canary grass (Phaa1); Timothy (Phlp1, Phlp2, Phlp4, Phlp5, Phlp6, Phlp11, Phlp12, Phlp13); Kentucky blue grass (Poap1, Poap5); Johnson grass (Sorh1); *Cynodon dactylon* (Cynd1.0101, Cynd1.0102, Cynd1.0103, Cynd1.0104, Cynd1.0105, Cynd1.0106, Cynd1.0107, Cynd1.0201, Cynd1.0202, Cynd1.0203, Cynd1.0204); *Holcus lanatus* (Holl1.0101, Holl1.0102); *Lolium perenne* (Lolp1.0101, Lolp1.0102, Lolp1.0103, Lolp5.0101, Lolp5.0102); *Phleum pratense* (Phlp1.0101, Phlp1.0102, Phlp4.0101, Phlp4.0201, Phlp5.0101, Phlp5.0102, Phlp5.0103, Phlp5.0104, Phlp5.0105, Phlp5.0106, Phlp5.0107, Phlp5.0108, Phlp5.0201, Phlp5.0202); and *Secale cereale* (Secc20.0101, Secc20.0201), Alder (Alng1); Birch (Betv1, Betv2, Betv3, Betv4, Betv6, Betv7); hornbeam (Carb1); chestnut (Cass1, Cass5, Cass8); hazel (Cora1, Cora2, Cora8, Cora9, Cora10, Cora11); White oak (Quea1); Ash (Frae1); privet (Ligv1); olive (Olee1, Olee2, Olee3, Olee4, Olee5, Olee6, Olee7, Olee8, Olee9, Olee10); Lilac (Syrv1); Sugi (Cryj1, Cryj2); cypress (Cupa1); common cypress (Cups1, Cups3w); mountain cedar (Juna1, Juna2, Juna3); prickly juniper (Juno4); mountain cedar (Juns1); eastern red cedar (Junv1); London plane tree (Plaa1, Plaa2, Plaa3); date palm (Phod2); *Betula verrucosa* (Betv1.0101, Betv1.0102, Betv1.0103, Betv1.0201, Betv1.0301, Betv1.0401, Betv1.0402, Betv1.0501, Betv1.0601, Betv1.0602, Betv1.0701, Betv1.0801, Betv1.0901, Betv1.1001, Betv1.1101, Betv1.1201, Betv1.1301, Betv1.1401, Betv1.1402, Betv1.1501, Betv1.1502, Betv1.1601, Betv1.1701, Betv1.1801, Betv1.1901, Betv1.2001, Betv1.2101, Betv1.2201, Betv1.2301, Betv1.2401, Betv1.2501, Betv1.2601, Betv1.2701, Betv1.2801, Betv1.2901, Betv1.3001, Betv1.3101, Betv6.0101, Betv6.0102); *Carpinus betulus* (Carb1.0101, Carb1.0102, Carb1.0103, Carb1.0104, Carb1.0105, Carb1.0106, Carb1.0106, Carb1.0106, Carb1.0106, Carb1.0107, Carb1.0107, Carb1.0108, Carb1.0201, Carb1.0301, Carb1.0302); *Corylus avellana* (Cora1.0101, Cora1.0102, Cora1.0103, Cora1.0104, Cora1.0201, Cora1.0301, Cora1.0401, Cora1.0402, Cora1.0403, Cora1.0404); *Ligustrum vulgare* (Ligv1.0101, Ligv1.01.02); *Olea europea* (Olee1.0101, Olee1.0102, Olee1.0103, Olee1.0104, Olee1.0105, Olee1.0106, Olee1.0107); *Syringa vulgaris* (Syrv1.0101, Syrv1.0102, Syrv1.0103); *Cryptomeria japonica* (Cryj2.0101, Cryj2.0102); and *Cupressus sempervirens* (Cups1.0101, Cups1.0102, Cups1.0103, Cups1.0104, Cups1.0105) |
| mold | *Alternaria alternata* allergen, Alt a 1, Alta3, Alta4, Alta5, Alta6, Alta7, Alta8, Alta10, Alta12, Alta13, *Aspergillus fumigatus* allergen, Asp f 1, Aspf2, Aspf3, Aspf4, Aspf5, Aspf6, Aspf7, Aspf8, Aspf9, Aspf10, Aspf11, Aspf12, Aspf13, Aspf15, Aspf16, Aspf17, Aspf18, Aspf22w, Aspf23, Aspf27, Aspf28, Aspf29); *Aspergillus niger* (Aspn14, Aspn18, Aspn25); *Aspergillus oryzae* (Aspo13, Aspo21); *Penicillium brevicompactum* (Penb13, Penb26); *Penicillium chrysogenum* (Pench13, Pench18, Pench20); *Penicillium citrinum* (Penc3, Penc13, Penc19, Penc22w, Penc24); *Penicillium oxalicum* (Peno18); *Fusarium culmorum* (Fuse1, Fusc2); *Trichophyton rubrum* (Trir2, Trir4); *Trichophyton tonsurans* (Trit1, Trit4); *Candida albicans* (Canda1, Canda3); *Candida boidinii* (Candb2); *Psilocybe cubensis* (Psic1, Psic2); shaggy cap (Copd, Copc2, Copc3, Copc5, Copc7); *Rhodotorula mucilaginosa* (Rhom1, Rhom2); *Malassezia furfur* (Malaf2, Malaf3, Malaf4); *Malassezia sympodialis* (Malas1, Malas5, Malas6, Malas7, Malas8, Malas9, Malas10, Malas11, Malas12, Malas13); *Epicoccum* |

TABLE B5-continued

Allergen Epitopes

| Source | Allergen |
|---|---|
| | *purpurascens* (Epip1); and *Alternaria alternate* (Alta1.0101, Alta1.0102), *Aspergillus versicolor* antigen, *S. chartarum* antigen), *Cladosporium herbarum* (Clah2, Clah5, Clah6, Clah7, Clah8, Clah9, Clah10, Clah12); *Aspergillus flavus* (Aspfl13); |
| mammals | *Bos domesticus* dander allergen, Bos d 2, Bosd3, Bosd4, Bosd5, Bosd6, Bosd7, Bosd8, Bosd2.0101, Bosd2.0102, Bosd2.0103, *Canis familiaris* allergen, Can f 1, Canf2, Canf3, Canf4, *Equus caballus* allergen, Equc1, Equc2, Equc3, Equc4, Equc5, *Felis domesticus* allergen, Fel d 1, Feld2, Feld3, Feld4, Feld5w, Feld6w, Feld7w, guinea pig (Cavp1, Cavp2); Mouse Urinary Protein (MUP, Musm1) allergen, Mus m 1, Rat Urinary Protein (RUP, Ratn1) allergen, Rat n 1., *Equus caballus* (Equc2.0101, Equc2.0102)) |
| Insects | Mosquito (Aeda1, Aeda2); honey bee (Apim1, Apim2, Apim4, Apim6, Apim7); bumble bee (Bomp1, Bomp4); German cockroach (Blag1, Blag2, Blag4, Blag5, Blag6, Blag7, Blag8); American cockroach (Pera1, Pera3, Pera6, Pera7); midge (Chit1-9, Chit1.01, Chit1.02, Chit2.0101, Chit2.0102, Chit3, Chit4, Chit5, Chit6.01, Chit6.02, Chit7, Chit8, Chit9); cat flea (Ctef1, Ctef2, Ctef3); pine processionary moth (Thap1); silverfish (Leps1); white face hornet (Dolm1, Dolm2, Dolm5); yellow hornet (Dola5); wasp (Pola1, Pola2, Pola5, Pole1, Pole5, Polf5, Polg5, Polm5, Vesvi5); Mediterranean paper wasp (Pold1, Pold4, Pold5); European hornet (Vespc1, Vespc5); giant asian hornet (Vespm1, Vespm5); yellowjacket (Vesf5, Vesg5, Vesm1, Vesm2, Vesm5, Vesp5, Vess5, Vesv1, Vesv2, Vesv5); Australian jumper ant (Myrp1, Myrp2); tropical fire ant (Solg2, Solg4); fire ant (Soli2, Soli3, Soli4); Brazilian fire ant (Sols2); California kissing bug (Triap1); *Blattella germanica* (Blag1.0101, Blag1.0102, Blag1.0103, Blag1.02, Blag6.0101, Blag6.0201, Blag6.0301); *Periplaneta Americana* (Pera1.0101, Pera1.0102, Pera1.0103, Pera1.0104, Pera1.02, Pera3.01, Pera3.0201, Pera3.0202, Pera3.0203, Pera7.0101, Pera7.0102); Vespa crabo (Vespc5.0101, Vespc5.0101); and *Vespa mandarina* (Vesp m 1.01, Vesp m 1.02) |
| Rubber | rubber (latex)(Hevb1, Hevb2, Hevb3, Hevb4, Hevb5, Hevb6.01, Hevb6.02, Hevb6.03, Hevb7.01, Hevb7.02, Hevb8, Hevb9, Hevb10, Hevb11, Hevb12, Hevb13); *Hevea brasiliensis* (Hevb6.01, Hevb6.0201, Hevb6.0202, Hevb6.03, Hevb8.0101, Hevb8.0102, Hevb8.0201, Hevb8.0202, Hevb8.0203, Hevb8.0204, Hevb10.0101, Hevb10.0102, Hevb10.0103, Hevb11.0101, Hevb11.0102) |
| Others | Nematode (Anis1, Anis2, Anis3, Anis4); pigeon tick (Argr1); worm (Ascs1); papaya (Carp1); soft coral (Denn1); human autoallergens (Homs1, Homs2, Homs3, Homs4, Homs5); obeche (Trips1) |

TABLE B6

Infectious Agent-derived Epitopes

| Infectious Agent | Epitope |
|---|---|
| *Mycobacterium tuberculosis* | isocitrate dehydrogenase (ICDs) |
| Influenza virus | Hemagglutinin (H1), neuraminidase (N1) |
| Dengue virus | envelope (E) |
| *Toxoplasma gondii* | microneme proteins, SAG1, SAG2, GRA1, GRA2, GRA4, GRA6, GRA7, GRA3, ROP1, ROP2, p30, MIC3, MIC2, M2AP, p29, p35, p66 |
| *Entamoeba histolytica* | M17, neutral thiol proteinase |
| *Streptococcus pneumonia* | Pneumolysin, pneumococcal histidine triad D (PhtD), pneumococcal choline-binding protein A (PcpA), pneumococcal histidine triad E (PhtE), LytB |
| *Mycoplasma pneumonia* | exotoxin |
| Epstein-Barr virus | VCA |
| *Helicobacter pylori* | CagA, Vacuolating protein, ureB, hsp60, ureH, urea, ferritin like protein |
| *Campylobacter jejuni* | PEB1, PEB3 |
| *Bacillus anthracis* | SAP |
| SARS virus | RNA-dependent replicases Ia and Ib, spike (S) protein, small envelope (E) protein, membrane (M) protein, and nucleocapsid (N) protein |
| Ebola virus | Nucleoprotein N |
| Schmallenberg virus | N nucleoprotein |
| enterovirus 71 | VPI protein |
| Japanese Encephalitis virus | soluble E protein, envelope E protein |
| Ross River virus | soluble E2 protein |
| Mayaro virus | soluble E2 protein |
| Equine Encephalitis viruses | soluble E2 protein |
| Akabane virus | N nucleoprotein |

TABLE B6-continued

Infectious Agent-derived Epitopes

| Infectious Agent | Epitope |
|---|---|
| human betacoronavirus | Nucleoprotein N, protein S |
| Hepatitis C virus | protein C, core antigen |
| Hepatitis E virus | protein C |
| *Plasmodium falciparum* | MSP-1 + AMA-1 protein |
| *Leptospira interrogans* | HbpA, LruA, LruB, or LipL32 |

In some instances, the biomarker to be detected using the present method is a micro RNA (miRNA) biomarker that is associated with a disease or a health condition. The following Table B7 provides a list of miRNA biomarker that can be detected using the present invention, and their associated diseases/health conditions.

TABLE B7

Diagnostic miRNA Markers

| Disease/Condition | Marker* |
|---|---|
| Breast cancer | miR-10b, miR-21, miR-125b, miR-145, miR-155, miR-191, miR-382, MiR-1, miR-133a, miR-133b, miR-202, miR-1255a, miR-671-3p, miR-1827, miR-222, miR-744, miR-4306, miR-151-3p, miR-130, miR-149, miR-652, miR-320d, miR-18a, miR-181a, miR-3136, miR-629, miR-195, miR-122, miR-375, miR-184, miR-1299, miR381, miR-1246, miR-410, miR-196a, miR-429, miR-141, miR-376a, miR-370, miR-200b, miR-125a-5p, miR-205, miR-200a, miR-224, miR-494, miR-216a, miR-654-5p, miR-217, miR-99b, miR-885-3p, miR-1228, miR-483-5p, miR-200c, miR-3065-5p, miR-203, miR-1308, let-7a, miR-17-92, miR-34a, miR-223, miR-150, miR-15b, miR-199a-5p, miR-33a, miR-423-5p, miR-424, let-7d, miR-103, miR-23b, miR-30d, miR-425, miR-23a, miR-26a, miR-339-3p, miR-127-3p, miR-148b, miR-376a, miR-376c, miR-409-3p, miR-652, miR-801<br>(miR-92a, miR-548d-5p, miR-760, miR-1234, miR-18b, miR-605, miR-193b, miR-29) |
| Leukemia | miR-98, miR-155, miR-21, let-7, miR-126, miR-196b, miR-128, miR-195, miR-29a, miR-222, miR-20a, miR-150, miR-451, miR-135a, miR-486-5p, miR-92, miR-148a, miR-181a, miR-20a, miR-221, miR-625, miR-99b<br>(miR-92a, miR-15, miR-16, miR-15a, miR-16-1, miR-29) |
| Multiple myeloma | miR-15a, miR-16, miR-193b-365, miR-720, miR-1308, miR-1246, miR-1, miR-133a, miR-221, miR-99b, Let-7e, miR-125a-5p, miR-21, miR-181a/b, miR-106b-25, miR-32, miR-19a/b, miR-17-92, miR-17, miR-20, miR-92, miR-20a, miR-148a, miR-153, miR-490, miR-455, miR-642, miR-500, miR-296, miR-548d, miR-373, miR-554, miR-888, miR-203, miR-342, miR-631, miR-200a, miR-34c, miR-361, miR-9*, miR-200b, miR-9, miR-151, miR-218, miR-28-3p, miR-200c, miR-378, miR-548d-5p, miR-621, miR-140-5p, miR-634, miR-616, miR-130a, miR-593, miR-708, miR-200a*, miR-340, miR-760, miR-188-5p, miR-760, miR-885-3p, miR-590-3p, miR-885-5p, miR-7, miR-338, miR-222, miR-99a, miR-891a, miR-452, miR-98, miR-629, miR-515-3p, miR-192, miR-454, miR-151-3p, miR-141, miR-128b, miR-1227, miR-128a, miR-205, miR-27b, miR-608, miR-432, miR-220, miR-135a, miR-34a, miR-28, miR-412, miR-877, miR-628-5p, miR-532-3p, miR-625, miR-34b, miR-31, miR-106b, miR-146a, miR-210, miR-499-5p, miR-140, miR-188, miR-610, miR-27a, miR-142-5p, miR-603, miR-660, miR-649, miR-140-3p, miR-300, miR-335, miR-206, miR-20b, miR-130b, miR-183, miR-652, miR-133b, miR-191, miR-212, miR-194, miR-100m miR-1234m miR-182m miR-888, miR-30e-5p, miR-574, miR-135b, miR-125b, miR-502m miR-320, miR548-421, miR-129-3p, miR-190b, miR-18a, miR-549, 338-5p, miR-756-3p, miR-133a, miR-521, miR-486-3p, miR-553, miR-452*, miR-628-3p, miR-620, miR-566, miR-892a, miR-miR-339-5p, miR-628, miR-520d-5p, miR-297, miR-213, miR-519e*, miR-422a, miR-198, miR-122a, miR-1236, miR-548c-5p, miR-191*, miR-583, miR-376c, miR-34c-3p, miR-453, miR-509, miR-124a, miR-505, miR-208, miR-659, miR-146b, miR-518c, miR-665, miR-324-5p, miR-152, miR-548d, miR-455-3p<br>(miR-15a, miR-373*, miR-378*, miR-143, miR-337, miR-223, miR-369-3p, miR-520g, miR-485-5p, miR-524, miR-520h, miR-516-3p, miR-519d, miR-371-3p, miR-455, miR-520b, miR-518d, miR-624, miR-296, miR-16) |
| monoclonal gammopathy of undetermined significance | miR-21, miR-210, miR-9*, miR-200b, miR-222, miR-376<br>(miR-339, miR-328) |
| Myelodisplastic syndrome | (Let-7a, miR-16) |

TABLE B7-continued

Diagnostic miRNA Markers

| Disease/Condition | Marker* |
|---|---|
| Lymphoma | miR-155, miR-210, miR-21, miR-17-92, miR-18a, miR-181a, miR-222, miR-20a/b, miR-194, miR-29, miR-150, miR-155, miR-223, miR-221, let-7f, miR-146a, miR-15, miR-16-1, miR-34b/c, miR-17-5p (miR-20b, miR-184, miR-200a/b/c, miR-205, miR-34a, miR-29a, miR-29b-1, miR-139, miR-345, miR-125a, miR-126, miR-26a/b, miR-92a, miR-20a, miR-16, miR-101, miR-29c miR-138, miR-181b) |
| Lung cancer | let-7c, miR-100, miR-10a, miR-10b, miR-122a, miR-125b, miR-129, miR-148a, miR-150, miR-17-5p, miR-183, miR-18a*, miR-18b, miR-190, miR-192, miR-193a, miR-196b, miR-197, miR-19a, miR-19b, miR-200c, miR-203, miR-206, miR-20b, miR-210, miR-214, miR-218, miR-296, miR-30a-3p, miR-31, miR-346, miR-34c, miR-375, miR-383, miR-422a, miR-429, miR-448, miR-449, miR-452, miR-483, miR-486, miR-489, miR-497, miR-500, miR-501, miR-507, miR-511, miR-514, miR-516-3p, miR-520d, miR-527, miR-7, miR-92, miR-93, miR-99a, miR-25, miR-223, miR-21, miR-155, miR-556, miR-550, miR-939, miR-616*, miR-146b-3p and miR-30c-1*, miR-142-5p, miR-328, miR-127, miR-151, miR-451, miR-126, miR-425-5p, miR-222, miR-769-5p, miR-642, miR-202, miR-34a (let-7a, let-7d, let-7e, let-7g, let-7i, miR-1, miR-103, miR-106a, miR-125a, miR-130a, miR-130b, miR-133a, miR-145, miR-148b, miR-15a, miR-15b, miR-17-3p, miR-181d, miR-18a, miR-196a, miR-198, miR-199a, miR-199a*, miR-212, miR-22, miR-221, miR-23a, miR-23b, miR-26a, miR-27a, miR-27b, miR-29b, miR-30b, miR-30d, miR-30e-3p, miR-320, miR-323, miR-326, miR-331, miR-335, miR-339, miR-374, miR-377, miR-379, miR-410, miR-423, miR-433, miR-485-3p, miR-485-5p, miR-487b, miR-490, miR-491, miR-493, miR-493-3p, miR-494, miR-496, miR-502, miR-505, miR-519d, miR-539, miR-542-3p, miR-98) |
| Colorectal cancer | miR-29a, miR-17-3p, miR-92, miR-21, miR-31, miR-155, miR-92a, miR-141, mir-202, mir-497, mir-3065, mir-450a-2, mir-3154, mir-585, mir-3175, mir-1224, mir-3117, mir-1286 (miR-34) |
| Prostate cancer | miR-141, miR-375, miR-16, miR-92a, miR-103, miR-107, miR-197, miR-485-3p, miR-486-5p, miR-26a, miR-92b, miR-574-3p, miR-636, miR-640, miR-766, miR-885-5p, miR-141, miR-195, miR-375, miR-298, miR-346, miR-1-1, miR-1181, miR-1291, miR-133a-1, miR-133b, miR-1469, miR-148*, miR-153, miR-182, miR-182*, miR-183, miR-183*, miR-185, miR-191, miR-192, miR-1973, miR-200b, miR-205, miR-210, miR-33b*, miR-3607-5p, miR-3621, miR-378a, miR-429, miR-494, miR-582, miR-602, miR-665, miR-96, miR-99b*, miR-100, miR-125b, miR-143, miR-200a, miR-200c, miR-222, miR-296, and miR-425-5p |
| Ovarian cancer | miR-21, miR-92, miR-93, miR-126, miR-29a, miR-141, miR-200a/b/c, miR-203, miR-205, miR-214, miR-221, miR-222, miR-146a, miR-150, miR-193a-5p, miR-31, miR-370, let-7d, miR-508-5p, miR-152, miR-509-3-5p, miR-508-3p, miR-708, miR-431, miR-185, miR-124, miR-886-3p, hsa-miR-449, hsa-miR-135a, hsa-miR-429, miR-205, miR-20b, hsa-miR-142-5p, miR-29c, miR-182 (miR-155, miR-127, miR-99b) |
| Cervical cancer | miR-21, miR-9, miR-200a, miR-497 (miR-143, miR-203, miR-218) |
| Esophageal carcinoma | miR-21, hsa-miR-200a, hsa-miR-345, hsa-miR-373*, hsa-miR-630, hsa-miR-663, hsa-miR-765, hsa-miR-625, hsa-miR-93, hsa-miR-106b, hsa-miR-155, hsa-miR-130b, hsa-miR-30a, hsa-miR-301a, hsa-miR-15b (miR-375) |
| Gastric cancer | miR-17-5p, miR-21, miR-106a, miR-106b, miR-187, miR-371-5p, miR-378 (let-7a, miR-31, miR-192, miR-215, miR-200/141) |
| Pancreatic cancer, ductal adenocarcinoma | miR-210, miR-21, miR-155, miR-196a, miR-1290, miR-20a, miR-24, miR-25, miR-99a, miR-185, miR-191, miR-18a, miR-642b-3p, miR-885-5p, miR-22-3p, miR-675, miR-212, miR-148a*, miR-148, miR-187, let-7g*, miR-205, miR-944, miR-431, miR-194*, miR-769-5p, miR-450b-5p, miR-222, miR-222*, miR-146, miR-23a*, miR-143*, miR-216a, miR-891a, miR-409-5p, miR-449b, miR-330-5p, miR-29a*, miR-625 |
| Hepatocellular carcinoma | miR-500, miR-15b, miR-21, miR-130b, miR-183, miR-122, miR-34a, miR-16, miR-221, miR-222 |
| Melanoma | miR-150, miR-15b, miR-199a-5p, miR-33a, miR-423-5p, miR-424, miR-let-7d, miR-103, miR-23b, miR-30d, miR-425, miR-222, miR-23a, miR-26a, miR-339-3p |
| Squamous cell carcinoma | miR-184a |
| Bladder cancer | miR-126, miR-182 (urine), miR-16, miR-320 (miR-143, miR-145, miR-200/141) |
| Renal cancer | miR-1233, miR-199b-5p, miR-130b (miR-10b, miR-139-5p) |
| Oral cancer | miR-31, miR-24, miR-184; miR-34c; miR-137; miR-372; miR-124a; miR-21; miR-124b; miR-31; miR-128a; miR-34b; miR-154; miR-197; miR-132; miR-147; miR-325; miR-181c; miR-198; miR-155; miR-30a-3p; |

TABLE B7-continued

Diagnostic miRNA Markers

| Disease/Condition | Marker* |
|---|---|
| | miR-338; miR-17-5p; miR-104; miR-134; miR-213 (miR-200a, miR-125a, miR-133a; miR-99a; miR-194; miR-133; miR-219; miR-100; miR-125; miR-26b; miR-138; miR-149; miR-195; miR-107; and miR-139 (saliva)) |
| Head and neck cancer | miR-455-3p, miR-455-5p, miR-130b, miR-130b*, miR-801, miR-196a, miR-21, miR-31 |
| Endometrial cancer | miR-503, miR-424, miR-29b, miR-146a, miR-31 |
| Testicular cancer | miR-372, miR-373 |
| Glioblastoma | miR-21, miR-221, miR-222 |
| Thyroid cancer | miR-187, miR-221, miR-222, miR-146b, miR-155, miR-224, miR-197, miR-192, miR-328, miR-346, miR-512-3D, miR-886-5p, miR-450a, miR-301 b, miR-429, miR-542-3p, miR-130a, miR-146b-5p, miR-199a-5p, miR-193a-3p, miR-152, miR-199a-3p/miR-199b-3p, miR-424, miR-22, miR-146a, miR-339-3p, miR-365, let-7i*, miR-363*, miR-148a, miR-299-3p, let-7a*, miR-200b, miR-200c, miR-375, miR-451, miR-144, let-7i, miR-1826, miR-1201, miR-140-5p, miR-126, miR-126*, let-7f-2*, miR-148b, miR-21*, miR-342-3p, miR-27a, miR-145*, miR-513b, miR-101, miR-26a, miR-24, miR-30a*, miR-377, miR-518e7, miR-519a7, miR-519b-5p, miR-519c-5p, miR-5227, miR-523*, miR-222*, miR-452, miR-665, miR-584, miR-492, miR-744, miR-662, miR-219-2-3p, miR-631 and miR-637, miRPlus-E1078, miR-19a, miR-501-3p, miR-17, miR-335, miR-106b, miR-15a, miR-16, miR-374a, miR-542-5p, miR-503, miR-320a, miR-326, miR-330-3p, miR-1, miR-7b, miR-26b, miR-106a, miR-139, miR-141, miR-143, miR-149, miR-182, miR-190b, miR-193a, miR-193b, miR-211, miR-214, miR-218, miR-302c*, miR-320, miR-324, miR-338, miR-342, miR-367, miR-378, miR-409, miR-432, miR-483, miR-486, miR-497, miR-518f, miR-574, miR-616, miR-628, miR-663b, miR-888, miR-1247, miR-1248, miR-1262, and miR-1305 miR-21, miR-25, miR-32, miR-99b*, miR-125a, miR-125b, miR-138, miR-140, miR-181a, miR-213, miR-221, miR-222, and miR-345 |
| Ischemic heart disease/Myocardial infarction | miR-1, miR-30c, miR-133, miR-145, miR-208a/b, miR-499, miR-663b, miR-1291 (miR-126, miR-197, miR-223) |
| Heart failure | miR-29b, miR-122, miR-142-3p, miR-423-5p, miR-152, miR-155, miR-497 (miR-107, miR-125b, miR-126, miR-139, miR-142-5p, miR-497) |
| Stroke | miR-124, miR-145 (miR-210) |
| Coronary artery disease | miR-21, miR-27b, miR-130a, miR-134, miR-135a, miR-198, miR-210, miR-370 (miR-17, miR-92a, miR-126, miR-145m miR-155m miR-181a, miR-221, miR-222) |
| Diabetes | miR-9, miR-28-3p, miR-29a, miR-30d, miR-34a, miR-124a, miR-146a, miR-375, miR-503, 144 (miR-15a, miR-20b, miR-21, miR-24, miR-126, miR-191, miR-197, 223, miR-320, miR-486) |
| Hypertension | Hcmv-miR-UL112, Let-7e (miR-296-5p) |
| Chronic HCV infection | miR-155, miR-122, miR-125b, miR-146a, miR-21 |
| Liver injury | miR-122, miR-192 |
| Sepsis | miR-146a, miR223 |
| Arthritis | miR-125a-5p, miR-24, miR-26a, miR-9, miR-25, miR-98, miR-146a, miR-124a, miR-346, miR-223, miR-155 (miR-132, miR-146) |
| Systemic lupus erythematosus | (miR-200a/b/c, miR-205, miR-429, miR-192, miR-141, miR-429, miR-192 (urine or serum)) |
| Chron disease | miR-199a-5p, miR-362-3p, miR-532-3p, miR-plus-E1271, miR-340* (miR-149*, miR-plus-F1065) |
| Ulcerative colitis | miR-28-5p, miR-151-5p, miR-199-5p, miR-340*, miR-plus-E1271, miR-103-2*, miR-362-3p, miR-532-3p (miR-505) |
| Asthma | miR-705, miR-575, let-7d, miR-173p, miR-423-5p, miR-611, miR-674, let-7f-1, miR-23b, miR-223, miR-142-3p, let-7c, miR-25, miR-15b, let-7g, and miR-542-5p, miR-370 (miR-325, miR-134, miR-198, miR-721, miR-515-3p, miR-680, miR-601, miR-206, miR-202, miR-671, miR-381, miR-630, miR-759, miR-564, miR-709, miR-513, miR-298) |
| Chronic pulmonary disease | miR-148a, miR-148b, miR-152 |
| Idiopathic pulmonary fibrosis | miR-199a-5p |
| Alzheimer's disease | (miR-137, miR-181c, miR-9, miR-29a/b) |
| Duchenne muscular dystrophy | miR-1, miR-133a, miR-206 |

TABLE B7-continued

Diagnostic miRNA Markers

| Disease/Condition | Marker* |
|---|---|
| Multiple sclerosis | miR-633, miR-181c-5p (CSF), miR-17-5p, miR-193a, miR-326, miR-650, miR-155, miR-142-3p, miR-146a, miR-146b, miR-34a, miR-21, miR-23a, miR-199a, miR-27a, miR-142-5p, miR-193a, miR-15a, miR-200c, miR-130a, miR-223, miR-22, miR-320, miR-214, miR-629, miR-148a, miR-28, miR-195, miR-135a, miR-204, miR-660, miR-152, miR-30a-5p, miR-30a-3p, miR-365, miR-532, let-7c, miR-20b, miR-30d, miR-9, hsa-mir-18b, hsa-mir-493, hsa-mir-599, hsa-mir-96, hsa-mir-193, hsa-mir-328, hsa-mir-409-5p, hsa-mir-449b, hsa-mir-485-3p, hsa-mir-554 (miR-922 (CSF), miR-497, miR-1 and miR-126, miR-656, miR-184, miR-139, miR-23b, miR-487b, miR-181c, miR-340, miR-219, miR-338, miR-642, miR-181b, miR-18a, miR-190, miR-213, miR-330, miR-181d, miR-151, miR-140) |
| Preeclampsia | miR-210 (miR-152) |
| Gestational diabetes | (miR-29a, miR-132) |
| Platelet activity | miR-126, miR-197, miR-223, miR-24, miR-21 |
| Pregnancy/placenta-derived | miR-526a, miR-527, miR-520d-5p, miR-141, miR-149, miR-299-5p, miR-517a |
| Drug treatment for immunomodulation | miR-130a, miR-146b, miR-143, miR-145, miR-99b, miR-125a, miR-204, miR-424, miR-503 |
| Aging | (miR-151a-3p, miR-181a-5p, miR-1248) |

*miRNA markers in parentheses are downregulated

Environmental testing. As summarized above, the devices, systems and methods in the present invention can find use in analyzing an environmental sample, e.g., a sample from water, soil, industrial waste, etc., for the presence of environmental markers. An environmental marker can be any suitable marker, that can be captured by a capturing agent that specifically binds the environmental marker in a CROF device configured with the capturing agent. The environmental sample can be obtained from any suitable source, such as a river, ocean, lake, rain, snow, sewage, sewage processing runoff, agricultural runoff, industrial runoff, tap water or drinking water, etc. In some embodiments, the devices and systems in the present invention detect the concentration of lead or toxins in water. In some embodiments, the presence or absence, or the quantitative level of the environmental marker in the sample can be indicative of the state of the environment from which the sample was obtained. In some cases, the environmental marker can be a substance that is toxic or harmful to an organism, e.g., human, companion animal, plant, etc., that is exposed to the environment. In some cases, the environmental marker can be an allergen that can cause allergic reactions in some individuals who are exposed to the environment. In some instances, the presence or absence, or the quantitative level of the environmental marker in the sample can be correlated with a general health of the environment. In such cases, the general health of the environment can be measured over a period of time, such as week, months, years, or decades.

In some embodiments, the devices, systems and methods in the present invention further includes receiving or providing a report that indicates the safety or harmfulness for a subject to be exposed to the environment from which the sample was obtained based on information including the measured amount of the environmental marker. The information used to assess the safety risk or health of the environment can include data other than the type and measured amount of the environmental marker. These other data can include the location, altitude, temperature, time of day/month/year, pressure, humidity, wind direction and speed, weather, etc. The data can represent an average value or trend over a certain period (minutes, hours, days, weeks, months, years, etc.), or an instantaneous value over a shorter period (milliseconds, seconds, minutes, etc.).

The report can be generated by the device configured to read the CROF device, or can be generated at a remote location upon sending the data including the measured amount of the environmental marker. In some cases, an expert can be at the remote location or have access to the data sent to the remote location, and can analyze or review the data to generate the report. The expert can be a scientist or administrator at a governmental agency, such as the US Centers for Disease Control (CDC) or the US Environmental Protection Agency (EPA), a research institution, such as a university, or a private company. In certain embodiments, the expert can send to the user instructions or recommendations based on the data transmitted by the device and/or analyzed at the remote location.

A list of exemplary environmental markers is set forth in Table 8 of U.S. provisional application Ser. No. 62/234,538, filed on Sep. 29, 2015, which application is incorporated by reference herein.

TABLE B8

Environmental Markers

| CLASS/SOURCE | MARKER |
|---|---|
| Synthetic hormone analogues | 17beta-estradiol (E2), estrone (EI), estrogen (ES: EI + E2 + estriol (E3)), 17alfa-ethynylestradiol (EE2), 4-nonylphenpol, testosterone |

TABLE B8-continued

Environmental Markers

| CLASS/SOURCE | MARKER |
|---|---|
| Halogenated hydrocarbons | p,p'-DDE, p,p'-DDD, p,p'-DDT, o,p'-DDE, o,p'-DDE, o,p'-DDT, o,p'-DDD, chlordane, nonachlor, oxychlordane, heptachlor, heptachlor epoxide, pentachloroanisole, hexachlorobenzene, heptachlorbenzene, o,p'-methoxychlor, p,p'-methoxychlor, Hexachlorocyclopentadiene |
| Pesticides | manganese ethylene-bis-dithiocarbamate, diazinon, chlorphyrifos, carbofuran, carbaryl, malathion, dieldrin, fipronil, desulfinylfipronil, fipronil sulfide, fipronil sulfone, aldicarb, aldicarb sulfone, aldicarb sulfoxide, carbaryl, 3-hydroxycarbofuran, methiocarb, methomyl, , oxamyl, propoxur, alpha-HCH, gamma-HCH, beta-HCH, delta-HCH, azinphos-methyl, chlorpyrifos, disulfoton, parathion, fonofos, ethoprop, parathion-methyl, phorate, terbufos, cis-permethrin, trans-permethrin, propargite, aldrin, chloroneb, endosulfan I, endrin, isodrin, mirex, toxaphene, lindane, O-ethyl O-4-nitrophenyl phenylphosphono-thioate (EPN), fenitrothion, pirimiphos-methyl, deltamethrin |
| Herbicide | acetochlor, alachlor, metolachlor, atrazine, deethylatrazine, cyanazine, terbuthylazine, terbutryn, metribuzin, bentazon, EPTC, triflualin, molinate norflurazon, simazine, prometon, promteryn, tebuthiuron, 2,4-D, diuron, dacthal, bromacil, deisopropyl atrazine, hydroxyatrazine, deethylhydroxyatrazine, deisopropylhydroxyatrazine, acetochlor ESA, acetochlor OA, alachlor ESA, alachlor OA, metolachlor ESA, metolachlor OA, 2,6-diethylaniline, napropamide, pronamide, propachlor, propanil butylate, pebulate, propham, thiobencarb, triallate, dacthal, dacthal monoacid, 2,4-DB, dischlorprop, MCPA, MCPB, 2,4,5-T, 2,4,5-TP, benfluralin, ethalfluralin, oryzalin, pendimethalin, trifluralin, bentazon, norflurazon, acifluorfen, chloramben methyl ester, clopyralid, dicamba, picloram, dinoseb, DNOC, chlorothalonil, dichlobenil, 2,6-dichlorobenzamide (BAM), triclopyr, bromoxynil, bromacil, terbacil, fenuron, fluometuron, linuron, neburon, dalapon, diquat, endothall, Glyphosate, N-dealkylated triazines, mecoprop |
| Industrial material/waste | chromated copper arsenate, Carbon tetrachloride, Chlorobenzene, p-Dichlorobenzene, 1,2-Dichloroethanem, 1,1-Dichloroethylene, cis-1,2-Dichloroethylene, trans-1,2-Dichloroethylene, Dichloromethane, Di(2-ethylhexyl) adipate, Di(2-ethylhexyl) phthalate, Dibutyl phthalate (DBP), diethyl phthalate (DEP), dicyclohexyl phthalate (DCHP), Dioxin (2,3,7,8-TCDD), Epichlorohydrin, Ethylene dibromide, Polychlorinated biphenyls, Pentachlorophenol, styrene, Tetrachloroethylene, Toluene diisocyanate (TDI), 1,2,4-Trichlorobenzene, 1,1,1-Trichloroethane, 1,1,2-Trichloroethane, Trichloroethylene, perchloroethylene, Vinyl chloride, Xylenes, alkylphenol (AP), AP + APE, bisphenol A (BPA), benzene, Xylene, Toluene, Styrene, Toluidine, 2-(p-Tolyl)ethylamine, Ethylbenzene, 2-Methyl-naphthalene, and Propyl-benzene, PAH (polynuclear aromatic hydrocarbons) |
| Drinking water | Bromate, Chlorite, Haloacetic acids, Total Trihalomethanes, Chloramines, Chlorine, Chlorine dioxide, Benzo(a)pyrene, 4-tert-octylphenol |
| Household waste/Sewage runoff | Acrylamide, linear alkylbenzene sulfonates (LAS), alkyl ethoxylates (AE), alkylphenol ethoxylates (APE), triclosan |
| Poison/toxins | N-methylamino-L-alanine (BMAA), Clostridium botulinum neurotoxins, BoNT A, B, D, E, Ricin A, B, tetanus toxin, diphtheria toxin, pertussis toxin |
| Heavy metal | mercury/methylmercury, lead/tetraethyl lead, zinc, copper, nickel, cadmium, chromium(VI)/chromate, aluminum, iron, arsenic, cobalt, selenium, silver, antimony, thallium, polonium, radium, tin, metallothionein (in carp liver tissue) |
| Other metals/inorganic chemicals | Lithium, beryllium, manganese, barium, cyanide, fluoride |
| Pathogens/microbes (antigen in pretheses) | Anthrax (LF), Giardia lamblia, Legionella, Total Coliforms (including fecal coliform and E. Coli), Viruses (enteric) stapylococci (e.g., Staphylococcus epidermidis and Staphylococcus aureus (enterotoxin A, B, C, G, I, cells, TSST-1), Enterrococcus faecalis, Pseudomonas aeruginosa, Escherichia coli (Shiga-like toxin, F4, F5, H, K, O, bacteriophage K1, K5, K13), other gram-positive bacteria, and gram-negative bacilli. Clostridium difficile (Toxin A, B) Bacteroidetes, Cryptosporidium parvum (GP900, p68 or cryptopain, oocyst), Candida albicans<br>Bacillus anthracis, Bacillus stearothermophilus<br>Norovirus, Listeria monocytogenes (internalin), Leptospira interrogans, Leptospira biflexa, Clostridium perfringens (Epsilon toxin), Salmonella typhimurium, Yersinia pestis (F1, V antigens), Aspergillus flavus (aflatoxin), Aspergillus parasiticus (aflatoxin), avian influenza virus, Ebola virus (GP), Histoplasma capsulatum, Blastomyces dermatitidis (A antigen)<br>Gram-positive bacteria (teichoic acid), Gram-ngative bacteria (such as Pseudomonas aeruginosa, Klebsiella pneumoniae, Salmonella enteriditis, Enterobacter aerogenes, Enterobacter hermanii, Yersinia enterocolitica and Shigella sonnei)(LPS), Polio virus, Influenza type A virus<br>Disease specific prion (PrP-d) |
| Allergens | mite (Acas13, Blot1, Blot3, Blot4, Blot5, Blot6, Blot10, Blot11, Blot12, Blot13, Blot19); American house dust mite (Derf1, Derf2, Derf3, Derf7, Derf10, Derf11, Derf14, Derf15, Derf16, Derf17, Derf18w); house dust mite (Derm1); European house dust mite (Derp1, Derp2, Derp3, Derp4, Derp5, Derp6, Derp7, Derp8, Derp9, Derp10, Derp11, Derp14, Derp20, Derp21); mite |

TABLE B8-continued

Environmental Markers

| CLASS/SOURCE | MARKER |
|---|---|
| | (Eurm2; Eurm14); storage mite (Glyd2, Lepd2, Lepd5, Lepd7, Lepd10, Lepd13, Tyrp2, Tyrp13); *Dermatophagoides farinae* (Derf1.0101, Derf1.0102, Derf1.0103, Derf1.0104, Derf1.0105, Derf2.0101, Derf2.0102, Derf2.0103, Derf2.0104, Derf2.0105, Derf2.0106, Derf2.0107, Derf2.0108, Derf2.0109, Derf2.0110, Derf2.0111, Derf2.0112, Derf2.0113, Derf2.0114, Derf2.0115, Derf2.0116, Derf2.0117); *Dermatophagoides pteronyssinus* (Derp1.0101, Derp1.0102, Derp1.0103, Derp1.0104, Derp1.0105, Derp1.0106, Derp1.0107, Derp1.0108, Derp1.0109, Derp1.0110, Derp1.0111, Derp1.0112, Derp1.0113, Derp1.0114, Derp1.0115, Derp1.0116, Derp1.0117, Derp1.0118, Derp1.0119, Derp1.0120, Derp1.0121, Derp1.0122, Derp1.0123, Derp2.0101, Derp2.0102, Derp2.0103, Derp2.0104, Derp2.0105, Derp2.0106, Derp2.0107, Derp2.0108, Derp2.0109, Derp2.0110, Derp2.0111, Derp2.0112, Derp2.0113); *Euroglyphus maynei* (Eurm2.0101, Eurm2.0102); *Glycyphagus domesticus* (Glyd2.0101, Glyd2.0201); and *Lepidoglyphus destructor* (Lepd2.0101, Lepd2.0101, Lepd2.0101, Lepd2.0102, Lepd2.0201, Lepd2.0202) Pollen (Short Ragweed (*Ambrosia artemisiifolia*) allergen, Amb a 1, Amba2, Amba3, Amba5, Amba6, Amba7, Amba8, Amba9, Amba10); *Betula verrucosa* allergen, Bet v 1, *Phleum pratense* allergen, Phl p 5), giant ragweed (Ambt5); mugwort (Artv1, Artv2, Artv3, Artv4, Artv5, Artv6); sunflower (Hela1, Hela2, Hela3); *Mercurialis annua* (Mera1); lamb's-quarters, pigweed (Chea1); white goosefoot (Chea2, Chea3); Russian-thistle (Salk1); Rosy periwinkle (Catr1); English plantain (Plal1); Japanese hop (Humj1); *Parietaria judaica* (Parj1, Parj2, Parj3); *Parietaria officinalis* (Paro1); *Ambrosia artemisiifolia* (Amba8.0101, Amba8.0102, Amba9.0101, Amba9.0102); *Plantago lanceolata* (Plal1.0101, Plal1.0102, Plal1.0103); and *Parietaria judaica* (Parj1.0101, Parj1.0102, Parj1.0201, Par2.0101, Parj2.0102, Parj3.0101, Parj3.0102), Bermuda grass (Cynd1, Cynd7, Cynd12, Cynd15, Cynd22w, Cynd23, Cynd24); orchard grass (Dacg1, Dacg2, Dacg3, Dacg5); meadow fescue (Fesp4w); velvet grass (HolH); rye grass (Lolp1, Lolp2, Lolp3, Lolp5, Lolp11); canary grass (Phaa1); Timothy (Phlp1, Phlp2, Phlp4, Phlp5, Phlp6, Phlp11, Phlp12, Phlp13); Kentucky blue grass (Poap1, Poap5); Johnson grass (Sorh1); *Cynodon dactylon* (Cynd1.0101, Cynd1.0102, Cynd1.0103, Cynd1.0104, Cynd1.0105, Cynd1.0106, Cynd1.0107, Cynd1.0201, Cynd1.0202, Cynd1.0203, Cynd1.0204); *Holcus lanatus* (Holl1.0101, Holl1.0102); *Lolium perenne* (Lolp1.0101, Lolp1.0102, Lolp1.0103, Lolp5.0101, Lolp5.0102); *Phleum pretense* (Phlp1.0101, Phlp1.0102, Phlp4.0101, Phlp4.0201, Phlp5.0101, Phlp5.0102, Phlp5.0103, Phlp5.0104, Phlp5.0105, Phlp5.0106, Phlp5.0107, Phlp5.0108, Phlp5.0201, Phlp5.0202); and *Secale cereale* (Secc20.0101, Secc20.0201), Alder (Alng1); Birch (Betv1, Betv2, Betv3, Betv4, Betv6, Betv7); hornbeam (Carb1); chestnut (Cass1, Cass5, Cass8); hazel (Cora1, Cora2, Cora8, Cora9, Cora10, Cora11); White oak (Quea1); Ash (Frae1); privet (Ligv1); olive (Olee1, Olee2, Olee3, Olee4, Olee5, Olee6, Olee7, Olee8, Olee9, Olee10); Lilac (Syrv1); Sugi (Cryj1, Cryj2); cypress (Cupa1); common cypress (Cups1, Cups3w); mountain cedar (Juna1, Juna2, Juna3); prickly juniper (Juno4); mountain cedar (Juns1); eastern red cedar (Junv1); London plane tree (Plaa1, Plaa2, Plaa3); date palm (Phod2); *Betula verrucosa* (Betv1.0101, Betv1.0102, Betv1.0103, Betv1.0201, Betv1.0301, Betv1.0401, Betv1.0402, Betv1.0501, Betv1.0601, Betv1.0602, Betv1.0701, Betv1.0801, Betv1.0901, Betv1.1001, Betv1.1101, Betv1.1201, Betv1.1301, Betv1.1401, Betv1.1402, Betv1.1501, Betv1.1502, Betv1.1601, Betv1.1701, Betv1.1801, Betv1.1901, Betv1.2001, Betv1.2101, Betv1.2201, Betv1.2301, Betv1.2401, Betv1.2501, Betv1.2601, Betv1.2701, Betv1.2801, Betv1.2901, Betv1.3001, Betv1.3101, Betv6.0101, Betv6.0102); *Carpinus betulus* (Carb1.0101, Carb1.0102, Carb1.0103, Carb1.0104, Carb1.0105, Carb1.0106, Carb1.0106, Carb1.0106, Carb1.0106, Carb1.0107, Carb1.0107, Carb1.0108, Carb1.0201, Carb1.0301, Carb1.0302); *Corylus avellana* (Cora1.0101, Cora1.0102, Cora1.0103, Cora1.0104, Cora1.0201, Cora1.0301, Cora1.0401, Cora1.0402, Cora1.0403, Cora1.0404); *Ligustrum vulgare* (Ligv1.0101, Ligv1.01.02); *Olea europea* (Olee1.0101, Olee1.0102, Olee1.0103, Olee1.0104, Olee1.0105, Olee1.0106, Olee1.0107); *Syringa vulgaris* (Syrv1.0101, Syrv1.0102, Syrv1.0103); *Cryptomeria japonica* (Cryj2.0101, Cryj2.0102); and *Cupressus sempervirens* (Cups1.0101, Cups1.0102, Cups1.0103, Cups1.0104, Cups1.0105) mold (*Alternaria alternata* allergen, Alt a 1, Alta3, Alta4, Alta5, Alta6, Alta7, Alta8, Alta10, Alta12, Alta13, *Aspergillus fumigatus* allergen, Asp f 1, Aspf2, Aspf3, Aspf4, Aspf5, Aspf6, Aspf7, Aspf8, Aspf9, Aspf10, Aspf11, Aspf12, Aspf13, Aspf15, Aspf16, Aspf17, Aspf18, Aspf22w, Aspf23, Aspf27, Aspf28, Aspf29); *Aspergillus niger* (Aspn14, Aspn18, Aspn25); *Aspergillus oryzae* (Aspo13, Aspo21); *Penicillium brevicompactum* (Penb13, Penb26); *Penicillium chrysogenum* (Pench13, Pench18, Pench20); *Penicillium citrinum* (Penc3, Penc13, Penc19, Penc22w, Penc24); *Penicillium oxalicum* (Peno18); *Fusarium culmorum* (Fusc1, Fusc2); *Trichophyton rubrum* (Trir2, Trir4); *Trichophyton tonsurans* (Trit1, Trit4); *Candida albicans* (Canda1, Canda3); *Candida boidinii* (Candb2); *Psilocybe cubensis* (Psic1, Psic2); shaggy cap (Copd, Copc2, Copc3, Copc5, Copc7); *Rhodotorula mucilaginosa* (Rhom1, Rhom2); *Malassezia furfur* (Malaf2, Malaf3, Malaf4); *Malassezia sympodialis* |

TABLE B8-continued

Environmental Markers

| CLASS/SOURCE | MARKER |
|---|---|
| | (Malas1, Malas5, Malas6, Malas7, Malas8, Malas9, Malas10, Malas11, Malas12, Malas13); *Epicoccum purpurascens* (Epip1); and *Alternaria alternate* (Alta1.0101, Alta1.0102), *Aspergillus versicolor* antigen, *S. chartarum* antigen), *Cladosporium herbarum* (Clah2, Clah5, Clah6, Clah7, Clah8, Clah9, Clah10, Clah12); *Aspergillus flavus* (Aspf113); |
| | animals (*Bos domesticus* dander allergen, Bos d 2, Bosd3, Bosd4, Bosd5, Bosd6, Bosd7, Bosd8, Bosd2.0101, Bosd2.0102, Bosd2.0103, *Canis familiaris* allergen, Can f 1, Canf2, Canf3, Canf4, *Equus caballus* allergen, Equc1, Equc2, Equc3, Equc4, Equc5, *Felis domesticus* allergen, Fel d 1, Feld2, Feld3, Feld4, Feld5w, Feld6w, Feld7w, guinea pig (Cavp1, Cavp2); Mouse Urinary Protein (MUP, Musm1) allergen, Mus m 1, Rat Urinary Protein (RUP, Ratn1) allergen, Rat n 1., *Equus caballus* (Equc2.0101, Equc2.0102)) Mosquito (Aeda1, Aeda2); honey bee (Apim1, Apim2, Apim4, Apim6, Apim7); bumble bee (Bomp1, Bomp4); German cockroach (Blag1, Blag2, Blag4, Blag5, Blag6, Blag7, Blag8); American cockroach (Pera1, Pera3, Pera6, Pera7); midge (Chit1-9, Chit1.01, Chit1.02, Chit2.0101, Chit2.0102, Chit3, Chit4, Chit5, Chit6.01, Chit6.02, Chit7, Chit8, Chit9); cat flea (Ctef1, Ctef2, Ctef3); pine processionary moth (Thap1); silverfish (Leps1); white face hornet (Dolm1, Dolm2, Dolm5); yellow hornet (Dola5); wasp (Pola1, Pola2, Pola5, Pole1, Pole5, Polf5, Polg5, Polm5, Vesvi5); Mediterranean paper wasp (Pold1, Pold4, Pold5); European hornet (Vespc1, Vespc5); giant asian hornet (Vespm1, Vespm5); yellowjacket (Vesf5, Vesg5, Vesm1, Vesm2, Vesm5, Vesp5, Vess5, Vesv1, Vesv2, Vesv5); Australian jumper ant (Myrp1, Myrp2); tropical fire ant (Solg2, Solg4); fire ant (Soli2, Soli3, Soli4); Brazilian fire ant (Sols2); California kissing bug (Triap1); *Blattella germanica* (Blag1.0101, Blag1.0102, Blag1.0103, Blag1.02, Blag6.0101, Blag6.0201, Blag6.0301); *Periplaneta Americana* (Pera1.0101, Pera1.0102, Pera1.0103, Pera1.0104, Pera1.02, Pera3.01, Pera3.0201, Pera3.0202, Pera3.0203, Pera7.0101, Pera7.0102); *Vespa crabo* (Vespc5.0101, Vespc5.0101); and *Vespa mandarina* (Vesp m 1.01, Vesp m 1.02) |
| | Nematode (Anis1, Anis2, Anis3, Anis4); pigeon tick (Argr1); worm (Ascs1); papaya (Carp1); soft coral (Denn1); rubber (latex)(Hevb1, Hevb2, Hevb3, Hevb4, Hevb5, Hevb6.01, Hevb6.02, Hevb6.03, Hevb7.01, Hevb7.02, Hevb8, Hevb9, Hevb10, Hevb11, Hevb12, Hevb13); human autoallergens (Homs1, Homs2, Homs3, Homs4, Homs5); obeche (Trips1); and *Hevea brasiliensis* (Hevb6.01, Hevb6.0201, Hevb6.0202, Hevb6.03, Hevb8.0101, Hevb8.0102, Hevb8.0201, Hevb8.0202, Hevb8.0203, Hevb8.0204, Hevb10.0101, Hevb10.0102, Hevb10.0103, Hevb11.0101, Hevb11.0102) |

Foodstuff testing. As summarized above, the devices, systems and methods in the present invention can find use in analyzing a foodstuff sample, e.g., a sample from raw food, processed food, cooked food, drinking water, etc., for the presence of foodstuff markers. A foodstuff marker can be any suitable marker, such as those shown in Table B9, below, that can be captured by a capturing agent that specifically binds the foodstuff marker in a CROF device configured with the capturing agent. The environmental sample can be obtained from any suitable source, such as tap water, drinking water, prepared food, processed food or raw food, etc. In some embodiments, the presence or absence, or the quantitative level of the foodstuff marker in the sample can be indicative of the safety or harmfulness to a subject if the food stuff is consumed. In some embodiments, the foodstuff marker is a substance derived from a pathogenic or microbial organism that is indicative of the presence of the organism in the foodstuff from which the sample was obtained. In some embodiments, the foodstuff marker is a toxic or harmful substance if consumed by a subject. In some embodiments, the foodstuff marker is a bioactive compound that can unintentionally or unexpectedly alter the physiology if consumed by the subject. In some embodiments, the foodstuff marker is indicative of the manner in which the foodstuff was obtained (grown, procured, caught, harvested, processed, cooked, etc.). In some embodiments, the foodstuff marker is indicative of the nutritional content of the foodstuff. In some embodiments, the foodstuff marker is an allergen that can induce an allergic reaction if the foodstuff from which the sample is obtained is consumed by a subject.

In some embodiments, the devices, systems and methods in the present invention further includes receiving or providing a report that indicates the safety or harmfulness for a subject to consume the food stuff from which the sample was obtained based on information including the measured level of the foodstuff marker. The information used to assess the safety of the foodstuff for consumption can include data other than the type and measured amount of the foodstuff marker. These other data can include any health condition associated with the consumer (allergies, pregnancy, chronic or acute diseases, current prescription medications, etc.).

The report can be generated by the device configured to read the CROF device, or can be generated at a remote location upon sending the data including the measured amount of the foodstuff marker. In some cases, a food safety expert can be at the remote location or have access to the data sent to the remote location, and can analyze or review the data to generate the report. The food safety expert can be a scientist or administrator at a governmental agency, such as the US Food and Drug Administration (FDA) or the CDC, a research institution, such as a university, or a private company. In certain embodiments, the food safety expert can send to the user instructions or recommendations based on the data transmitted by the device and/or analyzed at the remote location.

TABLE B9

| Foodstuff Markers | |
|---|---|
| Source/Class | Marker/target |
| Pathogens/ microbes | *Bacillus anthracis* (LF), *Giardia lamblia*, *Legionella*, Total Coliforms (including fecal coliform and *E. Coli*), Viruses (enteric) *stapylococci* (e.g., *Staphylococcus epidermidis* and *Staphylococcus aureus* (enterotoxin A, B, C, G, I, cells, TSST-1), *Enterrococcus faecalis*, *Pseudomonas aeruginosa*, *Escherichia coli* (Shiga-like toxin, F4, F5, H, K, O, bacteriophage K1, K5, K13), other gram-positive bacteria, and gram-negative bacilli. *Clostridium difficile* (Toxin A, B), Bacteroidetes, *Cryptosporidium parvum* (GP900, p68 or cryptopain, oocyst), *Candida albicans*, *Bacillus anthracis*, *Bacillus stearothermophilus*, *Bacillus cereus*, *Bacillus licheniformis*, *Bacillus subtilis*, *Bacillus pumilus*, *Bacillus badius*, *Bacillus globigii*, *Salmonella typhimurium*, *Escherichia coli* O157:H7, Norovirus, *Listeria monocytogenes* (internalin), *Leptospira interrogans*, *Leptospira biflexa*, *Campylobacter jejuni*, *Campylobacter coli*, *Clostridium perfringens*, *Aspergillus flavus* (aflatoxins), *Aspergillus parasiticus* (aflatoxins), Ebola virus (GP), *Histoplasma capsulatum*, *Blastomyces dermatitidis* (A antigen), Gram-positive bacteria (teichoic acid), Gram-negative bacteria (such as *Pseudomonas aeruginosa*, *Klebsiella pneumoniae*, *Salmonella enteriditis*, *Enterobacter aerogenes*, *Enterobacter hermanii*, *Yersinia enterocolitica* and *Shigella sonnei*)(LPS), Polio virus, Influenza type A virus, Disease specific prion (PrP-d), Hepatitis A virus, *Toxoplasma gondii*, *Vibrio cholera*, *Vibrio parahaemolyticus*, *Vibrio vulnificus*, *Enterococcus faecalis*, *Enterococcus faecium* |
| Toxins/ carcinogens | N-methylamino-L-alanine (BMAA), *Clostridium botulinum* neurotoxins, BoNT A, B, Ricin A, B; diphtheria toxin; Aristolochic acid; Colchicine, Ochratoxin A, Sterigmatocystin, Ergotamine, Fumonisins, Fusarin C, domoic acid, Brevetoxin, Mycotoxins |
| Halogenated hydrocarbons | Heptachlor, chlordane |
| Heavy metals | Lead, mercury, cadmium |
| Allergens | peanut (Ara h 1, Ara h 2, Ara h 6), fish, shellfish, mollusks, shrimp (*D. pteronyssinus tropomyosin* allergen, Der p 10) Cod (Gadc1); Atlantic salmon (Sals1); domestic cattle milk (Bosd4, Bosd5, Bosd6, Bosd7, Bosd8); chicken/egg (Gald1, Gald2, Gald3, Gald4, Gald5); shrimp (Mete1); shrimp (Pena1, Peni1); black tiger shrimp (Penm1, Penm2); squid (Todp1), brown garden snail (Helas1); abalone (Halm1); edible frog (Rane1, Rane2); oriental mustard (Braj1); rapeseed (Bran1); cabbage (Brao3); turnip (Brar1, Brar2); barley (Horv15, Horv16, Horv17, Horv21); rye (Secc20); wheat (Tria18, Tria19, Tria25, Tria26, gliadin); corn (Zeam14, Zeam25); rice (Orys1), celery (Apig1, Apig4, Apig5); carrot (Dauc1, Dauc4); hazelnut (Cora1.04, Cora2, Cora8); strawberry (Fraa1, Fraa3, Fraa4); apple (Mald1, Mald2, Mald3, Mald4); pear (Pyrc1, Pyrc4, Pyrc5); avocado (Persa1); apricot (Pruar1, Pruar3); sweet cherry (Pruav1, Pruav2, Pruav3, Pruav4); European plum (Prud3); almond (Prudu4); peach (Prup3, Prup4); asparagus (Aspao1); saffron crocus (Cros1, Cros2); lettuce (Lacs1); grape (Vitv1); banana (Musxp1); pineapple (Anac1, Anac2); lemon (Citl3); sweet orange (Cits1, Cits2, Cits3); litchi (Litd); yellow mustard (Sinai); soybean (Glym1, Glym2, Glym3, Glym4); mung bean (Vigr1); peanut (Arah1, Arah2, Arah3, Arah4, Arah5, Arah6, Arah7, Arah8); lentil (Lenc1, Lenc2); pea (Piss1, Piss2); kiwi (Actc1, Actc2); bell pepper (Capa1w, Capa2); tomato (Lyce1, Lyce2, Lyce3); potato (Solat1, Solat2, Solat3, Solat4); Brazil nut (Bere1, Bere2); black walnut (Jugn1, Jugn2); English walnut (Jugr1, Jugr2, Jugr3); Cashew (Anao1, Anao2, Anao3); Castor bean (Ricc1); sesame (Sesi1, Sesi2, Sesi3, Sesi4, Sesi5, Sesi6); muskmelon (Cucm1, Cucm2, Cucm3); Chinese-date (Zizm1); *Anacardium occidentale* (Anao1.0101, Anao1.0102); *Apium graveolens* (Apig1.0101, Apig1.0201); *Daucus carota* (Dauc1.0101, Dauc1.0102, Dauc1.0103, Dauc1.0104, Dauc1.0105, Dauc1.0201); *Citrus sinensis* (Cits3.0101, Cits3.0102); *Glycine max* (Glym1.0101, Glym1.0102, Glym3.0101, Glym3.0102); *Lens culinaris* (Lenc1.0101, Lenc1.0102, Lenc1.0103); *Pisum sativum* (Piss1.0101, Piss1.0102); *Lycopersicon esculentum* (Lyce2.0101, Lyce2.0102); *Fragaria ananassa* (Fraa3.0101, Fraa3.0102, Fraa3.0201, Fraa3.0202, Fraa3.0203, Fraa3.0204, Fraa3.0301); *Malus domestica* (Mald1.0101, Mald1.0102, Mald1.0103, Mald1.0104, Mald1.0105, Mald1.0106, Mald1.0107, Mald1.0108, Mald1.0109, Mald1.0201, Mald1.0202, Mald1.0203, Mald1.0204, Mald1.0205, Mald1.0206, Mald1.0207, Mald1.0208, Mald1.0301, Mald1.0302, Mald1.0303, Mald1.0304, Mald1.0401, Mald1.0402, Mald1.0403, Mald3.0101w, Mald3.0102w, Mald3.0201w, Mald3.0202w, Mald3.0203w, Mald4.0101, Mald4.0102, Mald4.0201, Mald4.0202, Mald4.0301, Mald4.0302); *Prunus avium* (Pruav1.0101, Pruav1.0201, Pruav1.0202, Pruav1.0203); and *Prunus persica* (Prup4.0101, Prup4.0201) |
| Synthetic hormone analogues | 17beta-estradiol (E2), estrone (EI), estrogen (ES: EI + E2 + estradiol (E3)), 1 7alfa-ethynylestradiol (EE2), 4-nonylphenpol, testosterone, Diethylstilbestrol (DES), recombinant bovine growth hormone (rBGH) |
| Pesticides | Dieldrin, carbaryl, chlorpyrifos, parathion, aldrin, endosulfan I, endrin, toxaphene, O-ethyl O-4-nitrophenyl phenylphosphono-thioate (EPN), fenitrothion, pirimiphos-methyl, thiabendazole, methiocarb, |

TABLE B9-continued

Foodstuff Markers

| Source/Class | Marker/target |
|---|---|
| | Carbendazim, deltamethrin, Avermectin, Carbaryl, Cyanazine, Kresoxim, resmethrin, kadethrin, cyhalothrin, biphenthrin, fenpropathrin, allethrin and tralomethrin; aromatic-substituted alkanecarboxylic acid esters such as fenvarerate, flucythrinate, fluvalinate and cycloprothrin; and non-ester compounds such as etofenprox, halfenprox (MTI-732), 1-(3-phenoxyphenyl)-4-(4-ethoxyphenyl)-4-methylpentane (MTI-790), 1-(3-phenoxy-4-fluorophenyl)-4-(4-ethoxyphenyl)-4-methylpentane (MTI-800), dimethyl-(4-ethoxyphenyl)-(3-phenoxybenzyloxy)silane (SSI-116), silafluofen and PP-682, carbofuran, triazophos |
| Herbicide | atrazine, deethylatrazine, cyanazine, terbuthylazine, terbutryn, molinate, simazine, prometon, promteryn, hydroxyatrazine, 2,6-dichlorobenzamide (BAM), N-dealkylated triazines, mecoprop, thiram, acetochlor, alachlor, Chlorothalonil, Chlorsulfuron, Fenoxaprop ethyl, Linuron, monuron, diuron, Quizalofop-ethyl, Imazalil, Iprodione, Iprovalicarb, Myclobutanil |
| Industrial material/waste | Dioxin (2,3,7,8-TCDD), 4-tert-octylphenol, bisphenol A (BPA), Styrene, Di(2-ethylhexyl) phthalate, Dibutyl phthalate (DBP), benzophenone, benzene, trichloroethylene, polychlorinated biphenyl (PCB), nonylphenol, p-cresol, melamine, xylene |
| Antibiotics | 3-Amino-5-morpholinomethyl-2-oxazolidone (AMOZ; tissue bound metabolite of furaltadone), oxytetracycline, rolitetracycline, Actinomycin D, Amikacin sulfate, Aminoglycosides, nitrofuran (AOZ), Chloramphenicol, Doxycycline, Streptomycin, gentamicin, neomycin, kanamycin, sulfamethazine, enrofloxacin, sulfadiazine, enrofloxacin |
| Food coloring/ additive/ preservative | Tartrazine, ethoxyquin, erythritol, penicillin, Fluoroquinolone, Malachite Green/Leucomalachite Green, C.I. Solvent Yellow 14 (Sudan I), |
| Food preparation | Acrylamide, 2-amino-3-methylimidazo(4,5-f)quinolone, Benzo[a]pyrene |
| Nutritional content | Vitamins A (retinol), B12 (cobalmins), B6 (pyridoxine), B1 (thiamin), B2 (riboflavin), B3 (niacin), B5 (D-pantothenic acid), B7 (biotin), B9 (folic acid), C, D, E (alpha-tocopherol); |
| Other | Caffeine, Ovine myofibril proteins, Etodolac |

TABLE B10

POC analytes

| Disease/Condition | Analyte |
|---|---|
| 1. Haematology | |
| Complete blood count (CBC) | RBCs, WBCs, Platelets |
| 2. Lipid panel | |
| Cholesterol level | Triglyceride, Total cholesterol, HDL cholesterol, LDL cholesterol |
| 3. Urinalysis | |
| Renal Diseases/ Kidney Function | pH, Protein, Glucose, Nitrites, Leukocyte esterase, Ketones, Blood cells, Casts, Crystals, Microorganisms, Squamous cells |
| 4. Diabetes | |
| Diabetes | Glucose, HbA1c, 11-8, CTSS, ITGB2, HLA-DRA, CD53, PLAG27, or MMP9; RBP4; 8-iso-prostaglandin F2α (8-iso-PGF2α), 11-dehydro-thromboxane B2 (TXM), C-peptide, Advanced glycosylation end products (AGEs), 1,5-anhydroglucitol, NGPTL3 and 4, autoantibodies (Zn transporter 8, glutamic acid decarboxylase (GAD)), ATP-binding cassette, sub-family C (CFTR/MRP), member 8; ATP-binding cassette, sub-family C (CFTR/MRP), member 9; angiotensin I converting enzyme (peptidyl-dipeptidase A) 1; adenylate cyclase activating polypeptide 1 (pituitary); adiponectin, C1Q and collagen domain containing; adiponectin receptor 1; adiponectin receptor 2; adrenomedullin; adrenergic, beta-2-, receptor, surface; advanced glycosylation end product-specific receptor; agouti related protein homolog (mouse); angiotensinogen (serpin peptidase inhibitor, clade A, member 8); angiotensin II receptor, type 1; angiotensin II receptor-associated protein; alpha-2-HS-glycoprotein; v-akt murine thymoma viral oncogene homolog 1; v-akt murine thymoma viral oncogene homolog 2; albumin; Alstrom syndrome 1; archidonate 12-lipoxygenase; ankyrin repeat domain 23; apelin, AGTRL 1 Ligand; apolipoprotein A-I; apolipoprotein A-II; apolipoprotein B (including Ag(x) antigen); apolipoprotein E; aryl hydrocarbon receptor nuclear translocator; Aryl hydrocarbon receptor nuclear translocator-like; arrestin, beta 1; arginine vasopressin (neurophysin II, antidiuretic hormone, Diabetes |

TABLE B10-continued

POC analytes

| Disease/Condition | Analyte |
|---|---|
| | insipidus, neurohypophyseal); bombesin receptor subtype 3; betacellulin; benzodiazepine receptor (peripheral); complement component 3; complement component 4A (Rodgers blood group); complement component 4B (Childo blood group); complement component 5; Calpain-10; cholecystokinin; cholecystokinin (CCK)-A receptor; chemokine (C-C motif) ligand 2; CD14 molecule; CD163 molecule; CD36 molecule (thrombospondin receptor); CD38 molecule; CD3d molecule, delta (CD3-TCR complex); CD3g molecule, gamma (CD3-TCR complex); CD40 molecule, TNF receptor superfamily member 5; CD40 ligand (TNF superfamily, member 5, hyper-IgM syndrome); CD68 molecule; cyclin-dependent kinase 5; complement factor D (adipsin); CASP8 and FADD-like apoptosis regulator; Clock homolog (mouse); chymase 1, mast cell; cannabinoid receptor 1 (brain); cannabinoid receptor 2 (macrophage); cortistatin; carnitine palmitoyltransferase I; carnitine palmitoyltransferase II; complement component (3b/4b) receptor 1; complement component (3d/Epstein Barr virus) receptor 2; CREB binding protein (Rubinstein-Taybi syndrome); C-reactive protein, pentraxin-related; CREB regulated transcription coactivator 2; colony stimulating factor 1 (macrophage); cathepsin B; cathepsin L; cytochrome P450, family 19, subfamily A, polypeptide 1; Dio-2, death inducer-obliterator 1; dipeptidyl-peptidase 4 (CD26, adenosine deaminase complexing protein 2); epidermal growth factor (beta-urogastrone); early growth response 1; epididymal sperm binding protein 1; ectonucleotide; pyrophosphatase/phosphodiesterase 1; E1A binding protein p300; coagulation factor XIII, A1 polypeptide; coagulation factor VIII, procoagulant component (hemophilia A); fatty acid binding protein 4, adipocyte; Fas (TNF receptor superfamily, member 6); Fas ligand (TNF superfamily, member 6); free fatty acid receptor 1; fibrinogen alpha chain; forkhead box A2; forkhead box O1A; ferritin; glutamate decarboxylase 2; galanin; gastrin; glucagon; glucokinase; gamma-glutamyltransferase 1; growth hormone 1; ghrelin/obestatin preprohormone; gastric inhibitory polypeptide; gastric inhibitory polypeptide receptor; glucagon-like peptide 1 receptor; guanine nucleotide binding protein (G protein), beta polypeptide 3; glutamic-pyruvate transaminase (alanine aminotransferase); gastrin releasing peptide (bombesin); gelsolin (amyloidosis, Finnish type); hemoglobin; hemoglobin, beta; hypocretin (orexin); neuropeptide; precursor; hepatocyte growth factor (hepapoietin A; scatter factor); hepatocyte nuclear factor 4, alpha; haptoglobin; hydroxysteroid (11-beta); dehydrogenase 1; heat shock 70 kDa protein 1B; islet amyloid polypeptide; intercellular adhesion molecule 1 (CD54), human rhinovirus receptor; interferon, gamma; insulin-like growth factor 1 (somatomedin C); insulin-like growth factor 2 (somatomedin A); insulin-like growth factor binding protein 1; insulin-like growth factor binding protein 3; inhibitor of kappa light polypeptide gene enhancer in B-cells, kinase beta; interleukin 10; interleukin 18 (interferon-gamma-inducing factor); interleukin 1, alpha; interleukin 1, beta; interleukin 1 receptor antagonist; interleukin 2; interleukin 6 (interferon, beta 2); interleukin 6 receptor; interleukin 8; inhibin, beta A (activin A, activin AB alpha polypeptide); insulin; insulin receptor; insulin promoter factor-1; insulin receptor substrate 1; insulin receptor substrate-2; potassium inwardly-rectifying channel, subfamily J, member 11; potassium inwardly-rectifying channel, subfamily J, member 8; klotho; kallikrein B, plasma (Fletcher factor) 1; leptin (obesity homolog, mouse); leptin receptor; legumain; lipoprotein, Lp(a); lipoprotein lipase; v-maf musculoaponeurotic brosarcoma oncogene homolog A (avian); mitogen-activated protein kinase 8; interacting protein 1; mannose-binding lectin (protein C) 2, soluble (opsonic defect); melanocortin 4 receptor; melanin-concentrating hormone receptor 1; matrix metallopeptidase 12 (macrophage elastase); matrix metallopeptidase 14 (membrane-inserted); matrix metallopeptidase 2 (gelatinase A, 72 kDa gelatinase, 72 kDa type IV collagenase); matrix metallopeptidase 9 (gelatinase B, 92 kDa gelatinase, 92 kDa type IV collagenase); nuclear receptor co-repressor 1; neurogenic differentiation 1; nuclear factor of kappa light polypeptide gene enhancer in B-cells 1(p105); nerve growth factor, beta polypeptide; non-insulin-dependent Diabetes Mellitus (common, type 2) 1; non-insulin-dependent Diabetes Mellitus (common, type 2) 2; Noninsulin-dependent Diabetes Mellitus 3; nischarin (imidazoline receptor); NF-kappaB repressing factor; neuronatin; nitric oxide synthase 2A; Niemann-Pick disease, type C2; natriuretic peptide precursor B; nuclear receptor subfamily 1, group D, member 1; nuclear respiratory factor 1; oxytocin, prepro-(neurophysin I); purinergic receptor P2Y, G-protein coupled, 10; purinergic receptor P2Y, G-protein coupled, 12; purinergic receptor P2Y, G-protein coupled, 2; progestagen-associated endometrial; protein (placental protein 14, pregnancy-associated endometrial alpha-2-globulin, alpha uterine protein); paired box gene 4; pre-B-cell colony enhancing factor 1; phosphoenolpyruvate carboxykinase 1 (PEPCK1); proprotein convertase; subtilisin/kexin type 1; placental growth factor, vascular; |

TABLE B10-continued

POC analytes

| Disease/Condition | Analyte |
|---|---|
| | endothelial growth factor-related protein; phosphoinositide-3-kinase, catalytic, alpha polypeptide; phosphoinositide-3-kinase, regulatory subunit 1 (p85 alpha); phospholipase A2, group XIIA; phospholipase A2, group IID; plasminogen activator, tissue; patatin-like phospholipase domain containing 2; proopiomelanocortin (adrenocorticotropin/beta-lipotropin/alpha-melanocyte stimulating hormone/beta- melanocyte stimulating hormone/beta-endorphin); paraoxonase 1 ESA, PON, Paraoxonase; peroxisome proliferative activated receptor, alpha; peroxisome proliferative activated receptor, delta; peroxisome proliferative activated receptor, gamma; peroxisome proliferative activated receptor, gamma, coactivator 1; protein phosphatase 1, regulatory (inhibitor) subunit 3A (glycogen and sarcoplasmic reticulum binding subunit, skeletal muscle); protein phosphatase 2A, regulatory subunit B'(PR 53); protein kinase, AMP-activated, beta 1 non-catalytic subunit; protein kinase, cAMP-dependent, catalytic, alpha; protein kinase C, epsilon; proteasome (prosome, macropain) 26S subunit, non-ATPase, 9 (Bridge-1); prostaglandin E synthase; prostaglandin-endoperoxide synthase 2 (prostaglandin G/H synthase and cyclooxygenase); protein tyrosine phosphatase, mitochondrial 1; Peptide YY retinol binding protein 4, plasma (RBP4); regenerating islet-derived 1 alpha (pancreatic stone protein, pancreatic thread protein); resistin; ribosomal protein S6 kinase, 90 kDa, polypeptide 1; Ras-related associated with Diabetes; serum amyloid A1; selectin E (endothelial adhesion molecule 1); serpin peptidase inhibitor, clade A (alpha-1 antiproteinase, antitrypsin), member 6; serpin peptidase inhibitor, clade E (nexin, plasminogen activator inhibitor type 1), member 1; serum/glucocorticoid regulated kinase; sex hormone-binding globulin; thioredoxin interacting protein; solute carrier family 2, member 10; solute carrier family 2, member 2; solute carrier family 2, member 4; solute carrier family 7 (cationic amino acid transporter, y+ system), member 1(ERR); SNF1-like kinase 2; suppressor of cytokine signaling 3; v-src sarcoma (Schmidt-Ruppin A-2) viral oncogene homolog (avian); sterol regulatory element binding transcription factor 1; solute carrier family 2, member 4; somatostatin receptor 2; somatostatin receptor 5; transcription factor 1, hepatic; LF-B1, hepatic nuclear factor (HNF1); transcription factor 2, hepatic, LF-B3, variant hepatic nuclear factor; transcription factor 7-like 2 (T-cell specific, HMG-box); transforming growth factor, beta 1 (Camurati-Engelmann disease); transglutaminase 2 (C polypeptide, protein-glutamine-gamma-glutamyltransferase); thrombospondin 1; thrombospondin, type I, domain containing 1; tumor necrosis factor (TNF superfamily, member 2); tumor necrosis factor (TNF superfamily, member 2); tumor necrosis factor receptor superfamily, member 1A; tumor necrosis factor receptor superfamily, member 1B; tryptophan hydroxylase 2; thyrotropin-releasing hormone; transient receptor potential cation channel, subfamily V, member 1; thioredoxin interacting protein; thioredoxin reductase 2; urocortin 3 (stresscopin); uncoupling protein 2 (mitochondrial, proton carrier); upstream transcription factor 1; urotensin 2; vascular cell adhesion molecule 1; vascular endothelial growth factor; vimentin; vasoactive intestinal peptide; vasoactive intestinal peptide receptor 1; vasoactive intestinal peptide receptor 2; von Willebrand factor; Wolfram syndrome 1 (wolframin); X-ray repair complementing defective repair in Chinese hamster cells 6; c-peptide; cortisol; vitamin D3; estrogen; estradiol; digitalis-like factor; oxyntomodulin; dehydroepiandrosterone sulfate (DHEAS); serotonin (5-hydroxytryptamine); anti-CD38 autoantibodies; gad65 autoantibody; Angiogenin, ribonuclease, RNase A family, 5; Hemoglobin A1c; Intercellular adhesion molecule 3 (CD50); interleukin 6 signal transducer (gp130, oncostatin M receptor); selectin P (granule embrane protein 140 kDa, antigen CD62); TIMP metallopeptidase inhibitor; Proinsulin; endoglin; interleukin 2 receptor, beta; insulin-like growth factor binding protein 2; insulin-like growth factor 1 receptor; fructosamine, N-acetyl-beta-d-glucosaminidase, pentosidine, advanced glycation end product, beta2-microglobulin, pyrraline |

5. Sexually Transmitted Diseases

| Disease/Condition | Analyte |
|---|---|
| Chlamydia | bacteria *Chlamydia trachomatis* |
| Gonorrhea | bacteria *Neisseria gonorrhoeae* |
| Syphilis | Antibodies, bacterial DNA |
| Trichomonas | protzoan *Trichomoniasis* |
| Human papillomavirus (HPV) | DNA or RNA of HPV virus |
| Genital herpes | Antibodies |
| Human Immunodeficiency Virus (HIV) | HIV antigen p24, Antibodies |

TABLE B10-continued

POC analytes

| Disease/Condition | Analyte |
|---|---|

6. Other Infectious Diseases

| | |
|---|---|
| Ebola | Antigen, IgM and IgG antibodies, RNA |
| Malaria | Antigen, Nucleic acids, Antibodies |
| Hepatitis B and Hepatitis C | Viral proteins, Antibodies, Viral DNA |
| Influenza | Viral proteins, Antibodies, Viral DNA |

7. Cardiac testing

| | |
|---|---|
| Cardiac markers | Troponin (I or T), Creatine Kinase (CK) and CK-MB, Myoglobin, hs-CRP, BNP and NT-proBNP |

8. Female Reproduction testing

| | |
|---|---|
| Pregnancy test | HCG (human chorionic gonadotropin) |
| Ovulation test | LH (luteinizing hormone) |

9. Drugs of Abuse

| | |
|---|---|
| Alcohol | Ethanol, ethyl glucuronide |
| Cocaine | Cocaine, Benzolecgonine, Ecgonine, Ecgonine Methyl Ester |
| Heroine | Heroine, 6MAM, Morphine |
| PCP | PCP, Phencyclidine Thienylcyclohexylpiperidine (TCP) |
| Amphetamines | Amphetamines (such as D-Amphetamine, D-Methamphetamine, L-Amphetamine, L-Methamphetamine, 3,4-Methylenedioxy-methamphetamine (MDMA), 3,4-Methylenedioxyamphetamine (MDA), 3,4-Methylenedioxyethylamphetamine (MDEA), Paramethoxyamphetamine (PMA)) |
| Methamphetamine | D-Methamphetamine, D-Amphetamine, L-Methamphetamine, Chloroquine, (+/−) Ephedrine, 3,4-Methylenedioxy-methamphetamine (MDMA), 3,4-Methylenedioxyamphetamine (MDA), 3,4-Methylenedioxyethylamphetamine (MDEA), Procaine |
| MDMA (Ecstasy) | MDMA, MDA, MDEA, D-Amphetamine, D-Methamphetamine, Paramethoxyamphetamine (PMA) |
| Barbiturates | Secobarbital, Phenobarbital, Butalbital, Allobarbital, Alphenal, Amorbarbital, Aprobarbital, Hexobarbital, Butabarbital, Pentobarbital |
| Phenobarbital | Phenobarbital, Butalbital, Amobarbital, Secobarbital |
| Benzodiazepines | Oxazepam, Alprazolam, Bromazepam, Chlordiazepoxide, Clobazam, Clonazepam, Clorazepate, Delorazepam, Desalkyflurazepam, Diazepam, Estazolam, Fentanyl, Flunitrazepam (Rohypnol ®), Flurazepam, a-Hydroxyalprazolam, Lorazepam (Ativan ®), Lormetazepam, Medazepam, Midazolam, Nitrazepam, Nordiazepam, Prazepam, Temazepam, Tetrazepam |
| *Cannabis* (Marijuana, etc.) | Δ9-THC, 11-Nor-Δ8-THC-9-COOH, 11-Nor-Δ9-THC-9-COOH, 11-Hydroxy-Δ9-tetrahydrocannabinol, Δ8-Tetrahydrocannabinol, Δ9-Tetrahydrocannabinol, Cannabinol, Cannabidiol, pentanoic acid, butanoic acid, 4-hydroxybutyl, 4-hydroxypentyl |
| Codeine | Morphine, Codeine, Diacetyl morphine (heroine), Ethylmorphine, Hydromorphone, Meperidine, 6-Monoacetylmorphine, Morphine-3-glucuronide, Oxycodone, Oxymorphone, Promethazine, Rifampicine, Thebaine, Trimipamine |
| Nicotine/Cotinine | Cotinine, Nicotine |
| Morphine | Morphine |
| Tricyclic antidepressants (TCA's) | Nortriptyline, Amitriptyline, Chlorpromazine, Clomipramine, Cyclobenzaprine, Desipramine, Diphenyldramine, Doxepine, Imipramine, Nordoxepine, Opipramol, Protriptyline, Perphenazine, Promazine, Promethazine, Trimipramine |
| LSD | LSD |
| Methadone | EDDP, Doxylamine, Methadone, Methadol |
| Methaqualone | Methaqualone, 3-hydroxy methaqualone, 4-hydroxy methaqualone, 2-hydroxy methaqualone, Amitriptyline, Carbamazepine, Nortriptyline, Phenytoin, Primidone, Theophyline |
| buprenorphine | Buprenorphine, Buprenorphine-3-B-d-gluconoride, Nor-Buprenorphine, Nor-Buprenorphine-3-B-d-gluconoride |
| Ketamine | Ketamine, Norketamine, Dextromethorphan, Dextrorphantartrate, EDDP, Phencyclidine, Promazine, Meperidine, D-Methamphetamine, Mephentermine h.s., MDEA, Nordoxepin hydrochloride, Promethazine, D-Norpropoxyphene, Methadone |
| MethCathinone | MethCathinone, 4-MMC (Mephedrone), 3-MMC (3-methylmethcathinone), 4-MEC (4-methylethcathinone), Methylone (MDMC, bk-MDMA), Cathinone, MDPV |

TABLE B10-continued

POC analytes

| Disease/Condition | Analyte |
| --- | --- |
| MDPV | MDPV, Cathinone, MethCathinone |
| methylphenidate | methylphenidate |
| tramadol | Tramadol, N-demethyl-tramadol, O-demethyl-tramadol |
| oxycodone | Oxycodone, Oxymorphone, Codeine, Diacetyl Morphine (Heroine), Ethylmorphine, Hydrocodone, Hydromorphone, Merperidine, 6-Monoacetylmorphine, Morphine, Morphine-3-beta-D-glucuronide, Thebaine |
| propoxyphene | D-propoxyphene, D-norpropoxyphene |
| Fentanyl | Methaqualone, Mecloqualone, 3-hydroxy methaqualone, 4-hydroxy methaqualone, 2-hydroxy methaqualone, Amitriptyline, Carbamazepine, Nortriptyline, Phenytoin, Primidone, Theophyline |

10. Coagulation Disorders

| | |
| --- | --- |
| Congenital hemophilia; Von Willebrand disease; Acquired hemophilia | Platelet, Fibronogen, Factor V, Anti-Xa, Factor XIII screen, D-dimer |

11. Fecal Occult Blood Test

| | |
| --- | --- |
| Colon Cancer; colon polyps; crohn's disease; hemorrhoids; anal fissures; intestinal infections; Ulcers; Ulcerative colitis | Blood cells, Hemoglobin, Fecal DNA |

12. Blood Gas and Electrolytes pH, $pCO_2$, $pO_2$, Sodium (Na+), Potassium (K+), Calcium (Ca++), HCO3, TCO2, SBE The health conditions that can be diagnosed or measured by the subject method, device and system include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause.

In certain embodiments, relative levels of nucleic acids in two or more different nucleic acid samples can be obtained using the above methods, and compared. In these embodiments, the results obtained from the above-described methods are usually normalized to the total amount of nucleic acids in the sample (e.g., constitutive RNAs), and compared. This can be done by comparing ratios, or by any other means. In particular embodiments, the nucleic acid profiles of two or more different samples can be compared to identify nucleic acids that are associated with a particular disease or condition.

In some examples, the different samples can consist of an "experimental" sample, i.e., a sample of interest, and a "control" sample to which the experimental sample can be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell can be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) can be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

7. Control and Measure the Sample Thickness Without Using Spacers

In some embodiments of the present invention, the spacers that are used to regulate the sample or a relevant volume of the sample are replaced by (a) positioning sensors that can measure the plate inner spacing, and (b) the devices that can control the plate positions and move the plates into a desired plate inner spacing based on the information provided the sensors. In some embodiment, all the spacers are replaced by translation stage, monitoring sensors and feedback system.

Measuring of Spacing and/or Sample Thickness Using Optical Method. In some embodiments, the measuring (f) of the spacing between the inner surfaces comprises the use of optical interference. The optical interference can use multiple wavelength. For example, the light signal due to the interference of a light reflected at the inner surface of the first plate and the second plate oscillate with the wavelength of the light. From the oscillation, one can determine the spacing between the inner surfaces. To enhance the interference signal, one of the inner surfaces or both can be coated with light reflection material.

In some embodiments, the measuring (f) of the spacing between the inner surfaces comprises taking optical imaging (e.g. taking a 2D (two-dimensional)/3D (three-dimensional) image of the sample and the image taking can be multiple times with different viewing angles, different wavelength, different phase, and/or different polarization) and image processing.

Measuring of Entire Sample Area or Volume Using Optical Methods. In some embodiments, the measuring (f) of the entire sample area or volume comprises taking optical imaging (e.g. taking a 2D (two-dimensional)/3D (three-dimensional) image of the sample and the image taking can be multiple times with different viewing angles, different wavelength, different phase, and/or different polarization) and image processing. The sample area means the area in the direction approximately parallel to the first plate and the second plate. The 3D imaging can use the method of fringe projection profilometry (FPP), which is one of the most prevalent methods for acquiring three-dimensional (3D) images of objects.

In some embodiments, the measuring of the sample area or volume by imaging comprises (a) calibration of the image scale by using a sample of the known area or volume (e.g., The imager is a smartphone and the dimensions of the image taken by the phone can be calibrated by comparing an image of the a sample of known dimension taken the same phone); (b) comparison of the image with the scale markers (rulers) placed on or near the first plate and second plate (discussed further herein), and (c) a combination of thereof.

As used herein, light can include visible light, ultraviolet light, infrared light, and/or near infrared light. Light can include wavelengths in the range from 20 nm to 20,000 nm.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, reference to "an agent" includes a single agent and multiple agents, and reference to "a camera" includes a single camera and multiple cameras.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function can additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entity specifically identified. Thus, as a non-limiting example, a reference to "A and/or B," when used in conjunction with open-ended language such as "comprising" may refer, in some embodiments, to A only (optionally including entity other than B); in certain embodiments, to B only (optionally including entity other than A); in yet certain embodiments, to both A and B (optionally including other entity). These entity may refer to elements, actions, structures, steps, operations, values, and the like.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

What is claimed is:

1. A device for forming a thin fluidic sample layer with a uniform predetermined thickness by pressing with an imprecise force, comprising:

a first plate, a second plate, and spacers, wherein:
  (i) the plates are movable relative to each other into different configurations;
  (ii) at least one of the first and second plates is flexible;
  (iii) each of the plates comprises, on its respective inner surface, a sample contact area for contacting a fluidic sample;
  (iv) each of the plates comprises, on its respective outer surface, a force area for applying a force that forces the plates together;
  (v) one or both of the plates comprise the spacers that are permanently fixed on the inner surface of a respective plate;
  (vi) the spacers have a predetermined substantially uniform height that is equal to or less than 200 microns, a predetermined width, and a predetermined inter-spacer-distance;
  (vii) the fourth power of the inter-spacer-distance (ISD) divided by the thickness (h) and the Young's modulus (E) of the at least one flexible plate ($ISD^4/(hE)$) is $5 \times 10^6$ $\mu m^3$/GPa or less;
  (viii) the thickness of the at least one flexible plate times the Young's modulus of the at least one flexible plate is in the range 60 to 750 GPa-um; and
  (ix) at least one of the spacers is inside the sample contact area;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample deposition in the open configuration; and in the closed configuration: at least part of the sample is compressed by the two plates into a layer of uniform thickness and is substantially stagnant relative to the plates, wherein the uniform thickness of the layer is confined by the sample contact areas of the two plates and is regulated by the plates and the spacers; and the imprecise pressing force has a magnitude that is not precisely known or precisely predictable at the time the imprecise pressing force is applied.

2. A system for rapidly analyzing a sample, comprising:
(i) the device of claim 1, and
(ii) a camera,
wherein the camera images the sample area of the device.

3. The device of claim 1, wherein the imprecise pressing force has a magnitude in a range of 1N to 20 N.

4. The device of claim 1, wherein the imprecise pressing force has a pressure in a range of 0.1 psi to 280 psi.

5. The device of claim 1, wherein the inter-spacer-distance (ISD) is equal or less than about 120 um (micrometer).

6. The device of claim 1, wherein the fourth power of the inter-spacer-distance (ISD) divided by the thickness (h) and the Young's modulus (E) of the at least one flexible plate ($ISD^4/(hE)$) is $5 \times 10^5$ $um^3$/GPa or less, and wherein a thickness of the at least one flexible plate times the Young's modulus of the at least one flexible plate is in the range of 100 to 550 GPa-um.

7. The device of claim 1, wherein a thickness of the at least one flexible plate times the Young's modulus of the at least one flexible plate is in the range of 100 to 550 GPa-um.

8. The device of claim 1, wherein the spacers functions as a location marker, a scale marker, an imaging marker, or any combination thereof.

9. The device of claim 1, wherein the spacers function as a scale marker.

10. The device of claim 1, wherein the surface of one or both of the plates is coated with a dry reagent.

11. The device of claim 1, wherein the spacers have a spacer height 40 um or less.

12. The device of claim 1, wherein the imprecise pressing force has a pressure in the range of 0.01 $kg/cm^2$ to 100 $kg/cm^2$.

13. The device of claim 1, wherein one or both plate sample contact surfaces comprise one or a plurality of binding sites that each bind and immobilize a respective analyte.

14. The device of claim 1, wherein one or both of the plate comprises one or a plurality of storage sites that each stores a reagent or reagents.

15. The device of claim 1, wherein one or both of the plate comprises one or a plurality of amplification sites that are each capable of amplifying a signal from the analyte or a label of the analyte when the analyte or label is 500 nm from the amplification site.

16. The device of claim 1, wherein one or both of the plates comprises a release time control material delays the time that the dry regent starts are released into the sample by at least 3 (three) seconds.

17. The device of claim 1, wherein the analyte comprises a molecule, cells, tissues, viruses, or nanoparticles with different shapes.

18. The system of claim 2, further comprising a processor that analyzes the image to measure the analyte in the sample.

19. The device of claim 18, further comprising a mobile communication device for sending and receiving data to or from a remote location.

20. The device of claim 19, further comprising a light source.

* * * * *